(12) United States Patent
Oberkircher

(10) Patent No.: US 12,079,460 B2
(45) Date of Patent: Sep. 3, 2024

(54) PROFILES FOR MODULAR ENERGY SYSTEM

(71) Applicant: Cilag GmbH International, Zug (CH)

(72) Inventor: Brendan J. Oberkircher, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/851,719

(22) Filed: Jun. 28, 2022

(65) Prior Publication Data

US 2023/0418450 A1 Dec. 28, 2023

(51) Int. Cl.
| | |
|---|---|
| *G06F 3/04847* | (2022.01) |
| *G06F 3/0482* | (2013.01) |
| *G16H 40/40* | (2018.01) |
| *G16H 40/67* | (2018.01) |

(52) U.S. Cl.
CPC ........ *G06F 3/04847* (2013.01); *G06F 3/0482* (2013.01); *G16H 40/40* (2018.01); *G16H 40/67* (2018.01)

(58) Field of Classification Search
CPC .... G06F 3/0482; G06F 3/04847; G06F 40/40; G06F 40/67
See application file for complete search history.

(56) References Cited

U.S. PATENT DOCUMENTS

| | | |
|---|---|---|
| 4,171,700 A | 10/1979 | Farin |
| 4,378,801 A | 4/1983 | Oosten |
| 4,640,279 A | 2/1987 | Beard |
| 4,849,752 A | 7/1989 | Bryant |
| D303,787 S | 10/1989 | Messenger et al. |
| 5,041,110 A | 8/1991 | Fleenor |

(Continued)

FOREIGN PATENT DOCUMENTS

| | | |
|---|---|---|
| EP | 0408160 A1 | 1/1991 |
| EP | 0473987 A1 | 3/1992 |

(Continued)

OTHER PUBLICATIONS

Sorrells, P., "Application Note AN680. Passive RFID Basics," retrieved from http://ww1.microchip.com/downloads/en/AppNotes/00680b.pdf on Feb. 26/2020, Dec. 31, 1998, pp. 1-7.

(Continued)

*Primary Examiner* — Seth A Silverman
(74) *Attorney, Agent, or Firm* — Frost Brown Todd LLP

(57) ABSTRACT

Devices, systems, and methods for implementing operational setting profiles for modular energy systems are disclosed herein. In some aspects, a modular energy system can include an energy module, a memory, and a display screen. The energy module can include a plurality of ports. The memory can include profiles including operational settings implementable by the modular energy system. The display screen can be configured to render a graphical user interface (GUI). The GUI can be configured to display a plurality of widgets corresponding to the ports and display a window configured to allow a user to select from the plurality of profiles comprised in the memory. Based on the user selecting one of the profiles, the GUI can populate the widgets with information related to the configuration of operational settings of the profile.

21 Claims, 46 Drawing Sheets

(56) References Cited

U.S. PATENT DOCUMENTS

| | | |
|---|---|---|
| D327,061 S | 6/1992 | Soren et al. |
| 5,189,277 A | 2/1993 | Boisvert et al. |
| 5,204,669 A | 4/1993 | Dorfe et al. |
| 5,318,563 A | 6/1994 | Malis et al. |
| 5,325,270 A | 6/1994 | Wenger et al. |
| 5,425,375 A | 6/1995 | Chin et al. |
| D379,346 S | 5/1997 | Mieki |
| 5,690,504 A | 11/1997 | Scanlan et al. |
| 5,693,042 A | 12/1997 | Boiarski et al. |
| 5,724,468 A | 3/1998 | Leone et al. |
| 5,788,688 A | 8/1998 | Bauer et al. |
| 5,910,139 A | 6/1999 | Cochran et al. |
| 6,049,467 A | 4/2000 | Tamarkin et al. |
| 6,055,458 A | 4/2000 | Cochran et al. |
| D431,811 S | 10/2000 | Nishio et al. |
| 6,179,136 B1 | 1/2001 | Kluge et al. |
| 6,269,411 B1 | 7/2001 | Reasoner |
| 6,273,750 B1 | 8/2001 | Malkowski, Jr. |
| 6,288,606 B1 | 9/2001 | Ekman et al. |
| 6,416,471 B1 | 7/2002 | Kumar et al. |
| 6,546,270 B1 | 4/2003 | Goldin et al. |
| 6,584,358 B2 | 6/2003 | Carter et al. |
| 6,611,793 B1 | 8/2003 | Burnside et al. |
| 6,731,514 B2 | 5/2004 | Evans |
| 6,760,218 B2 | 7/2004 | Fan |
| 6,839,238 B2 | 1/2005 | Derr et al. |
| 6,843,657 B2 | 1/2005 | Driscoll et al. |
| 6,888,848 B2 | 5/2005 | Beshai et al. |
| 6,913,471 B2 | 7/2005 | Smith |
| 7,009,511 B2 | 3/2006 | Mazar et al. |
| 7,044,949 B2 | 5/2006 | Orszulak et al. |
| 7,074,205 B1 | 7/2006 | Duffy et al. |
| 7,134,994 B2 | 11/2006 | Alpert et al. |
| 7,171,784 B2 | 2/2007 | Eenigenburg |
| 7,217,269 B2 | 5/2007 | El-Galley et al. |
| 7,252,664 B2 | 8/2007 | Nasab et al. |
| 7,331,699 B2 | 2/2008 | Gawalkiewicz et al. |
| 7,344,532 B2 | 3/2008 | Goble et al. |
| 7,353,068 B2 | 4/2008 | Tanaka et al. |
| D575,792 S | 8/2008 | Benson |
| 7,408,439 B2 | 8/2008 | Wang et al. |
| D579,876 S | 11/2008 | Novotney et al. |
| D583,328 S | 12/2008 | Chiang |
| 7,496,418 B2 | 2/2009 | Kim et al. |
| D589,447 S | 3/2009 | Sasada et al. |
| 7,500,747 B2 | 3/2009 | Howell et al. |
| 7,518,502 B2 | 4/2009 | Austin et al. |
| 7,563,259 B2 | 7/2009 | Takahashi |
| 7,601,149 B2 | 10/2009 | DiCarlo et al. |
| 7,637,907 B2 | 12/2009 | Blaha |
| 7,656,671 B2 | 2/2010 | Liu et al. |
| 7,757,028 B2 | 7/2010 | Druke et al. |
| D631,252 S | 1/2011 | Leslie |
| 7,932,826 B2 | 4/2011 | Fritchie et al. |
| 7,945,065 B2 | 5/2011 | Menzl et al. |
| 7,945,342 B2 | 5/2011 | Tsai et al. |
| 7,982,776 B2 | 7/2011 | Dunki-Jacobs et al. |
| 7,995,045 B2 | 8/2011 | Dunki-Jacobs |
| 8,019,094 B2 | 9/2011 | Hsieh et al. |
| D655,678 S | 3/2012 | Kobayashi et al. |
| D657,368 S | 4/2012 | Magee et al. |
| 8,187,263 B2 | 5/2012 | Behnke et al. |
| 8,218,279 B2 | 7/2012 | Liao et al. |
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,504,136 B1 | 8/2013 | Sun et al. |
| 8,540,709 B2 | 9/2013 | Allen |
| 8,567,393 B2 | 10/2013 | Hickle et al. |
| D704,839 S | 5/2014 | Juzkiw et al. |
| 8,795,001 B1 | 8/2014 | Lam et al. |
| 8,819,581 B2 | 8/2014 | Nakamura et al. |
| 8,840,609 B2 | 9/2014 | Stuebe |
| D716,333 S | 10/2014 | Chotin et al. |
| 8,911,437 B2 | 12/2014 | Horlle et al. |
| 8,917,513 B1 | 12/2014 | Hazzard |
| 8,920,186 B2 | 12/2014 | Shishikura |
| 8,923,012 B2 | 12/2014 | Kaufman et al. |
| 8,968,296 B2 | 3/2015 | McPherson |
| 8,986,288 B2 | 3/2015 | Konishi |
| 9,017,326 B2 | 4/2015 | DiNardo et al. |
| D729,267 S | 5/2015 | Yoo et al. |
| 9,055,870 B2 | 6/2015 | Meador et al. |
| 9,065,394 B2 | 6/2015 | Lim et al. |
| 9,129,054 B2 | 9/2015 | Nawana et al. |
| 9,160,853 B1 | 10/2015 | Daddi et al. |
| 9,168,054 B2 | 10/2015 | Turner et al. |
| 9,168,091 B2 | 10/2015 | Janssen et al. |
| 9,198,711 B2 | 12/2015 | Joseph |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,281,615 B1 | 3/2016 | Plaza et al. |
| 9,320,646 B2 | 4/2016 | Todd et al. |
| 9,345,481 B2 | 5/2016 | Hall et al. |
| 9,345,900 B2 | 5/2016 | Wu et al. |
| 9,351,653 B1 | 5/2016 | Harrison |
| 9,427,255 B2 | 8/2016 | Griffith et al. |
| 9,430,438 B2 | 8/2016 | Biskup |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,491,895 B2 | 11/2016 | Steeves et al. |
| 9,532,827 B2 | 1/2017 | Morgan et al. |
| 9,589,720 B2 | 3/2017 | Akahane |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,666,974 B2 | 5/2017 | Bopp |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| D806,721 S | 1/2018 | Fischer |
| 9,867,670 B2 | 1/2018 | Brannan et al. |
| 9,892,564 B1 | 2/2018 | Cvetko et al. |
| 9,907,196 B2 | 2/2018 | Susini et al. |
| 9,971,395 B2 | 4/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |

(56) References Cited

U.S. PATENT DOCUMENTS

| | | |
|---|---|---|
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| D924,139 S | 7/2021 | Jayme |
| 11,056,244 B2 | 7/2021 | Shelton, IV et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,083,489 B2 | 8/2021 | Fujii et al. |
| 11,116,587 B2 | 9/2021 | Wolf et al. |
| D939,545 S | 12/2021 | Oberkircher et al. |
| 11,218,822 B2 | 1/2022 | Morgan et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |
| 11,298,128 B2 | 4/2022 | Messerly et al. |
| 11,304,763 B2 | 4/2022 | Shelton, IV et al. |
| 11,314,846 B1 | 4/2022 | Colin et al. |
| 11,350,978 B2 | 6/2022 | Henderson et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,471,206 B2 | 10/2022 | Henderson et al. |
| 11,478,820 B2 | 10/2022 | Bales, Jr. et al. |
| 11,504,192 B2 | 11/2022 | Shelton, IV et al. |
| 11,510,720 B2 | 11/2022 | Morgan et al. |
| 11,510,750 B2 | 11/2022 | Dulin et al. |
| 11,559,307 B2 | 1/2023 | Shelton, IV et al. |
| 11,564,678 B2 | 1/2023 | Scheib et al. |
| 11,571,205 B2 | 2/2023 | Scheib et al. |
| 11,576,677 B2 | 2/2023 | Shelton, IV et al. |
| 11,589,888 B2 | 2/2023 | Shelton, IV et al. |
| 11,607,239 B2 | 3/2023 | Swensgard et al. |
| 11,628,006 B2 | 4/2023 | Henderson et al. |
| 11,638,602 B2 | 5/2023 | Henderson et al. |
| 11,659,023 B2 | 5/2023 | Shelton, IV et al. |
| 11,666,368 B2 | 6/2023 | Henderson et al. |
| 11,678,925 B2 | 6/2023 | Henderson et al. |
| 11,684,400 B2 | 6/2023 | Jayme et al. |
| 11,684,401 B2 | 6/2023 | Oberkircher et al. |
| 11,696,789 B2 | 7/2023 | Petre et al. |
| 11,696,790 B2 | 7/2023 | Oberkircher et al. |
| 11,696,791 B2 | 7/2023 | Henderson et al. |
| 11,712,280 B2 | 8/2023 | Henderson et al. |
| 2001/0029315 A1 | 10/2001 | Sakurai et al. |
| 2003/0007321 A1 | 1/2003 | Dayley |
| 2003/0078631 A1 | 4/2003 | Nelson et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0111045 A1 | 6/2004 | Sullivan et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0113823 A1 | 5/2005 | Reschke et al. |
| 2005/0165390 A1 | 7/2005 | Mauti et al. |
| 2005/0229110 A1 | 10/2005 | Gegner et al. |
| 2005/0251233 A1 | 11/2005 | Kanzius |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0256516 A1 | 11/2006 | Cho |
| 2007/0061393 A1* | 3/2007 | Moore ............... H04L 67/02 709/201 |
| 2007/0076363 A1 | 4/2007 | Liang et al. |
| 2007/0282321 A1 | 12/2007 | Shah et al. |
| 2008/0072896 A1 | 3/2008 | Setzer et al. |
| 2008/0129465 A1 | 6/2008 | Rao |
| 2008/0249377 A1 | 10/2008 | Molducci et al. |
| 2008/0316304 A1 | 12/2008 | Claus et al. |
| 2009/0036884 A1 | 2/2009 | Gregg et al. |
| 2009/0049522 A1 | 2/2009 | Claus et al. |
| 2009/0131929 A1 | 5/2009 | Shimizu |
| 2009/0216091 A1 | 8/2009 | Arndt |
| 2009/0234352 A1 | 9/2009 | Behnke et al. |
| 2010/0036405 A1 | 2/2010 | Giordano et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Sclig |
| 2011/0092972 A1 | 4/2011 | Allen |
| 2011/0093796 A1* | 4/2011 | Plummer ............ G06F 16/24 715/752 |
| 2011/0106567 A1 | 5/2011 | Asher |
| 2011/0125149 A1 | 5/2011 | El-Galley et al. |
| 2011/0130689 A1 | 6/2011 | Cohen et al. |
| 2011/0238063 A1 | 9/2011 | Gregg |
| 2011/0245630 A1 | 10/2011 | St. Pierre et al. |
| 2011/0273465 A1 | 11/2011 | Konishi et al. |
| 2011/0288451 A1 | 11/2011 | Sanai et al. |
| 2011/0306840 A1 | 12/2011 | Allen et al. |
| 2012/0029304 A1 | 2/2012 | Medina et al. |
| 2012/0116380 A1 | 5/2012 | Madan et al. |
| 2012/0132661 A1 | 5/2012 | Gu et al. |
| 2012/0319890 A1 | 12/2012 | McCormack et al. |
| 2013/0031201 A1 | 1/2013 | Kagan et al. |
| 2013/0176220 A1 | 7/2013 | Merschon et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2014/0009894 A1 | 1/2014 | Yu |
| 2014/0058714 A1 | 2/2014 | Boyer |
| 2014/0087573 A1 | 3/2014 | Kroeckel |
| 2014/0108048 A1* | 4/2014 | Cohn ................... G16H 10/60 705/3 |
| 2014/0155721 A1 | 6/2014 | Hauck et al. |
| 2014/0194683 A1 | 7/2014 | Nakaguchi |
| 2014/0226572 A1 | 8/2014 | Thota et al. |
| 2014/0262598 A1 | 9/2014 | Miki et al. |
| 2014/0263552 A1 | 9/2014 | Hall et al. |
| 2014/0378958 A1 | 12/2014 | Leussler |
| 2015/0190189 A1 | 7/2015 | Yates et al. |
| 2015/0272575 A1 | 10/2015 | Leimbach et al. |
| 2015/0289929 A1 | 10/2015 | Toth et al. |
| 2015/0300923 A1 | 10/2015 | Halbert |
| 2015/0334879 A1 | 11/2015 | Fricker |
| 2016/0045247 A1 | 2/2016 | Heim et al. |
| 2016/0058286 A1 | 3/2016 | Joshua et al. |

(56) References Cited

U.S. PATENT DOCUMENTS

| | | |
|---|---|---|
| 2016/0062954 A1 | 3/2016 | Ruff et al. |
| 2016/0074096 A1 | 3/2016 | Lieu |
| 2016/0120591 A1 | 5/2016 | Smith et al. |
| 2016/0199240 A1 | 7/2016 | Newkirk et al. |
| 2016/0225192 A1 | 8/2016 | Jones et al. |
| 2016/0249945 A1 | 9/2016 | Shelton, IV et al. |
| 2016/0287312 A1 | 10/2016 | Tegg et al. |
| 2016/0287337 A1 | 10/2016 | Aram et al. |
| 2017/0000553 A1 | 1/2017 | Wiener et al. |
| 2017/0024978 A1 | 1/2017 | Gulrez et al. |
| 2017/0078455 A1 | 3/2017 | Fisher et al. |
| 2017/0080346 A1* | 3/2017 | Abbas ............... A63F 13/79 |
| 2017/0090507 A1 | 3/2017 | Wiener et al. |
| 2017/0151011 A1 | 6/2017 | Brustad et al. |
| 2017/0189096 A1 | 7/2017 | Danziger et al. |
| 2017/0202595 A1 | 7/2017 | Shelton, IV |
| 2017/0209718 A1 | 7/2017 | Tanis |
| 2017/0251305 A1 | 8/2017 | Fathollahi |
| 2017/0252091 A1 | 9/2017 | Honda |
| 2017/0319259 A1 | 11/2017 | Dunning |
| 2017/0360466 A1 | 12/2017 | Brown et al. |
| 2018/0014872 A1 | 1/2018 | Dickerson |
| 2018/0042659 A1 | 2/2018 | Rupp et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0099161 A1 | 4/2018 | Honda |
| 2018/0166809 A1 | 6/2018 | Brogan et al. |
| 2018/0206909 A1 | 7/2018 | Brustad et al. |
| 2018/0221005 A1 | 8/2018 | Hamel et al. |
| 2018/0221100 A1* | 8/2018 | Berry ............... A61B 34/37 |
| 2018/0228528 A1 | 8/2018 | Fraasch et al. |
| 2018/0262916 A1 | 9/2018 | Polley et al. |
| 2018/0263557 A1 | 9/2018 | Kahlman |
| 2018/0296283 A1 | 10/2018 | Crawford et al. |
| 2018/0333207 A1 | 11/2018 | Moctezuma De la Barrera |
| 2019/0069957 A1 | 3/2019 | Barral et al. |
| 2019/0125455 A1 | 5/2019 | Shelton, IV et al. |
| 2019/0200844 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0201102 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0206563 A1 | 7/2019 | Shelton, IV et al. |
| 2019/0224434 A1 | 7/2019 | Silver et al. |
| 2019/0236840 A1 | 8/2019 | Zuckerman et al. |
| 2019/0247141 A1 | 8/2019 | Batchelor et al. |
| 2019/0278262 A1 | 9/2019 | Taylor et al. |
| 2019/0279524 A1 | 9/2019 | Stoyanov et al. |
| 2019/0348169 A1 | 11/2019 | Gibby et al. |
| 2019/0371012 A1 | 12/2019 | Flexman et al. |
| 2020/0004487 A1 | 1/2020 | Hanajima et al. |
| 2020/0015899 A1 | 1/2020 | Scheib et al. |
| 2020/0015900 A1 | 1/2020 | Scheib et al. |
| 2020/0015907 A1 | 1/2020 | Scheib |
| 2020/0015924 A1 | 1/2020 | Scheib et al. |
| 2020/0030044 A1* | 1/2020 | Wang ............... G16H 20/40 |
| 2020/0038120 A1 | 2/2020 | Ziraknejad et al. |
| 2020/0078071 A1 | 3/2020 | Asher |
| 2020/0078080 A1 | 3/2020 | Henderson et al. |
| 2020/0078083 A1 | 3/2020 | Sprinkle et al. |
| 2020/0078089 A1 | 3/2020 | Henderson et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078117 A1 | 3/2020 | Henderson et al. |
| 2020/0078118 A1 | 3/2020 | Henderson et al. |
| 2020/0078119 A1* | 3/2020 | Henderson ......... A61B 18/1445 |
| 2020/0078120 A1* | 3/2020 | Aldridge ............ H04L 67/10 |
| 2020/0090808 A1 | 3/2020 | Carroll et al. |
| 2020/0100825 A1 | 4/2020 | Henderson et al. |
| 2020/0106220 A1 | 4/2020 | Henderson et al. |
| 2020/0159313 A1 | 5/2020 | Gibby et al. |
| 2020/0237422 A1 | 7/2020 | Canady |
| 2020/0265398 A1 | 8/2020 | Lembo |
| 2020/0268472 A1 | 8/2020 | Wolf et al. |
| 2020/0305924 A1* | 10/2020 | Carroll ............ A61B 17/320092 |
| 2020/0305945 A1 | 10/2020 | Morgan et al. |
| 2020/0342228 A1 | 10/2020 | Prevrhal et al. |
| 2021/0121246 A1 | 4/2021 | Gudalo |
| 2021/0169578 A1 | 6/2021 | Calloway et al. |
| 2021/0196383 A1 | 7/2021 | Shelton, IV et al. |
| 2021/0203889 A1 | 7/2021 | Fung et al. |
| 2021/0212717 A1 | 7/2021 | Yates et al. |
| 2021/0236755 A1 | 8/2021 | King et al. |
| 2021/0264680 A1 | 8/2021 | Cvetko et al. |
| 2021/0385889 A1 | 12/2021 | Patel |
| 2022/0032442 A1 | 2/2022 | Sheffield et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0151704 A1 | 5/2022 | Nikou |
| 2022/0155910 A1 | 5/2022 | Jeong |
| 2022/0261056 A1 | 8/2022 | Motoi et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2023/0027299 A1* | 1/2023 | Xu ..................... H05B 47/17 |
| 2023/0038130 A1 | 2/2023 | Cvetko et al. |
| 2023/0039037 A1 | 2/2023 | Henderson et al. |
| 2023/0069787 A1 | 3/2023 | Henderson et al. |
| 2023/0072423 A1 | 3/2023 | Osborn et al. |

FOREIGN PATENT DOCUMENTS

| | | |
|---|---|---|
| EP | 0929263 B1 | 7/1999 |
| EP | 1006892 B1 | 6/2009 |
| EP | 2942023 A2 | 11/2015 |
| JP | S635457 A | 1/1988 |
| JP | H8280706 A | 10/1996 |
| JP | H1069453 A | 3/1998 |
| JP | 2000089850 A | 3/2000 |
| JP | 2001029353 A | 2/2001 |
| JP | 2006303167 A | 11/2006 |
| WO | WO-0112089 A1 | 2/2001 |
| WO | WO-2008053485 A1 | 5/2008 |
| WO | WO-2014031800 A1 | 2/2014 |
| WO | WO-2014071184 A1 | 5/2014 |
| WO | WO-2015047693 A1 | 4/2015 |
| WO | WO-2017058617 A2 | 4/2017 |

(56) References Cited

FOREIGN PATENT DOCUMENTS

| WO | WO-2018116247 A1 | 6/2018 |
|----|------------------|--------|
| WO | WO-2019215354 A1 | 11/2019 |
| WO | WO 2020/051474 A1 | 3/2020 |
| WO | WO-2021044136 A1 | 3/2021 |

OTHER PUBLICATIONS

IEEE Std 802.Mar. 2012 (Revision of IEEE Std 802.3-2008, published Dec. 28, 2012.

"ATM-MPLS Network Interworking Version 2.0, af-aic-0178.001" ATM Standard, The ATM Forum Technical Committee, published Aug. 2003.

Zhu et al. "Haptic-feedback smart glove as a creative human-machine interface (HMI) for virtual/augmented reality applications," Sci. Adv, vol. 6, No. 19, May 8, 2020.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Li et al., "Wearable Energy Harvesters Generating Electricity From Low-Frequency Human Limb Movement," Microsystems & Nanoengineering (2018), vol. 4(24), 13 pages.

"BOWA ARC 400" Oct. 30, 2018, posted at bowa-medical.com, [site visited Aug. 6, 2021], https://www.bowa-medical.com/tradepro/shopru/artikel/allgemein/BOWA_BRO_11181_ARC400_V2.1_2018_10_30_EN.pdf (Year: 2018).

"Electrosurgical Generator ECONT-0201.3" Mar. 18, 2018, posted at contact-endoscopy.com, [site visited Aug. 6, 2021], https://contact-endoscopy.com/electrosurgical-system (Year: 2018).

International Search Report and Written Opinion dated Sep. 22, 2023 for Application No. PCT/IB2023/056563, 10 pgs.

* cited by examiner

PROFILES FOR MODULAR ENERGY SYSTEM

BACKGROUND

The present disclosure relates to various surgical systems, including modular electrosurgical and/or ultrasonic energy systems. Modular energy systems can be configured to generate a variety of different energy modalities for driving surgical instruments connected thereto. Further, modular energy systems can be configured to allow users to adjust various operational settings related to the energy modalities. Users may have specific preferences related to these adjustable settings, for example, depending on the type of surgical procedure they are performing. Given that modular energy systems can be used to perform multiple types of surgical procedures and can be used by multiple users each having unique preferences, there is a need for devices, systems, and methods for creating, editing, and retrieving operational setting profiles for modular energy systems.

SUMMARY

In various aspects, a method of implementing operational setting profiles for a modular energy system is disclosed. The modular energy system can include an energy module and a display screen configured to render a graphical user interface (GUI). The energy module can include ports configured to deliver energy modalities to surgical instruments coupled thereto. The method can include displaying, by the GUI, a plurality of widgets corresponding to the ports. In one aspect, the plurality of widgets are configured to display information related to operational settings of the modular energy system. The method can further include storing, by a memory accessible by the modular energy system, a plurality of profiles. In one aspect, each of the profiles includes a profile name and a configuration of operational settings implementable by the modular energy system. The method can further include displaying, by the GUI, a profile modal window configured to allow a user to select one or more profiles from the plurality of profiles; implementing, by the modular energy system, the configuration of operational settings of a first profile of the plurality of profiles based on the user selecting the first profile using the profile modal window; and displaying, by the plurality of widgets, information related to the configuration of operational settings of the first profile based on the user selecting the first profile using profile modal window.

In various aspects, a modular energy system for use in a surgical environment is disclosed. The modular energy system can include one or more energy modules, a memory, and a header module. Each of the one or more energy modules can include ports, wherein each of the ports is configured to deliver an energy modality to a surgical instrument connected thereto. The memory can store a plurality of profiles, wherein each profile includes a name and a configuration of operational settings implementable by the modular energy system. The header module can include a display screen, wherein the display screen is configured to render a graphical user interface (GUI). The GUI can be configured to: display a plurality of widgets corresponding to the ports, wherein the plurality of widgets are configured to display information related to operational settings of the modular energy system; display a window configured to allow a user to select from the plurality of profiles comprised in the memory; and populate the widgets with information related to the configuration of operational settings of one of the profiles based on the user selecting the profile.

FIGURES

The various aspects described herein, both as to organization and methods of operation, together with further objects and advantages thereof, may best be understood by reference to the following description, taken in conjunction with the accompanying drawings as follows.

Corresponding reference characters indicate corresponding parts throughout the several views. The exemplifications set out herein illustrate various disclosed aspects, in one form, and such exemplifications are not to be construed as limiting the scope thereof in any manner.

DESCRIPTION

Figure 1:
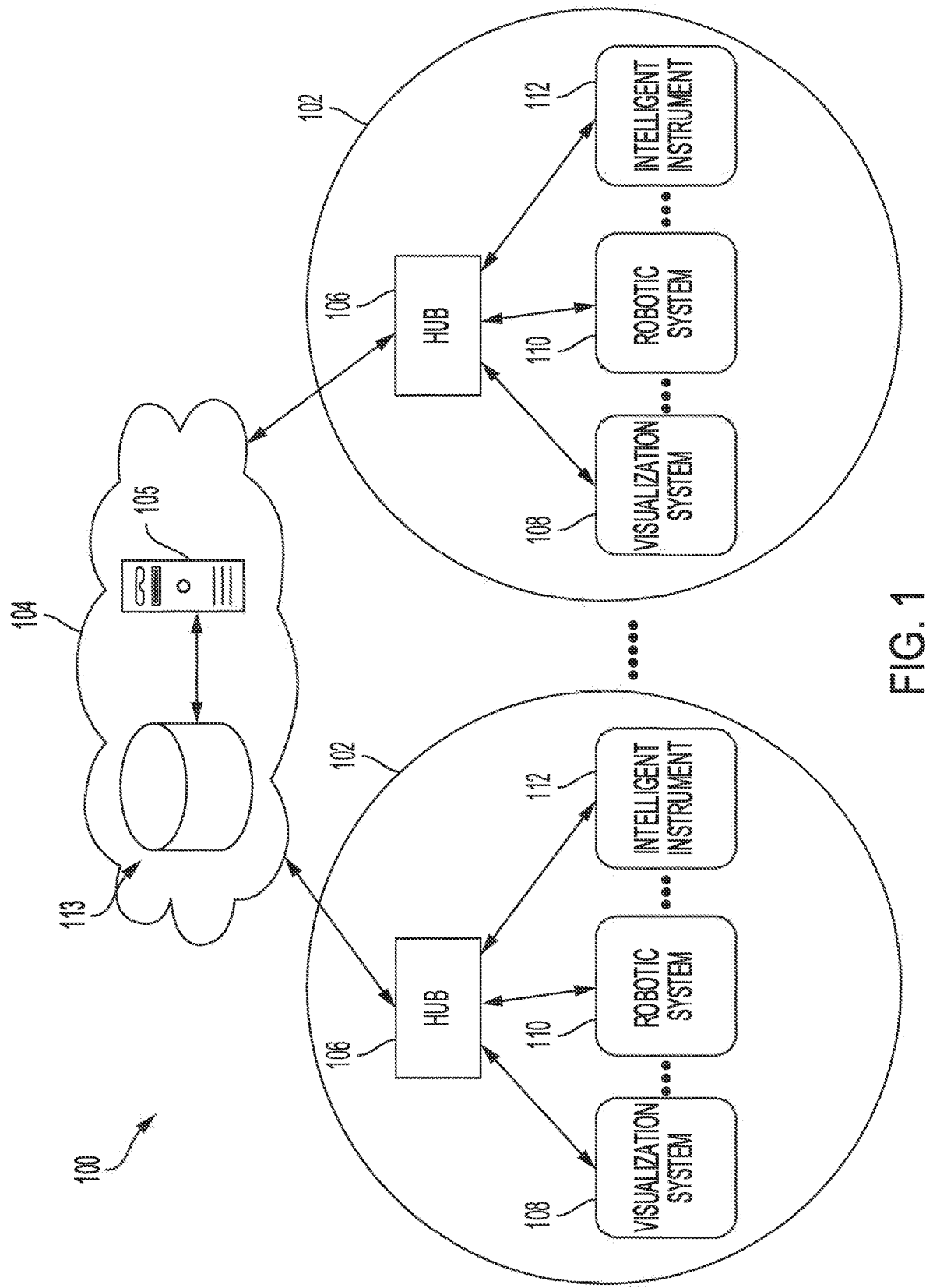
FIG. 1 is a block diagram of a computer-implemented interactive surgical system, in accordance with at least one aspect of the present disclosure.

Applicant of the present application owns the following U.S. patent application filed concurrently herewith, the disclosure of which is herein incorporated by reference in its entirety:

- U.S. patent application Ser. No. 17/851,687, titled SURGICAL FOOTSWITCH ASSIGNMENT FOR MODULAR ENERGY SYSTEM, filed on Jun. 28, 2022, published as U.S. Pub. No. 2023/0414298 on Dec. 28, 2023.

Applicant of the present application owns the following U.S. patent applications filed Mar. 30, 2021, the disclosure of each of which is herein incorporated by reference in its entirety:

- U.S. patent application Ser. No. 17/217,394, titled METHOD FOR MECHANICAL PACKAGING FOR MODULAR ENERGY SYSTEM;
- U.S. patent application Ser. No. 17/217,424, titled METHOD FOR ENERGY DELIVERY FOR MODULAR ENERGY SYSTEM;
- U.S. patent application Ser. No. 17/217,385, titled METHOD FOR INTELLIGENT INSTRUMENTS FOR MODULAR ENERGY SYSTEM; and
- U.S. patent application Ser. No. 17/217,405, titled METHOD FOR SYSTEM ARCHITECTURE FOR MODULAR ENERGY SYSTEM.

Applicant of the present application owns the following U.S. patent applications filed Sep. 5, 2019, the disclosure of each of which is herein incorporated by reference in its entirety:

- U.S. patent application Ser. No. 16/562,144, titled METHOD FOR CONTROLLING A MODULAR ENERGY SYSTEM USER INTERFACE, now U.S. Patent Application Publication No. 2020/0078106;
- U.S. patent application Ser. No. 16/562,151, titled PASSIVE HEADER MODULE FOR A MODULAR ENERGY SYSTEM, now U.S. Patent Application Publication No. 2020/0078110;
- U.S. patent application Ser. No. 16/562,157, titled CONSOLIDATED USER INTERFACE FOR MODULAR ENERGY SYSTEM, now U.S. Patent Application Publication No. 2020/0081585;
- U.S. patent application Ser. No. 16/562,159, titled AUDIO TONE CONSTRUCTION FOR AN ENERGY MODULE OF A MODULAR ENERGY SYSTEM, now U.S. Patent Application Publication No. 2020/0314569;
- U.S. patent application Ser. No. 16/562,163, titled ADAPTABLY CONNECTABLE AND REASSIGNABLE SYSTEM ACCESSORIES FOR MODULAR ENERGY SYSTEM, now U.S. Patent Application Publication No. 2020/0078111;
- U.S. patent application Ser. No. 16/562,123, titled METHOD FOR CONSTRUCTING AND USING A MODULAR SURGICAL ENERGY SYSTEM WITH MULTIPLE DEVICES, now U.S. Patent Application Publication No. 2020/0100830;
- U.S. patent application Ser. No. 16/562,135, titled METHOD FOR CONTROLLING AN ENERGY MODULE OUTPUT, now U.S. Patent Application Publication No. 2020/0078076;
- U.S. patent application Ser. No. 16/562,180, titled ENERGY MODULE FOR DRIVING MULTIPLE ENERGY MODALITIES, now U.S. Patent Application Publication No. 2020/0078080;
- U.S. patent application Ser. No. 16/562,184, titled GROUNDING ARRANGEMENT OF ENERGY MODULES, now U.S. Patent Application Publication No. 2020/0078081;
- U.S. patent application Ser. No. 16/562,188, titled BACKPLANE CONNECTOR DESIGN TO CONNECT STACKED ENERGY MODULES, now U.S. Patent Application Publication No. 2020/0078116;
- U.S. patent application Ser. No. 16/562,195, titled ENERGY MODULE FOR DRIVING MULTIPLE ENERGY MODALITIES THROUGH A PORT, now U.S. Patent Application Publication No. 2020/0078117;
- U.S. patent application Ser. No. 16/562,202 titled SURGICAL INSTRUMENT UTILIZING DRIVE SIGNAL TO POWER SECONDARY FUNCTION, now U.S. Patent Application Publication No. 2020/0078082;
- U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;
- U.S. patent application Ser. No. 16/562,169, titled SURGICAL MODULAR ENERGY SYSTEM WITH A SEGMENTED BACKPLANE, now U.S. Patent Application Publication No. 2020/0078112;
- U.S. patent application Ser. No. 16/562,185, titled SURGICAL MODULAR ENERGY SYSTEM WITH FOOTER MODULE, now U.S. Patent Application Publication No. 2020/0078115;
- U.S. patent application Ser. No. 16/562,203, titled POWER AND COMMUNICATION MITIGATION ARRANGEMENT FOR MODULAR SURGICAL ENERGY SYSTEM, now U.S. Patent Application Publication No. 2020/0078118;
- U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;
- U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;
- U.S. patent application Ser. No. 16/562,243, titled MODULAR SURGICAL ENERGY SYSTEM WITH MODULE POSITIONAL AWARENESS WITH DIGITAL LOGIC, now U.S. Patent Application Publication No. 2020/0078120;
- U.S. patent application Ser. No. 16/562,125, titled METHOD FOR COMMUNICATING BETWEEN MODULES AND DEVICES IN A MODULAR SURGICAL SYSTEM, now U.S. Patent Application Publication No. 2020/0100825;

U.S. patent application Ser. No. 16/562,137, titled FLEXIBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEXIBLE NEUTRAL ELECTRODE, now U.S. Patent Application Publication No. 2020/0078077;

U.S. patent application Ser. No. 16/562,154, titled SMART RETURN PAD SENSING THROUGH MODULATION OF NEAR FIELD COMMUNICATION AND CONTACT QUALITY MONITORING SIGNALS, now U.S. Patent Application Publication No. 2020/0078089;

U.S. patent application Ser. No. 16/562,162, titled AUTOMATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPARATE BUT CONNECTED MODULES, now U.S. Patent Application Publication No. 2020/0078078;

U.S. patent application Ser. No. 16/562,170, titled MANAGING SIMULTANEOUS MONOPOLAR OUTPUTS USING DUTY CYCLE AND SYNCHRONIZATION, now U.S. Patent Application Publication No. 2020/0078079;

U.S. patent application Ser. No. 16/562,172, titled PORT PRESENCE DETECTION SYSTEM FOR MODULAR ENERGY SYSTEM, now U.S. Patent Application Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPONENTS OF A MODULAR ENERGY SYSTEM, now U.S. Patent Application Publication No. 2020/0078114;

U.S. Design patent application Ser. No. 29/704,610, titled ENERGY MODULE;

U.S. Design patent application Ser. No. 29/704,614, titled ENERGY MODULE MONOPOLAR PORT WITH FOURTH SOCKET AMONG THREE OTHER SOCKETS;

U.S. Design patent application Ser. No. 29/704,616, titled BACKPLANE CONNECTOR FOR ENERGY MODULE; and U.S. Design patent application Ser. No. 29/704,617, titled ALERT SCREEN FOR ENERGY MODULE.

Applicant of the present application owns the following U.S. Patent Provisional Applications filed Mar. 29, 2019, the disclosure of each of which is herein incorporated by reference in its entirety:

U.S. Provisional Patent Application Ser. No. 62/826,584, titled MODULAR SURGICAL PLATFORM ELECTRICAL ARCHITECTURE;

U.S. Provisional Patent Application Ser. No. 62/826,587, titled MODULAR ENERGY SYSTEM CONNECTIVITY;

U.S. Provisional Patent Application Ser. No. 62/826,588, titled MODULAR ENERGY SYSTEM INSTRUMENT COMMUNICATION TECHNIQUES; and U.S. Provisional Patent Application Ser. No. 62/826,592, titled MODULAR ENERGY DELIVERY SYSTEM.

Applicant of the present application owns the following U.S. Patent Provisional Application filed Sep. 7, 2018, the disclosure of which is herein incorporated by reference in its entirety:

U.S. Provisional Patent Application Ser. No. 62/728,480, titled MODULAR ENERGY SYSTEM AND USER INTERFACE.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
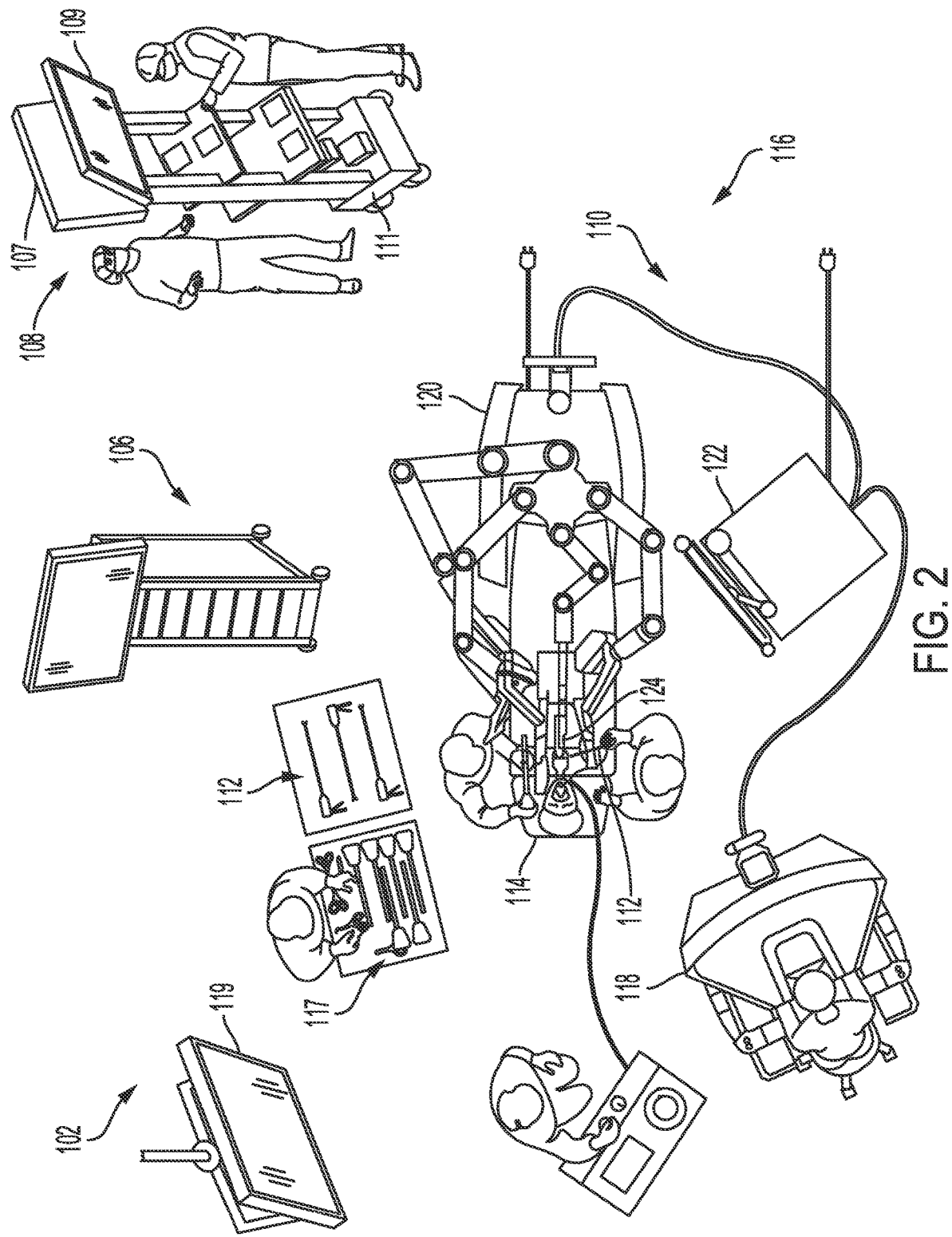
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
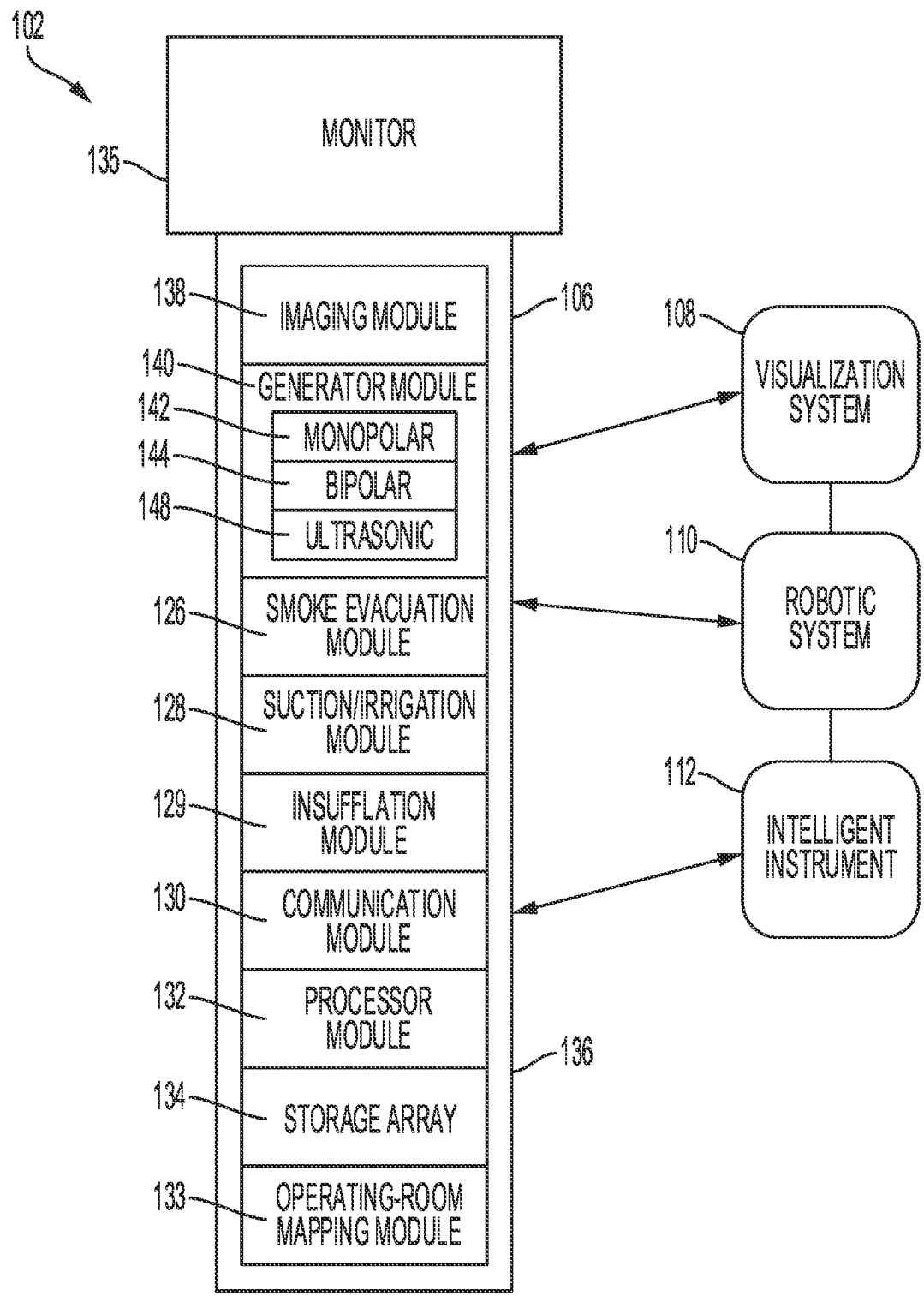
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. In some aspects, the visualization system 108 may be a separable piece of equipment. In alternative aspects, the visualization system 108 could be contained within the hub 106 as a functional module. The hub 106 includes a hub display 135, an imaging module 138, a generator module 140, a communication module 130, a processor module 132, a storage array 134, and an operating room mapping module 133. In certain aspects, as illustrated in FIG. 3, the hub 106 further includes a smoke evacuation module 126, a suction/irrigation module 128, and/or an insufflation module 129. In certain aspects, any of the modules in the hub 106 may be combined with each other into a single module.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes one or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts. In one aspect, the first energy-generator module is slidably movable into an electrical engagement with the power and data contacts and wherein the first energy-generator module is slidably movable out of the electrical engagement with the first power and data contacts. In an alternative aspect, the first energy-generator module is stackably movable into an electrical engagement with the power and data contacts and wherein the first energy-generator module is stackably movable out of the electrical engagement with the first power and data contacts.

Further to the above, the modular surgical enclosure also includes a second energy-generator module configured to generate a second energy, either the same or different than the first energy, for application to the tissue, and a second docking station comprising a second docking port that includes second data and power contacts. In one aspect, the second energy-generator module is slidably movable into an electrical engagement with the power and data contacts, and wherein the second energy-generator module is slidably movable out of the electrical engagement with the second power and data contacts. In an alternative aspect, the second energy-generator module is stackably movable into an electrical engagement with the power and data contacts, and wherein the second energy-generator module is stackably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, a suction/irrigation module 128, and an insufflation module 129. The hub modular enclosure 136 further facilitates interactive communication between the modules 140, 126, 128, 129. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128, 129 and interactive communication therebetween.

Generator Hardware

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 4:
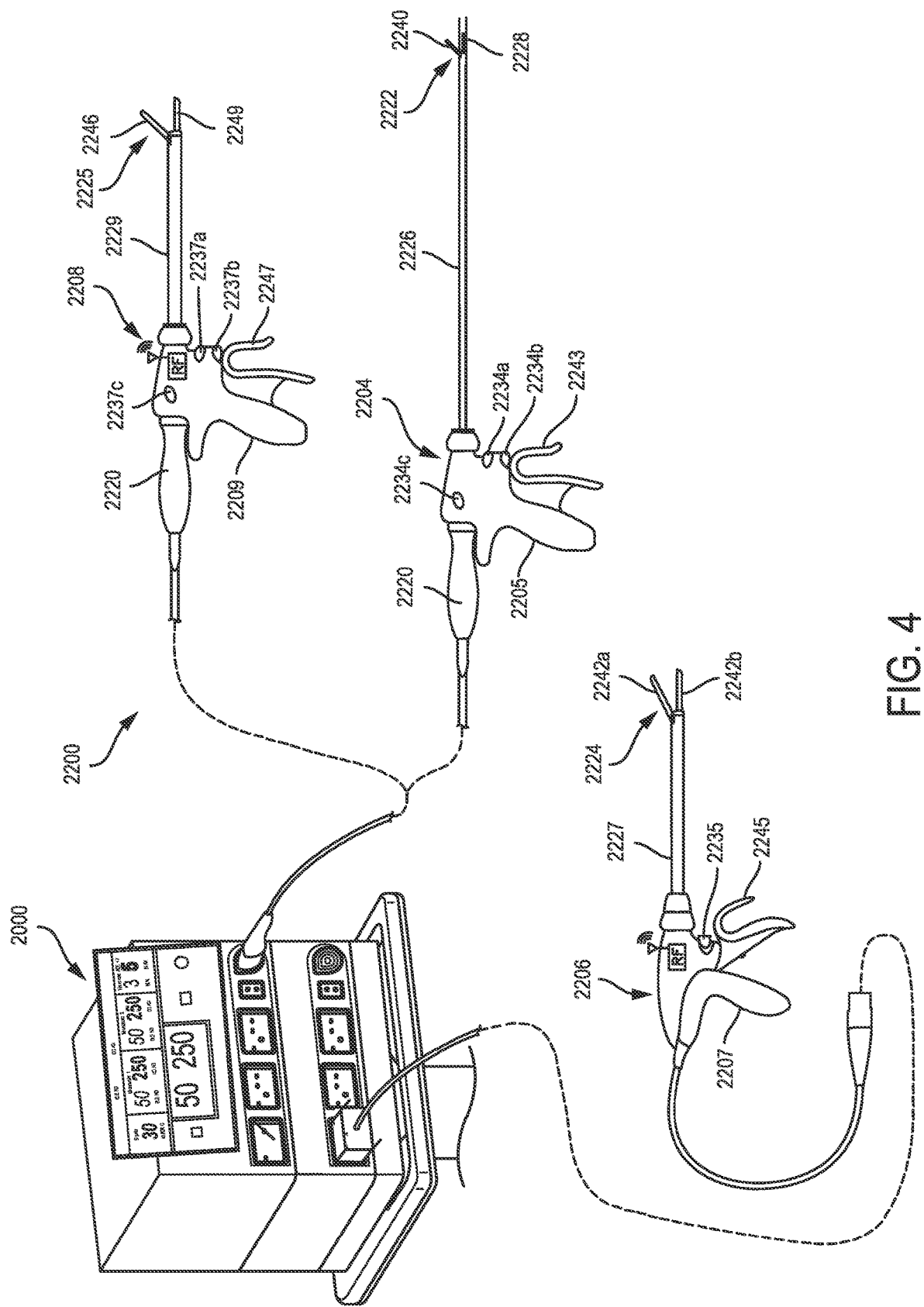
FIG. 4 is a surgical system comprising a generator and various surgical instruments usable therewith, in accordance with at least one aspect of the present disclosure.

FIG. 4 illustrates one form of a surgical system 2200 comprising a modular energy system 2000 and various surgical instruments 2204, 2206, 2208 usable therewith, where the surgical instrument 2204 is an ultrasonic surgical instrument, the surgical instrument 2206 is an RF electrosurgical instrument, and the multifunction surgical instrument 2208 is a combination ultrasonic/RF electrosurgical instrument. The modular energy system 2000 is configurable for use with a variety of surgical instruments. According to various forms, the modular energy system 2000 may be configurable for use with different surgical instruments of different types including, for example, ultrasonic surgical instruments 2204, RF electrosurgical instruments 2206, and multifunction surgical instruments 2208 that integrate RF and ultrasonic energies delivered individually or simultaneously from the modular energy system 2000. Although in the form of FIG. 4 the modular energy system 2000 is shown separate from the surgical instruments 2204, 2206, 2208 in one form, the modular energy system 2000 may be formed integrally with any of the surgical instruments 2204, 2206, 2208 to form a unitary surgical system. The modular energy system 2000 may be configured for wired or wireless communication.

The modular energy system 2000 is configured to drive multiple surgical instruments 2204, 2206, 2208. The first surgical instrument is an ultrasonic surgical instrument 2204 and comprises a handpiece 2205 (HP), an ultrasonic transducer 2220, a shaft 2226, and an end effector 2222. The end effector 2222 comprises an ultrasonic blade 2228 acoustically coupled to the ultrasonic transducer 2220 and a clamp arm 2240. The handpiece 2205 comprises a trigger 2243 to operate the clamp arm 2240 and a combination of the toggle buttons 2234a, 2234b, 2234c to energize and drive the ultrasonic blade 2228 or other function. The toggle buttons 2234a, 2234b, 2234c can be configured to energize the ultrasonic transducer 2220 with the modular energy system 2000.

The modular energy system 2000 also is configured to drive a second surgical instrument 2206. The second surgical instrument 2206 is an RF electrosurgical instrument and comprises a handpiece 2207 (HP), a shaft 2227, and an end effector 2224. The end effector 2224 comprises electrodes in clamp arms 2242a, 2242b and return through an electrical conductor portion of the shaft 2227. The electrodes are coupled to and energized by a bipolar energy source within the modular energy system 2000. The handpiece 2207 comprises a trigger 2245 to operate the clamp arms 2242a, 2242b and an energy button 2235 to actuate an energy switch to energize the electrodes in the end effector 2224.

The modular energy system 2000 also is configured to drive a multifunction surgical instrument 2208. The multifunction surgical instrument 2208 comprises a handpiece 2209 (HP), a shaft 2229, and an end effector 2225. The end effector 2225 comprises an ultrasonic blade 2249 and a clamp arm 2246. The ultrasonic blade 2249 is acoustically coupled to the ultrasonic transducer 2220. The ultrasonic transducer 2220 may be separable from or integral to the handpiece 2209. The handpiece 2209 comprises a trigger 2247 to operate the clamp arm 2246 and a combination of the toggle buttons 2237a, 2237b, 2237c to energize and drive the ultrasonic blade 2249 or other function. The toggle buttons 2237a, 2237b, 2237c can be configured to energize the ultrasonic transducer 2220 with the modular energy system 2000 and energize the ultrasonic blade 2249 with a bipolar energy source also contained within the modular energy system 2000.

The modular energy system 2000 is configurable for use with a variety of surgical instruments. According to various forms, the modular energy system 2000 may be configurable for use with different surgical instruments of different types including, for example, the ultrasonic surgical instrument 2204, the RF electrosurgical instrument 2206, and the multifunction surgical instrument 2208 that integrates RF and ultrasonic energies delivered individually or simultaneously from the modular energy system 2000. Although in the form of FIG. 4 the modular energy system 2000 is shown separate from the surgical instruments 2204, 2206, 2208, in another form the modular energy system 2000 may be formed integrally with any one of the surgical instruments 2204, 2206, 2208 to form a unitary surgical system. Further aspects of generators for digitally generating electrical signal waveforms and surgical instruments are described in U.S. Patent Application Publication No. 2017/0086914, which is herein incorporated by reference in its entirety.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-3, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 5-8. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIG. 3. The modular energy system 2000 can also include a variety of different components or accessories that are also connectable to or otherwise associatable with the modules 2001. In another aspect, the modular energy system 2000 can be embodied as a generator module 140 (FIG. 3) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 5:
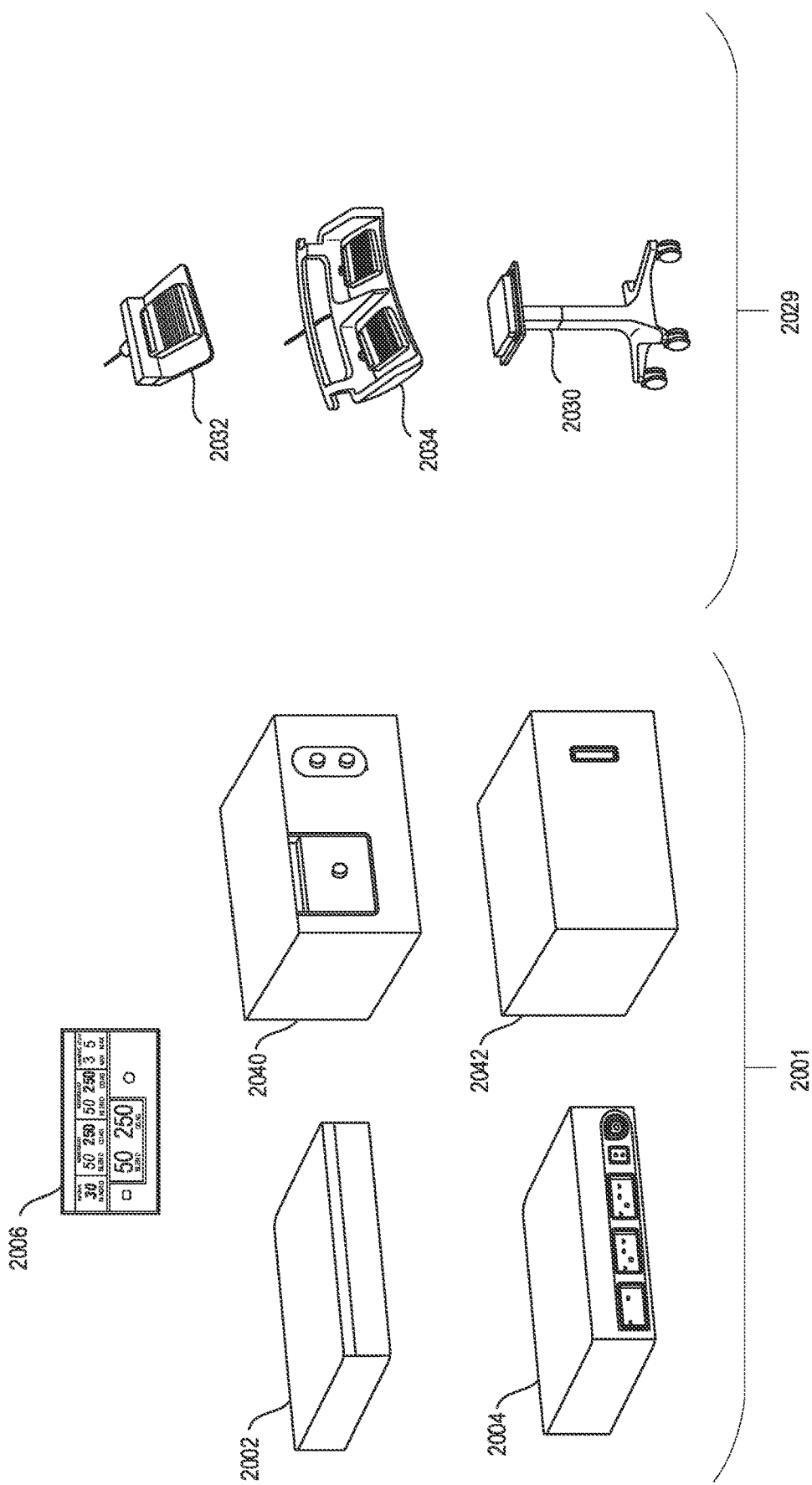
FIG. 5 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 5. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140 (FIG. 3), can be configured to generate one or multiple energy modalities for driving electrosurgical and/or ultrasonic surgical instruments connected thereto. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-3.

Figure 6B:
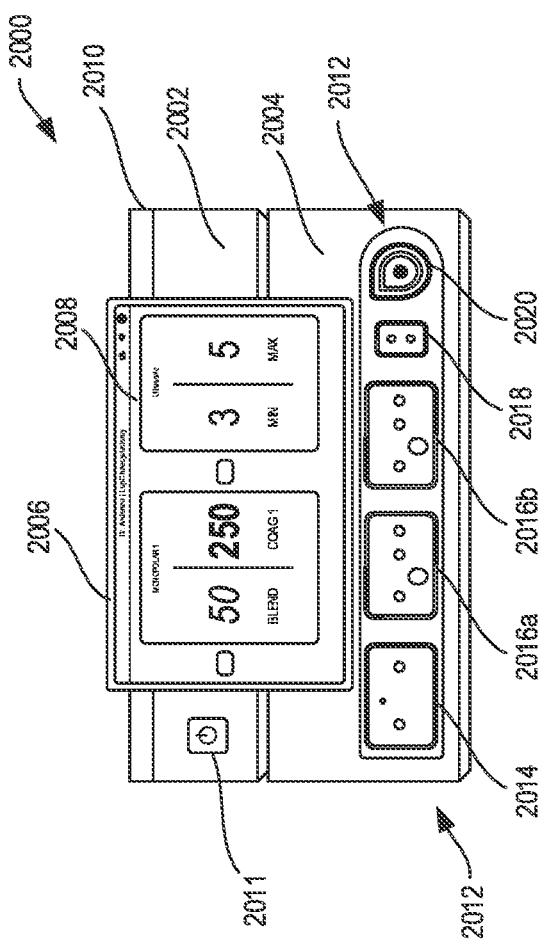
FIG. 6B is the modular energy system shown in FIG. 6A mounted to a cart, in accordance with at least one aspect of the present disclosure.
Figure 6A:
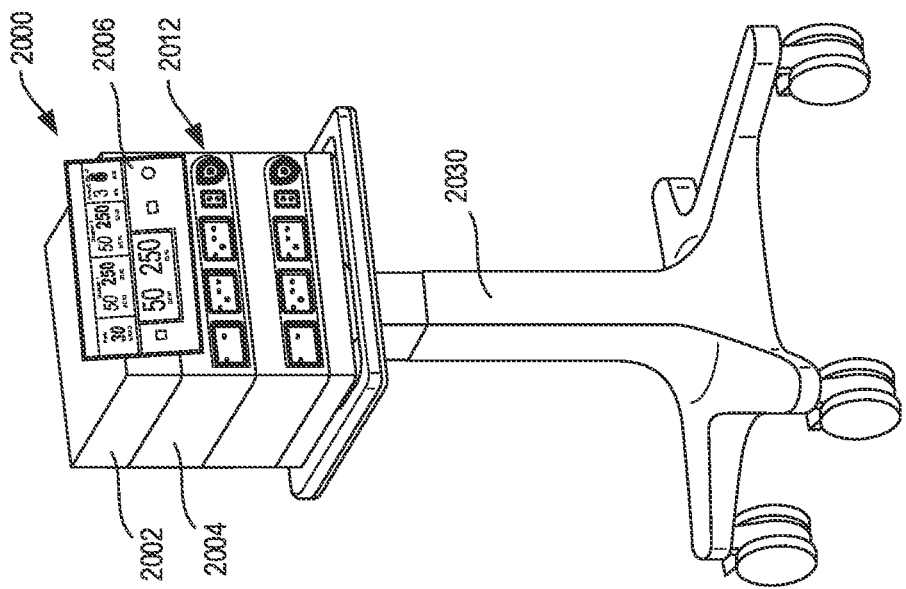
FIG. 6A is a first illustrative modular energy system configuration including a header module and a display screen that renders a graphical user interface (GUI) for relaying information regarding modules connected to the header module, in accordance with at least one aspect of the present disclosure.

Referring now to FIG. 6A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 8. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 6A, the energy module 2004 can include a port assembly 2012 including a number of different ports configured to deliver different energy modalities to corresponding surgical instruments that are connectable thereto. In the particular aspect illustrated in FIGS. 5-8, the port assembly 2012 includes a bipolar port 2014, a first monopolar port 2016*a*, a second monopolar port 2016*b*, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 6A and 6B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 7:
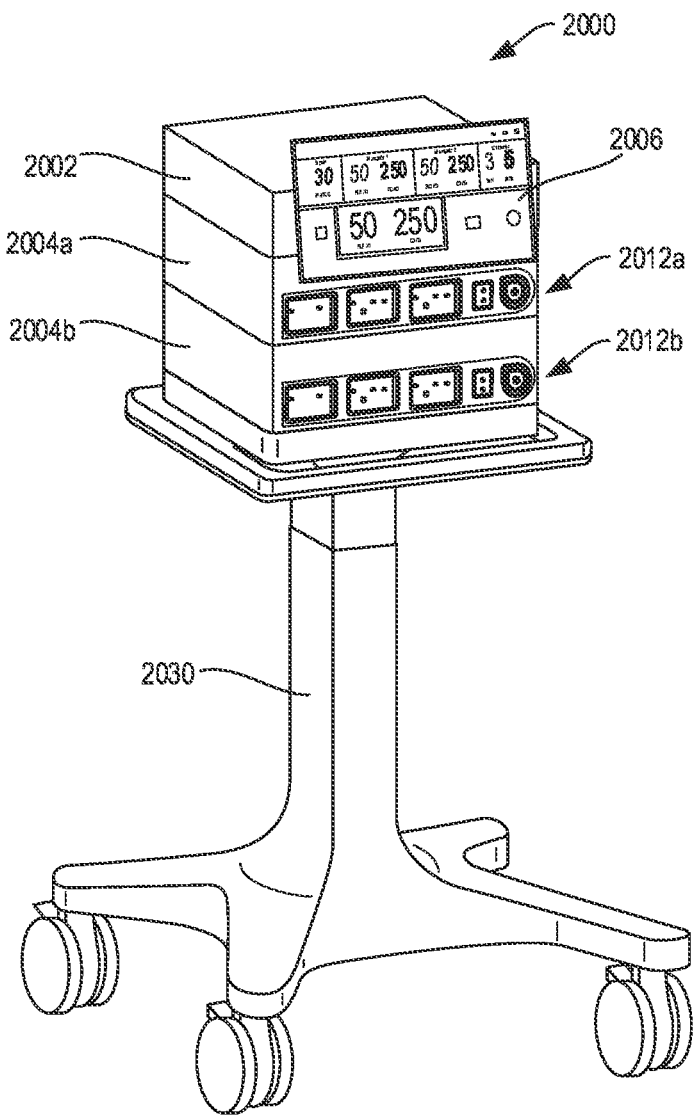
FIG. 7 is a second illustrative modular energy system configuration including a header module, a display screen, an energy module, and an expanded energy module connected together and mounted to a cart, in accordance with at least one aspect of the present disclosure.

FIG. 7 illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures.

It should be noted that the configurations illustrated in FIGS. 6A-7 and described above are provided simply to illustrate the various concepts of the modular energy system 2000 and should not be interpreted to limit the modular energy system 2000 to the particular aforementioned configurations.

Figure 8:
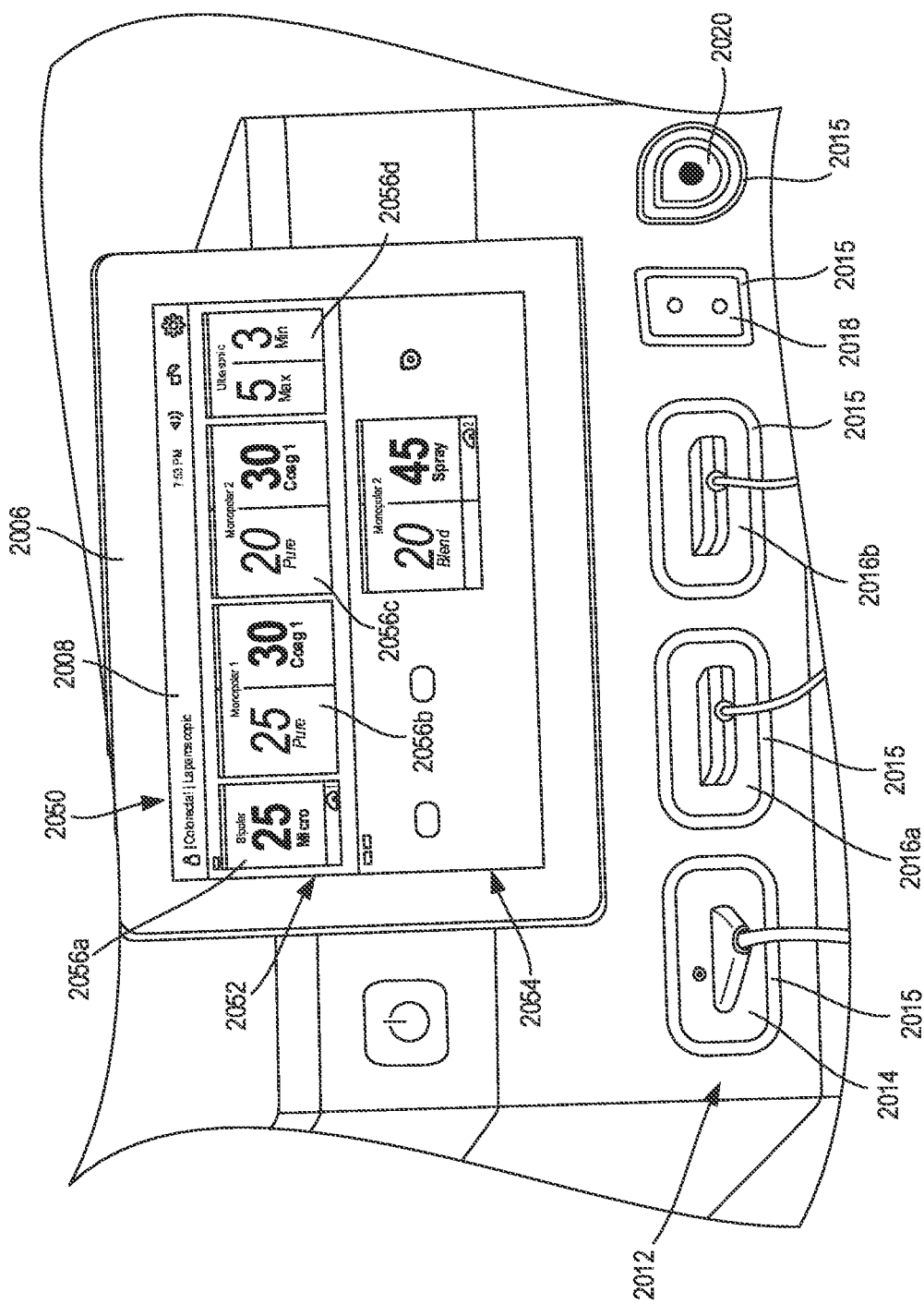
FIG. 8 is a perspective view of a header module of a modular energy system including a user interface, in accordance with at least one aspect of the present disclosure.

Referring now to FIG. 8, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 12, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056a corresponding to the bipolar port 2014, a second widget 2056b corresponding to the first monopolar port 2016a, a third widget 2056c corresponding to the second monopolar port 2016b, and a fourth widget 2056d corresponding to the combination energy port 2020. Each of these widgets 2056a-d provides data related to its corresponding port of the port assembly 2012 and controls for controlling the modes and other features of the energy modality delivered by the energy module 2004 through the respective port of the port assembly 2012. For example, the widgets 2056a-d can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the application of power to each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 9:
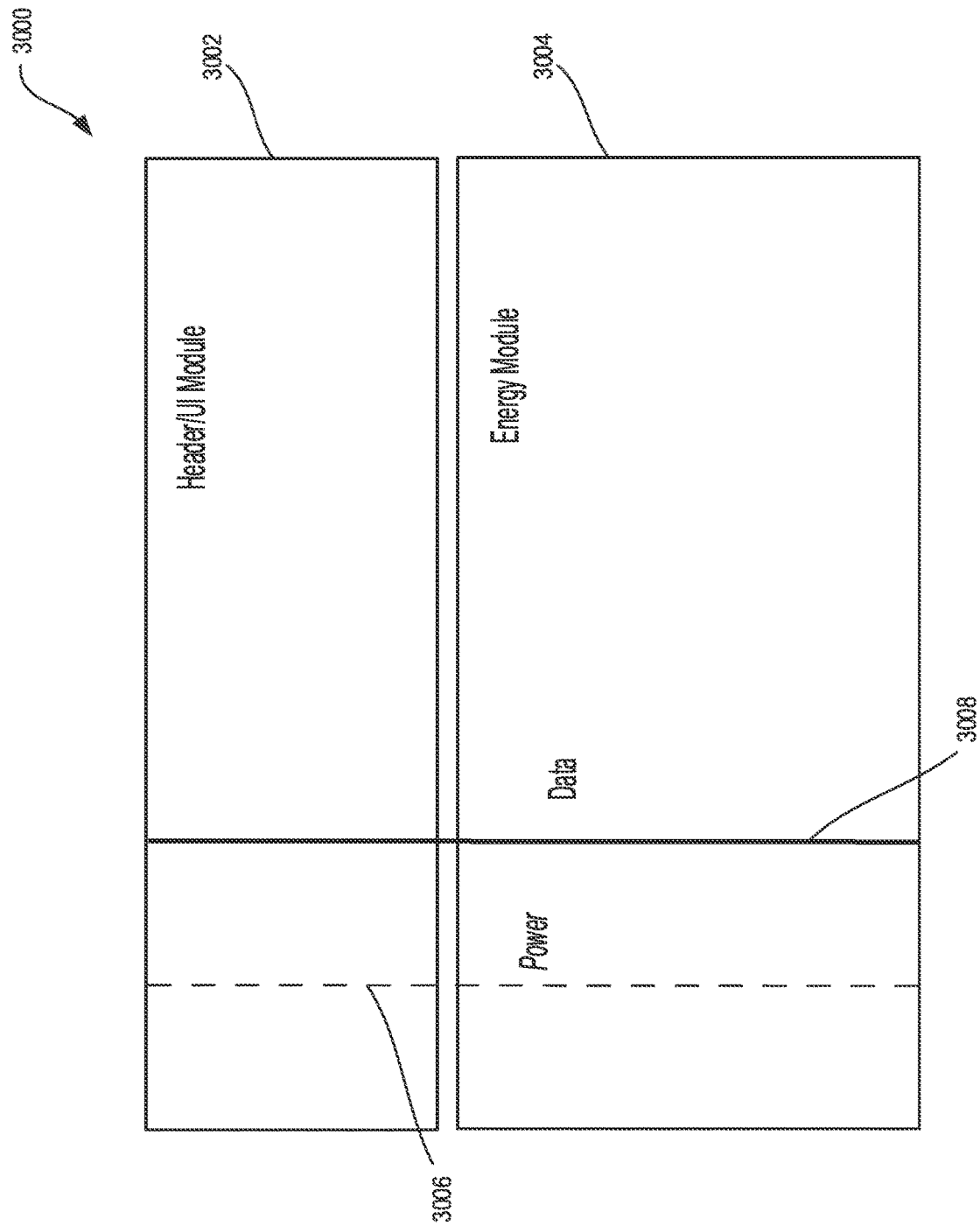
FIG. 9 is a block diagram of a stand-alone hub configuration of a modular energy system, in accordance with at least one aspect of the present disclosure.
Figure 10:
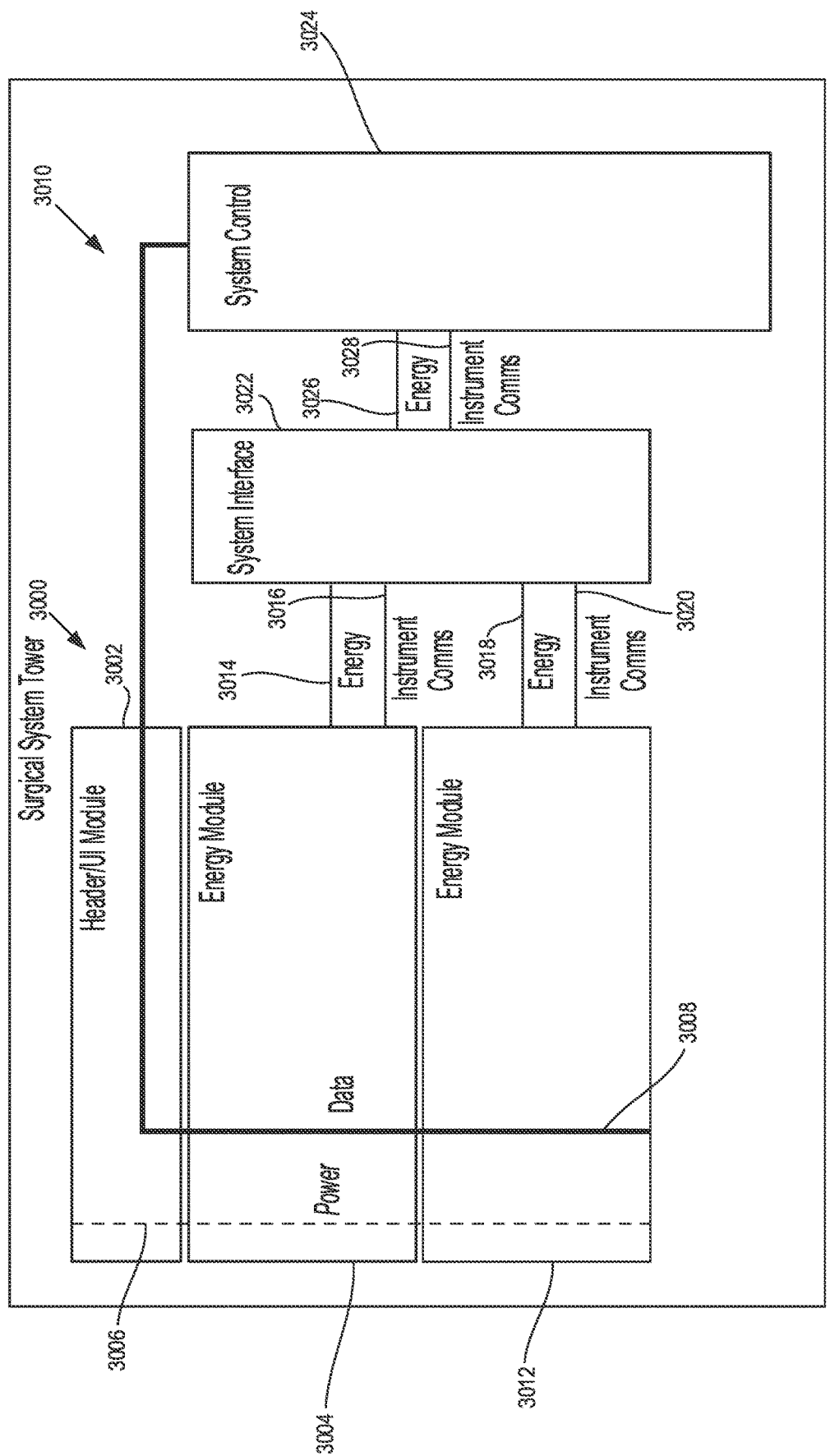
FIG. 10 is a block diagram of a hub configuration of a modular energy system integrated with a surgical control system, in accordance with at least one aspect of the present disclosure.

FIG. 9 is a block diagram of a stand-alone hub configuration of a modular energy system 3000, in accordance with at least one aspect of the present disclosure and FIG. 10 is a block diagram of a hub configuration of a modular energy system 3000 integrated with a surgical control system 3010, in accordance with at least one aspect of the present disclosure. As depicted in FIGS. 9 and 10, the modular energy system 3000 can be either utilized as stand-alone units or integrated with a surgical control system 3010 that controls and/or receives data from one or more surgical hub units. In the examples illustrated in FIGS. 9 and 10, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 9, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 10, a surgical hub configuration includes a modular energy system 3000 integrated with a control system 3010 and an interface system 3022 for managing, among other things, data and power transmission to and/or from the modular energy system 3000. The modular energy system depicted in FIG. 10 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

The energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

In one aspect, with reference to FIGS. 9 and 10, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 9 and 10, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled or disconnected, and set to a high impedance state.

In one aspect, with reference to FIGS. 9 and 10, the modules of the modular energy system 3000 can include a pulse/stimulation/auxiliary amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

As described in greater detail herein, a modular energy system comprises a header module and one or more functional or surgical modules. In various instances, the modular energy system is a modular energy system. In various instances, the surgical modules include energy modules, communication modules, user interface modules; however, the surgical modules are envisioned to be any suitable type of functional or surgical module for use with the modular energy system.

Modular energy system offers many advantages in a surgical procedure, as described above in connection with the modular energy systems 2000 (FIGS. 5-8), 3000 (FIGS. 9-10). However, cable management and setup/teardown time can be a significant deterrent. Various aspects of the present disclosure provide a modular energy system with a single power cable and a single power switch to control startup and shutdown of the entire modular energy system, which obviated the need to individually activate and deactivate each individual module from which the modular energy system is constructed. Also, various aspects of the present disclosure provide a modular energy system with power management schemes that facilitate a safe and, in some instances, concurrent delivery of power to the modules of a modular energy system.

Figure 11:
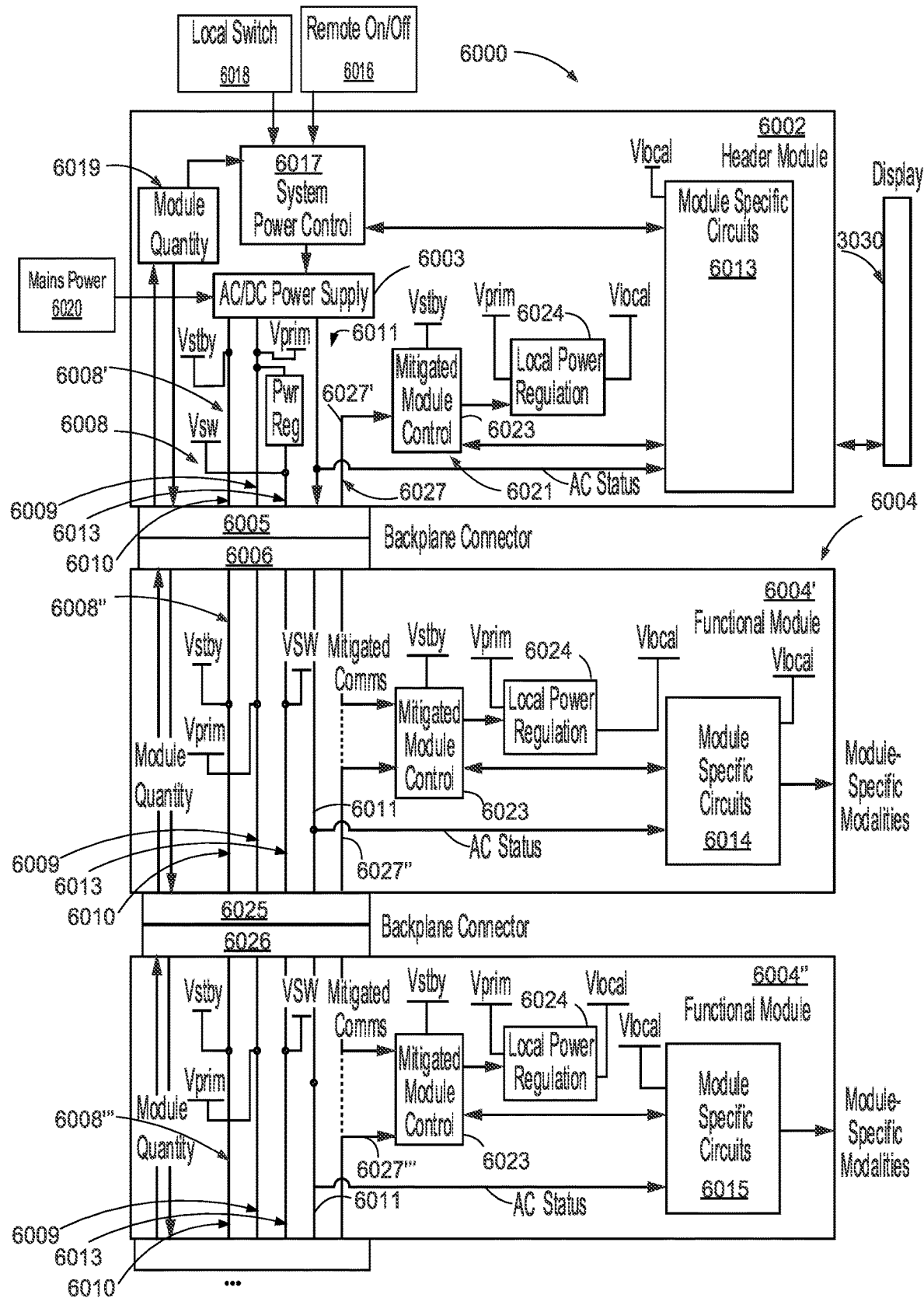
FIG. 11 is a schematic diagram of a modular energy system stack illustrating a power backplane, in accordance with at least one aspect of the present disclosure.

In various aspects, as illustrated in FIG. 11, a modular energy system 6000 that is similar in many respects to the modular energy systems 2000 (FIGS. 5-8), 3000 (FIGS. 9-10). For the sake of brevity, various details of the modular energy system 6000, which are similar to the modular energy system 2000 and/or the modular energy system 3000, are not repeated herein.

The modular energy system 6000 comprises a header module 6002 and an "N" number of surgical modules 6004, where "N" is an integer greater than or equal to one. In various examples, the modular energy system 6000 includes a UI module such as, for example, the UI module 3030 and/or a communication module such as, for example, the communication module 3032. Furthermore, pass-through hub connectors couple individual modules to one another in a stack configuration. In the example of FIG. 11, the header module 6002 is coupled to a surgical module 6004 via pass-through hub connectors 6005, 6006.

The modular energy system 6000 comprises an example power architecture that consists of a single AC/DC power supply 6003 that provides power to all the surgical modules in the stack. The AC/DC power supply 6003 is housed in the header module 6002, and utilizes a power backplane 6008 to distribute power to each module in the stack. The example of FIG. 11 demonstrates three separate power domains on the power backplane 6008: a primary power domain 6009, a standby power domain 6010, and an Ethernet switch power domain 6013.

In the example illustrated in FIG. 11, the power backplane 6008 extends from the header module 6002 through a number of intermediate modules 6004 to a most bottom, or farthest, module in the stack. In various aspects, the power backplane 6008 is configured to deliver power to a surgical module 6004 through one or more other surgical modules 6004 that are ahead of it in the stack. The surgical module 6004 receiving power from the header module 6002 can be coupled to a surgical instrument or tool configured to deliver therapeutic energy to a patient.

The primary power domain 6009 is the primary power source for the functional module-specific circuits 6013, 6014, 6015 of the modules 6002, 6004. It consists of a single voltage rail that is provided to every module. In at least one example, a nominal voltage of 60V can be selected to be higher than the local rails needed by any module, so that the modules can exclusively implement buck regulation, which is generally more efficient than boost regulation.

In various aspects, the primary power domain 6009 is controlled by the header module 6002. In certain instances, as illustrated in FIG. 11, a local power switch 6018 is positioned on the header module 6002. In certain instances, a remote on/off interface 6016 can be configured to control a system power control 6017 on the header module 6002, for example. In at least one example, the remote on/off interface 6016 is configured to transmit pulsed discrete commands (separate commands for On and Off) and a power status telemetry signal. In various instances, the primary power domain 6009 is configured to distribute power to all the modules in the stack configuration following a user-initiated power-up.

In various aspects, as illustrated in FIG. 11, the modules of the modular energy system 6000 can be communicably coupled to the header module 6002 and/or to each other via a communication (Serial bus/Ethernet) interface 6040 such that data or other information is shared by and between the modules of which the modular energy system is constructed. An Ethernet switch domain 6013 can be derived from the primary power domain 6009, for example. The Ethernet switch power domain 6013 is segregated into a separate power domain, which is configured to power Ethernet switches within each of the modules in the stack configuration, so that the primary communications interface 6040 will remain alive when local power to a module is removed. In at least one example, the primary communication interface 6040 comprises a 1000BASE-T Ethernet network, where each module represents a node on the network, and each module downstream from the header module 6002 contains a 3-port Ethernet switch for routing traffic to the local module or passing the data up or downstream as appropriate.

Furthermore, in certain examples, the modular energy system 6000 includes secondary, low speed, communication interface between modules for critical, power related functions including module power sequencing and module power status. The secondary communications interface can, for example, be a multi-drop Local Interconnect Network (LIN), where the header module is the master and all downstream modules are slaves.

In various aspects, as illustrated in FIG. 11, a standby power domain 6010 is a separate output from the AC/DC power supply 6003 that is always live when the supply is connected to mains power 6020. The standby power domain 6010 is used by all the modules in the system to power circuitry for a mitigated communications interface, and to control the local power to each module. Further, the standby power domain 6010 is configured to provide power to circuitry that is critical in a standby mode such as, for example, on/off command detection, status LEDs, secondary communication bus, etc.

In various aspects, as illustrated in FIG. 11, the individual surgical modules 6004 lack independent power supplies and, as such, rely on the header module 6002 to supply power in the stack configuration. Only the header module 6002 is directly connected to the mains power 6020. The surgical modules 6004 lack direct connections to the mains power 6020, and can receive power only in the stack configuration. This arrangement improves the safety of the individual surgical modules 6004, and reduces the overall footprint of the modular energy system 6000. This arrangement further reduces the number of cords required for proper operation of the modular energy system 6000, which can reduce clutter and footprint in the operating room.

Accordingly, a surgical instrument connected to surgical modules 6004 of a modular energy system 6000, in the stack configuration, receives therapeutic energy for tissue treatment that is generated by the surgical module 6004 from power delivered to the surgical module 6004 from the AC/DC power supply 6003 of the header module 6002.

In at least one example, while a header module 6002 is assembled in a stack configuration with a first surgical module 6004', energy can flow from the AC/DC power supply 6003 to the first surgical module 6004'. Further, while a header module 6002 is assembled in a stack configuration with a first surgical module 6004' (connected to the header module 6002) and a second surgical module 6004" (connected to the first surgical module 6004'), energy can flow from the AC/DC power supply 6003 to the second surgical module 6004" through the first surgical module 6004'.

The energy generated by the AC/DC power supply 6003 of the header module 6002 is transmitted through a segmented power backplane 6008 defined through the modular energy system 6000. In the example of FIG. 11, the header module 6002 houses a power backplane segment 6008', the first surgical module 6004' houses a power backplane segment 6008", and the second surgical module 6004" houses a power backplane segment 6008'". The power backplane segment 6008' is detachably coupled to the power backplane segment 6008" in the stack configuration. Further, the power backplane 6008" is detachably coupled to the power backplane segment 6008'" in the stack configuration. Accordingly, energy flows from the AC/DC power supply 6003 to the power backplane segment 6008', then to the power backplane segment 6008", and then to the power backplane segment 6008'".

In the example of FIG. 11, the power backplane segment 6008' is detachably connected to the power backplane segment 6008" via pass-through hub connectors 6005, 6006 in the stack configuration. Further, the power backplane segment 6008″ is detachably connected to the power backplane segment 6008‴ via pass-through hub connectors 6025, 6056 in the stack configuration. In certain instances, removing a surgical module from the stack configuration severs its connection to the power supply 6003. For example, separating the second surgical module 6004″ from the first surgical module 6004′ disconnects the power backplane segment 6008‴ from the power backplane segment 6008″. However, the connection between the power backplane segment 6008″ and the power backplane segment 6008‴ remains intact as long as the header module 6002 and the first surgical module 6004′ remain in the stack configuration. Accordingly, energy can still flow to the first surgical module 6004′ after disconnecting the second surgical module 6004″ through the connection between the header module 6002 and the first surgical module 6004′. Separating connected modules can be achieved, in certain instances, by simply pulling the surgical modules 6004 apart.

In the example of FIG. 11, each of the modules 6002, 6004 includes a mitigated module control 6023. The mitigated module controls 6023 are coupled to corresponding local power regulation modules 6024 that are configured to regulate power based on input from the mitigated module controls 6023. In certain aspects, the mitigated module controls 6023 allow the header module 6002 to independently control the local power regulation modules 6024.

The modular energy system 6000 further includes a mitigated communications interface 6021 that includes a segmented communication backplane 6027 extending between the mitigated module controls 6023. The segmented communication backplane 6027 is similar in many respects to the segmented power backplane 6008. Mitigated Communication between the mitigated module controls 6023 of the header module 6002 and the surgical modules 6004 can be achieved through the segmented communication backplane 6027 defined through the modular energy system 6000. In the example of FIG. 11, the header module 6002 houses a communication backplane segment 6027′, the first surgical module 6004′ houses a communication backplane segment 6027″, and the second surgical module 6004″ houses a communication backplane segment 6027‴. The communication backplane segment 6027′ is detachably coupled to the communication backplane segment 6027″ in the stack configuration via the pass-through hub connectors 6005, 6006. Further, the communication backplane segment 6027″ is detachably coupled to the communication backplane segment 6027‴ in the stack configuration via the pass-through hub connectors 6025, 6026.

Although the example of FIG. 11 depicts a modular energy system 6000 includes a header module 6002 and two surgical modules 6004′ 6004″, this is not limiting. Modular energy systems with more or less surgical modules are contemplated by the present disclosure. In some aspects, the modular energy system 6000 includes other modules such as, for example, a communications module. In some aspects, the header module 6502 supports a display screen such as, for example, the display 2006 (FIG. 6A) that renders a GUI such as, for example, the GUI 2008 for relaying information regarding the modules connected to the header module 6002. The GUI 2008 of the display screen 2006 can provide a consolidated point of control all of the modules making up the particular configuration of a modular energy system.

Figure 12:
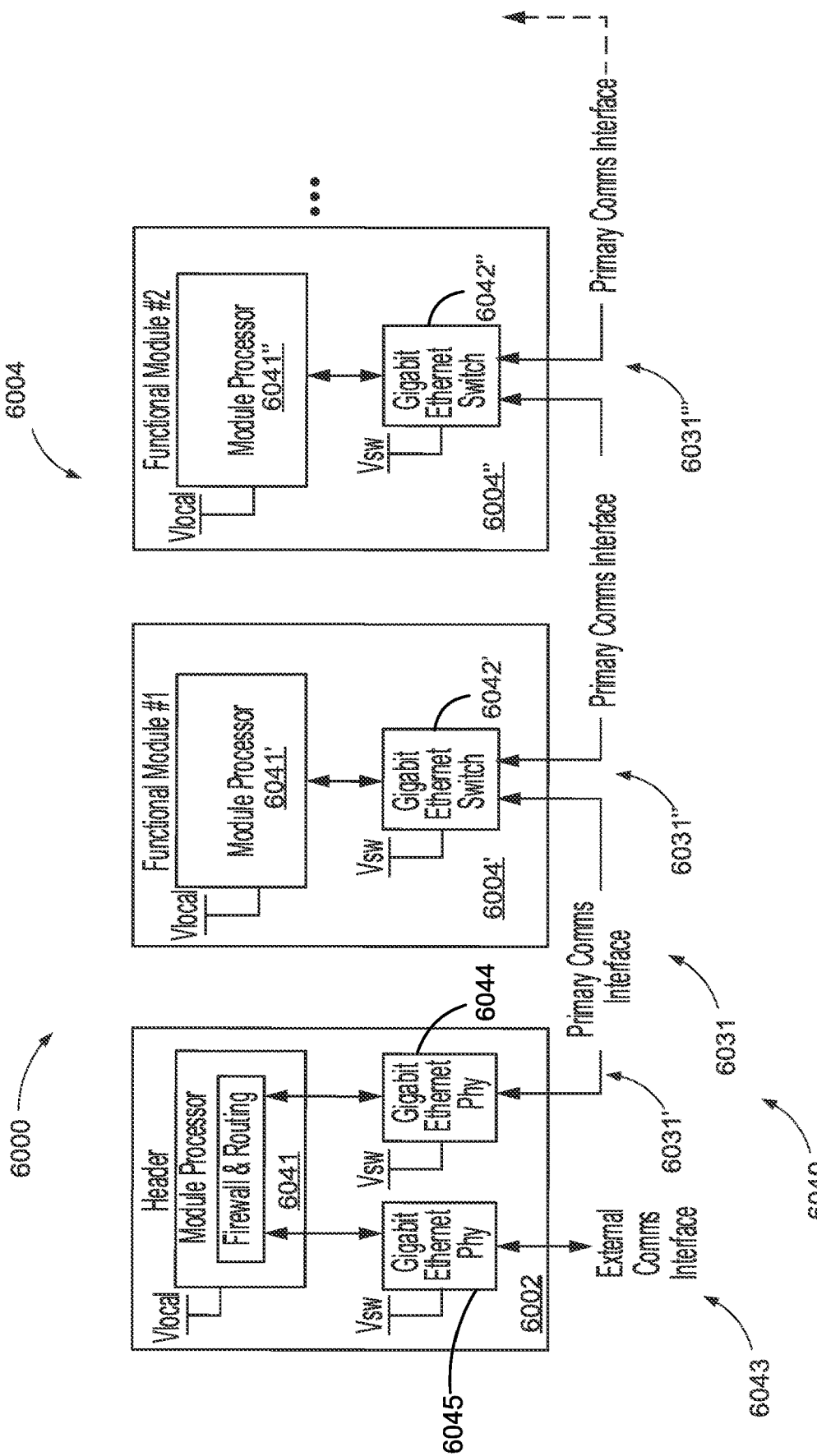
FIG. 12 is a schematic diagram of a modular energy system, in accordance with at least one aspect of the present disclosure.

FIG. 12 depicts a simplified schematic diagram of the modular energy system 6000, which illustrates a primary communications interface 6040 between the header module 6002 and the surgical modules 6004. The primary communications interface 6040 communicably connects module processors 6041, 6041′, 6041″ of the header module 6002 and the surgical modules 6004. Commands generated by the module processor 6041 of the header module are transmitted downstream to a desired functional surgical module via the primary communications interface 6040. In certain instances, the primary communications interface 6040 is configured to establish a two-way communication pathway between neighboring modules. In other instances, the primary communications interface 6040 is configured to establish a one-way communication pathway between neighboring modules.

Furthermore, the primary communications interface 6040 includes a segmented communication backplane 6031, which is similar in many respects to the segmented power backplane 6008. Communication between the header module 6002 and the surgical modules 6004 can be achieved through the segmented communication backplane 6031 defined through the modular energy system 6000. In the example of FIG. 12, the header module 6002 houses a communication backplane segment 6031′, the first surgical module 6004′ houses a communication backplane segment 6031″, and the second surgical module 6004″ houses a communication backplane segment 6031‴. The communication backplane segment 6031′ is detachably coupled to the communication backplane segment 6031″ in the stack configuration via the pass-through hub connectors 6005, 6006. Further, the communication backplane 6031″ is detachably coupled to the communication backplane segment 6031″ in the stack configuration via the pass-through hub connectors 6025, 6026.

Figure 16:
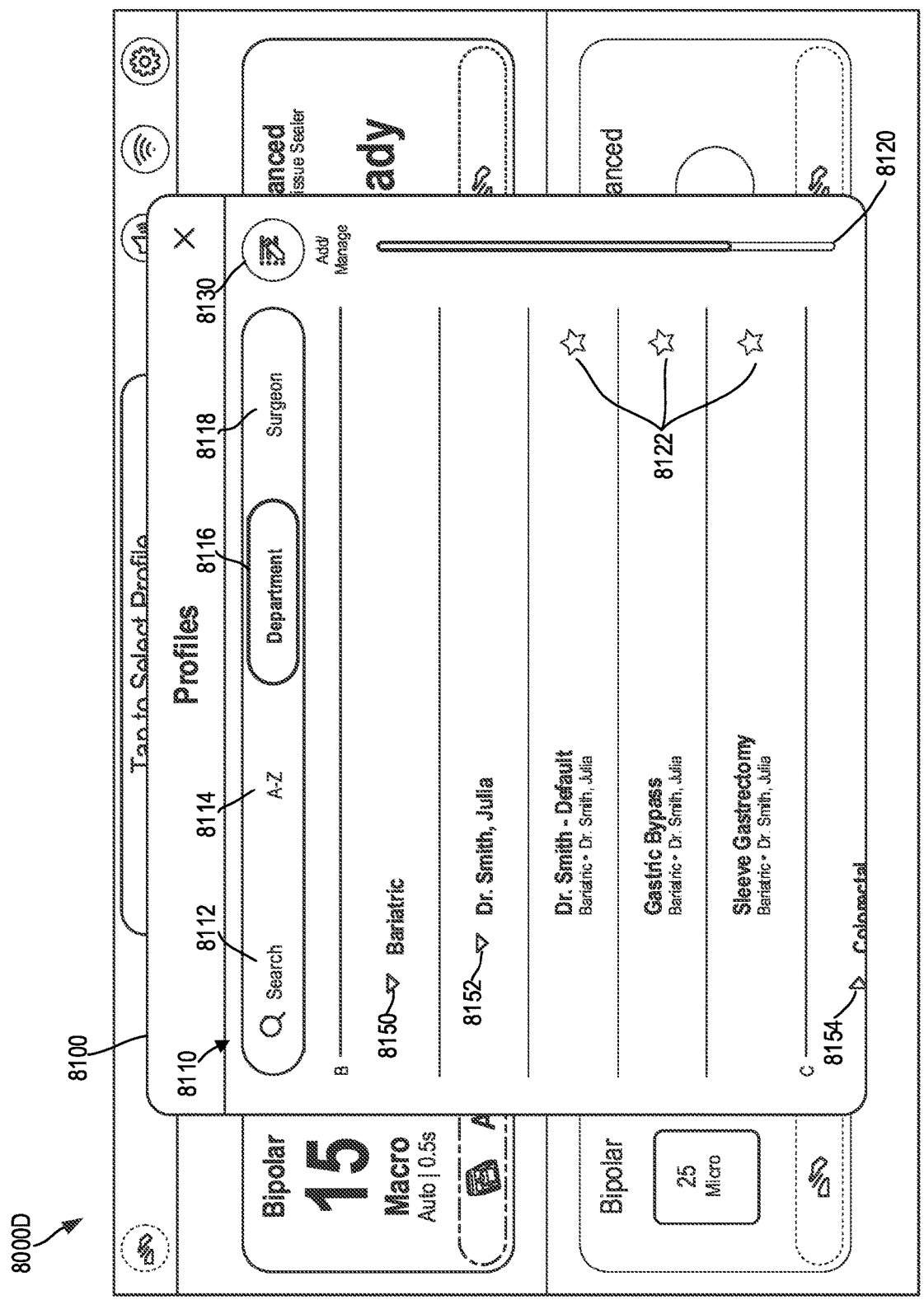

In at least one example, as illustrated in FIG. 12, the primary communications interface 6040 is implemented using the DDS framework running on a Gigabit Ethernet interface. The module processors 6041, 6041′, 6041″ are connected to Gigabit Ethernet Phy 6044, and Gigabit Ethernet Switches 6042′, 6042″. In the example of FIG. 16, the segmented communication backplane 6031 connects the Gigabit Ethernet Phy 6044 and the Gigabit Ethernet Switches 6042 of the neighboring modules.

In various aspects, as illustrated in FIG. 12, the header module 6002 includes a separate Gigabit Ethernet Phy 6045 for an external communications interface 6043 with the processor module 6041 of the header module 6002. In at least one example, the processor module 6041 of the header module 6002 handles firewalls and information routing.

Referring to FIG. 11, the AC/DC power supply 6003 may provide an AC Status signal 6011 that indicates a loss of AC power supplied by the AC/DC power supply 6003. The AC status signal 6011 can be provided to all the modules of the modular energy system 6000 via the segmented power backplane 6008 to allow each module as much time as possible for a graceful shutdown, before primary output power is lost. The AC status signal 6011 is received by the module specific circuits 6013, 6014, 6015, for example. In various examples, the system power control 6017 can be configured to detect AC power loss. In at least one example, the AC power loss is detected via one or more suitable sensors.

Referring to FIGS. 11 and 12, to ensure that a local power failure in one of the modules of the modular energy system 6000 does not disable the entire power bus, the primary power input to all modules can be fused or a similar method of current limiting can be used (e-fuse, circuit breaker, etc.). Further, Ethernet switch power is segregated into a separate power domain 6013 so that the primary communications interface 6040 remains alive when local power to a module is removed. In other words, primary power can be removed and/or diverted from a surgical module without losing its ability to communicate with other surgical modules 6004 and/or the header module 6002.

Settings Profiles for Modular Energy System

Having described a general implementation of modular energy systems 2000, 3000, 6000 and graphical user interface (GUI) 2008, the disclosure now turns to describe various implementations of other modular energy systems and GUIs. The other modular energy systems are substantially similar to the modular energy system 2000, the modular energy system 3000, and/or the modular energy system 6000. Likewise, the other GUIs are substantially similar to GUI 2008. For the sake of brevity, various details of the other modular energy systems and GUIs described in the following sections are not repeated herein. Any aspect of the other modular energy systems and GUIs described below can be brought into the modular energy system 2000, the modular energy system 3000, the modular energy system 6000, and the GUI 2008.

As discussed above in reference to FIG. 8, modular energy systems can include a display screen (e.g., display screen 2006) configured for displaying a GUI (e.g., GUI 2008). The GUI can be used to control various settings related to the operation of the modular energy system. For example, GUI 2008 includes widgets 2056a-d corresponding to the respective ports of the port assembly 2012 and the energy modalities delivered therethrough. By interacting with the widgets 2056a-d, a user can adjust settings such as power levels, modes, and other features of the energy modalities.

Users of the modular energy system may prefer different settings depending on the type of procedure they are performing. For example, referring still to FIG. 8, GUI 2008 may be displaying a particular surgeon's preferred settings for performing a laparoscopic colorectal procedure. These preferred settings can include having the bipolar energy modality of the first energy module set at a power level of 25 and the mode set to "Micro," as shown in widget 2056a. These preferred settings can also include the various power levels, modes, and other settings shown in the other widgets 2056b-c. The same surgeon may prefer different energy modality power level and/or mode settings when performing a different type of surgical procedure. Likewise, a different surgeon performing the same laparoscopic colorectal procedure may prefer different energy modality power level and/or mode settings.

Rather than requiring users to manually adjust the modular energy system to their preferred settings every time they prepare for a procedure, it may be advantageous to allow users to save and later retrieve their preferred settings. For example, allowing a user to save and later retrieve settings used to perform a particular type of procedure can enable the user to perform the procedure with more consistency. As another example, a user may find a particular configuration of power levels and modes to be especially suited for performing a specific type of procedure. Allowing the user to save and later retrieve settings can help to ensure that the particular configuration of power levels and modes are not forgotten by the user. As yet another example, retrieving saved settings can allow for reduced setup times when preparing to perform a procedure. Accordingly, the present disclosure provides devices, systems, and methods for creating, editing, and retrieving operational setting profiles for modular energy systems using a GUI. As used herein a "profile" can refer to a particular configuration of operational settings of a modular energy system, such as a configuration of active ports, energy levels, energy modes, and other settings related to the energy modalities of a modular energy system.

FIGS. 13-45 depict various illustrative GUI screens 8000A-JJ (collectively GUI 8000) that can be used to create, edit, and/or retrieve modular energy system profiles, according to several non-limiting aspects of the present disclosure. GUI 8000 can be rendered by a display screen of a modular energy system. For example, similar to the GUI 2008, GUI 8000 can be rendered by display screen 2006 of the modular energy system 2000 referenced above with respect to FIGS. 5-8. Although FIGS. 13-45 depict a GUI rendered by modular energy systems having specific configurations of modules and ports, those of ordinary skill in the art will appreciate that the aspects disclosed below with respect to FIGS. 13-45 can be applied to modular energy systems having a variety of different module and port configurations. Additionally, it should be noted the GUI screens 8000A-JJ of GUI 8000 are provided for illustrative purposes. Any combination of GUI screens 8000A-JJ can be used to implement GUI 8000 and the various aspects described herein.

Figure 13:
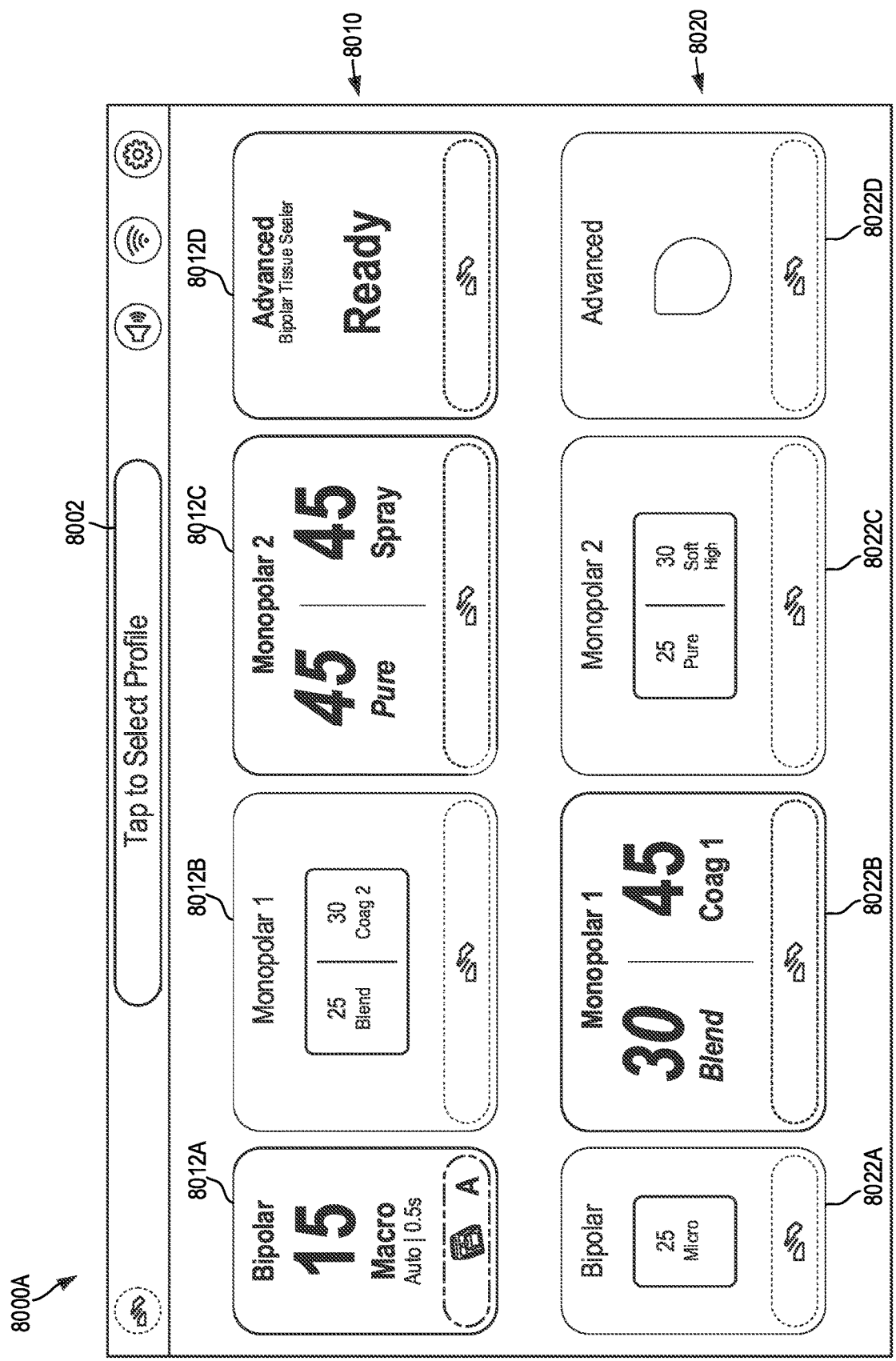
FIGS. 13-18 are illustrative graphical user interface screens for retrieving profiles, in accordance with several aspects of the present disclosure.

FIGS. 13-18 are illustrative graphical user interface screens 8000A-F for retrieving profiles, in accordance with several aspects of the present disclosure. Referring now to FIG. 13, GUI screen 8000A is shown displaying data and controls related to an illustrative modular energy system configured with a first energy module and a second energy module (e.g., similar to modular energy system 2000 of FIG. 7, which includes a first energy module 2004a and a second energy module 2004b). Specifically, GUI screen 8000A includes a first portion 8010 corresponding to the first energy module and a second portion 8020 corresponding to the second energy module.

The first portion 8010 of GUI screen 8000A includes a first widget 8012A, a second widget 8012B, a third widget 8012C, and a fourth widget 8012D each displaying data and controls that respectively correspond to a bipolar port, a first monopolar port, a second monopolar port, and a combination energy port of the first energy module (e.g., bipolar port 2014, first monopolar port 2016a, second monopolar port 2016b, and combination energy port 2020 of energy module 2004 of FIG. 6A). Likewise, the second portion 8020 of GUI screen 8000A includes a first widget 8022A, a second widget 8022B, a third widget 8022C, and a fourth widget 8022D each displaying data and controls that respectively correspond to a bipolar port, a first monopolar port, a second monopolar port, and a combination energy port of the second energy module. As discuss further below, a user can tap on any of the widgets 8012A-D, 8022A-D to adjust various settings of the energy modalities delivered through the corresponding ports. As noted above, as different and/or additional modules are connected to the modular energy system stack, the GUI 8000 can adjust to accommodate the different and/or additional controls for the updated modular energy system configuration.

According to the non-limiting aspect of FIG. 13, the information included in widgets 8012A, 8012C, 8012D, and 8022B is displayed in a larger, bold font whereas the information included in widgets 8012B, 8022A, 8022C, and 8022D is displayed in a smaller font. In some aspects, the larger font included in 8012A, 8012C, 8012D, and 8022B indicates that the ports corresponding to these widgets have a surgical instrument connected thereto or are otherwise available for use. Likewise, in other aspects, the smaller font included in widgets 8012B, 8022A, 8022C, and 8022D indicates that the ports corresponding to these widgets do not have a surgical instrument connected thereto or are otherwise unavailable for use.

Still referring to FIG. 13, the GUI screen 8000A includes a profile bar 8002. The profile bar 8002 is a GUI element that can include various buttons, icons, and/or text related to creating, editing, and/or retrieving profiles. GUI screen 8000A may be a default screen implemented by GUI 8000 when a profile is not currently being implemented by the modular energy system. Accordingly, the profile bar 8002 displayed by GUI screen 8000A may include text indicating that a profile is not currently being implemented and/or may include text instructing the user to select a profile. According to the non-limiting aspect of FIG. 13, the profile bar 8002 includes the text "Tap to Select Profile."

Figure 14:
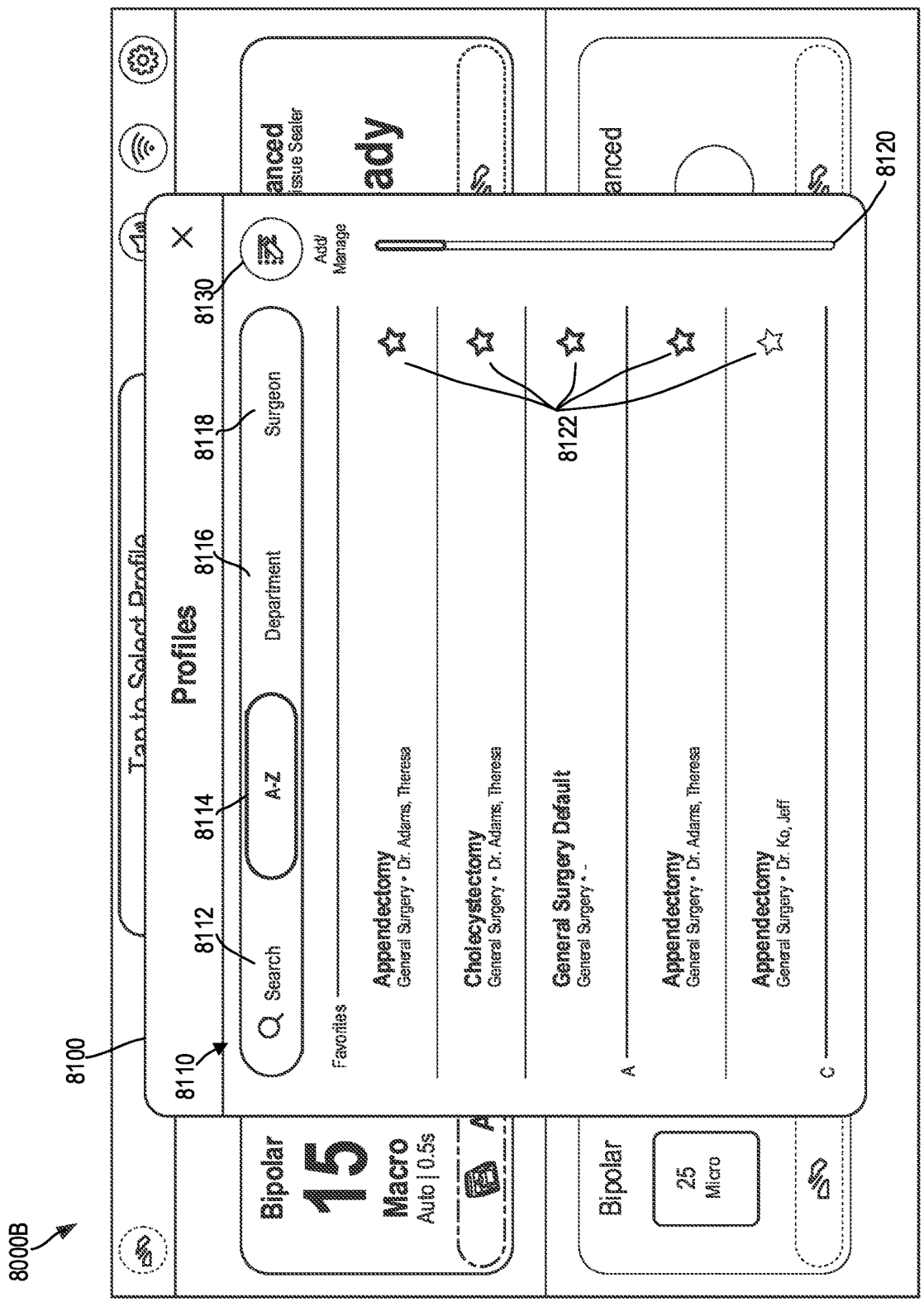

Transitioning from GUI screen 8000A to GUI screen 8000B of FIG. 14, tapping or otherwise selecting the profile bar 8002 can cause GUI 8000 to display a profile modal window 8100. The profile modal window 8100 includes an add/manage button 8130 (discussed more below with respect to FIG. 19) and navigation bar 8110 that can be used to locate existing profiles. The existing profiles may be profiles that have been previously created and stored in memory accessible by modular energy system, such as memory of a header module of the modular energy system, memory of a surgical system comprising the modular energy system (e.g., storage array 134 of the surgical system 102 of FIG. 3), and/or memory of a cloud-based storage device communicably coupled to the modular energy system (e.g., storage device 105 of the cloud 104 of FIG. 1). The navigation bar 8110 includes a search bar 8112, an alphabetical tab 8114, a department tab 8116, and a surgeon tab 8118 that a user can select to search and/or locate the existing profiles, as explained below.

Sill referring to FIG. 14, GUI screen 8000B shows that the alphabetical tab 8114 is selected. In some aspects, the alphabetical tab 8114 may be the default tab that is selected when the profile modal window 8100 is opened. As a result of the alphabetical tab 8114 being selected, the names of the existing profiles are arranged under the navigation bar 8110 in ascending alphabetical order. As explained in detail below, profiles may be associated with a particular department and/or a particular surgeon. Thus, in some aspects, the name of the department and/or surgeon associated with each profile may be listed under each of the profile names. For example, GUI screen 8000B is displaying two profiles with the name "Appendectomy." Under the first Appendectomy profile, the department "General Surgery" and the surgeon "Dr. Adams, Theresa" are listed. Under the second Appendectomy profile, the department "General Surgery" and the surgeon "Dr. Ko, Jeff" are listed. If more existing profiles are available than can fit in the profile window modal 8100 under the navigation bar 8110, then scrollbar 8120 can be used to scroll to the rest of the profile names.

In some aspects, a list of "favorites" profiles may be included below the navigation bar 8110 and above the ascending alphabetical list of profile names. Further, in some aspects, a favorite button 8122 (or a favorites checkbox, a favorites toggle switch, etc.) can be displayed along with each of the listed profile names. The favorite button 8122 can tapped by the user to toggle between a selected state and an unselected state. Placing one of the favorite buttons 8122 in the selected state will cause the profile name associated therewith to be displayed under the list of "favorites" profiles. Likewise, placing one of the favorite buttons 8211 in an unselected state will cause the profile name associated therewith to not be displayed under the list of "favorites" profiles. For example, GUI screen 8000B shows star-shaped favorites buttons 8122 in the selected state for three profile names (i.e., Appendectomy, Cholecystectomy, and General Surgery Default). These three profiles are listed under the favorites heading below the navigation bar 8110 as well as in the ascending alphabetical list of profile names (with the Cholecystectomy and General Surgery Default profiles viewable within the alphabetical list by using the scrollbar 8120). Thus, the "favorites" profiles can be easily accessed by users.

Sill referring to FIG. 14, tapping on or otherwise selecting one of the listed profile names can cause the modular energy system retrieve the profile and implement the operational settings associated with the selected profile. Further, tapping on or otherwise selecting one of the listed profile names can cause the GUI 8000 to display the settings associated with the selected profile. For example, selecting one of the profiles may cause GUI 8000 to display a screen similar to GUI scree 8000F, as discussed below in reference FIG. 18.

Figure 15:
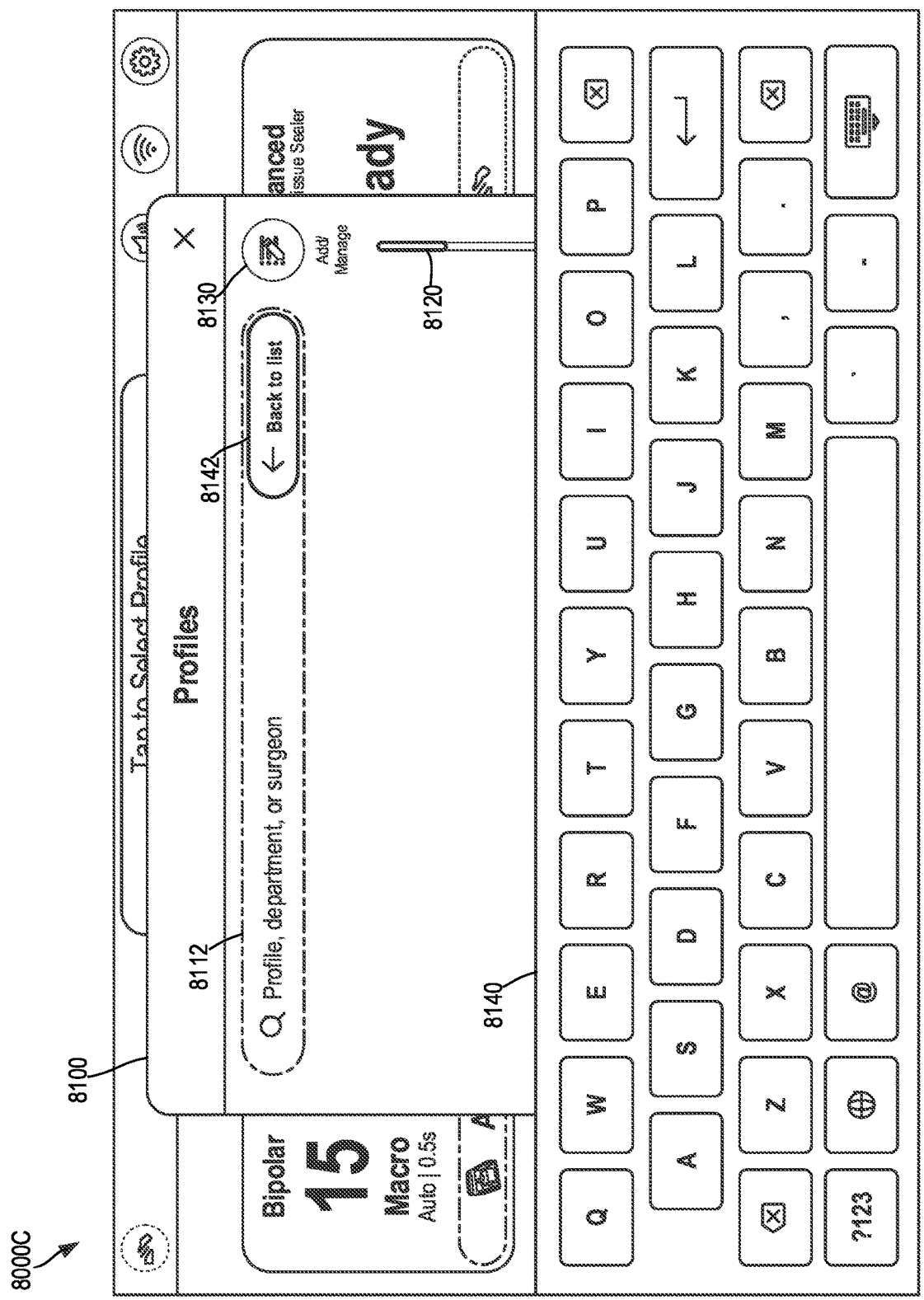

Returning to GUI screen 8000B and transitioning to GUI screen 8000C of FIG. 15, tapping or otherwise selecting the search bar 8112 can cause the search bar 8112 to expand. Tapping or otherwise selecting the search bar 8112 can also cause GUI 8000 to display a keyboard 8140. The keyboard 8140 can be configured to allow a user to type search terms related to an existing profile and/or profiles that the user wishes to locate. For example, typing part or all of a profile name, department name, and/or surgeon name using the keyboard 8140 will cause the typed text to appear in the search bar 8112 and can cause the GUI 8000 to display the names of any potential profiles matching the search term(s) below the search bar 8112. If more results matching the search term(s) are identified by the modular energy system than can fit within the profile modal window 8100, the scrollbar 8120 can be used to scroll through the profile results. Selecting one of the profile results can cause the modular energy system retrieve the profile and implement the operational settings associated with the selected profile. Further, selecting one of the listed profile names can cause the GUI 8000 to display the settings associated with the selected profile. The expanded search bar 8112 can also include a button 8142 that can be selected to cause the GUI to return to the navigation bar 8110, as shown in GUI screen 8000B of FIG. 14.

Returning to GUI screen 8000B and transitioning to GUI screen 8000D of FIG. 16, tapping or otherwise selecting the department tab 8116 can cause the names of the existing profiles to be sorted by department and arranged under the navigation bar 8110. A heading may be included for each department, wherein the profiles associated with that department are displayed thereunder. As used herein, "department" can refer to any grouping of procedure types and/or surgeons used to organize profiles. For example, as shown in the non-limiting aspect of FIG. 16, the profile names are sorted by department, wherein the departments include categories of procedures, such as Bariatric (e.g., including Gastric Bypass, Sleeve Gastrectomy), Colorectal, etc. In some aspects, by selecting the department tab 8116, the name of each surgeon that is associated with the profile(s) classified under a particular department may also be displayed under that department, wherein the corresponding profile names are displayed under each surgeon name. In other words, the profile names are sorted by department and then by surgeon. For example, in the non-limiting aspect of FIG. 16, the surgeon name "Dr. Smith, Julia" is listed under the department "Bariatric." Further, each of the names of the profiles associated with Dr. Julia Smith and classified in the Bariatric department are listed under "Dr. Smith Julia." In some aspects, the department name and/or the surgeon name headings can be expandable accordion elements 8150, 8152, 8154 (e.g., FIG. 16 shows elements 8150 and 8152 in an expanded state and element 8154 in a non-expanded state). Selecting one of the displayed profile names can cause the modular energy system retrieve the profile and implement the operational settings associated with the selected profile. Further, selecting one of the displayed profile names can cause the GUI 8000 to display the settings associated with the selected profile.

Figure 17:
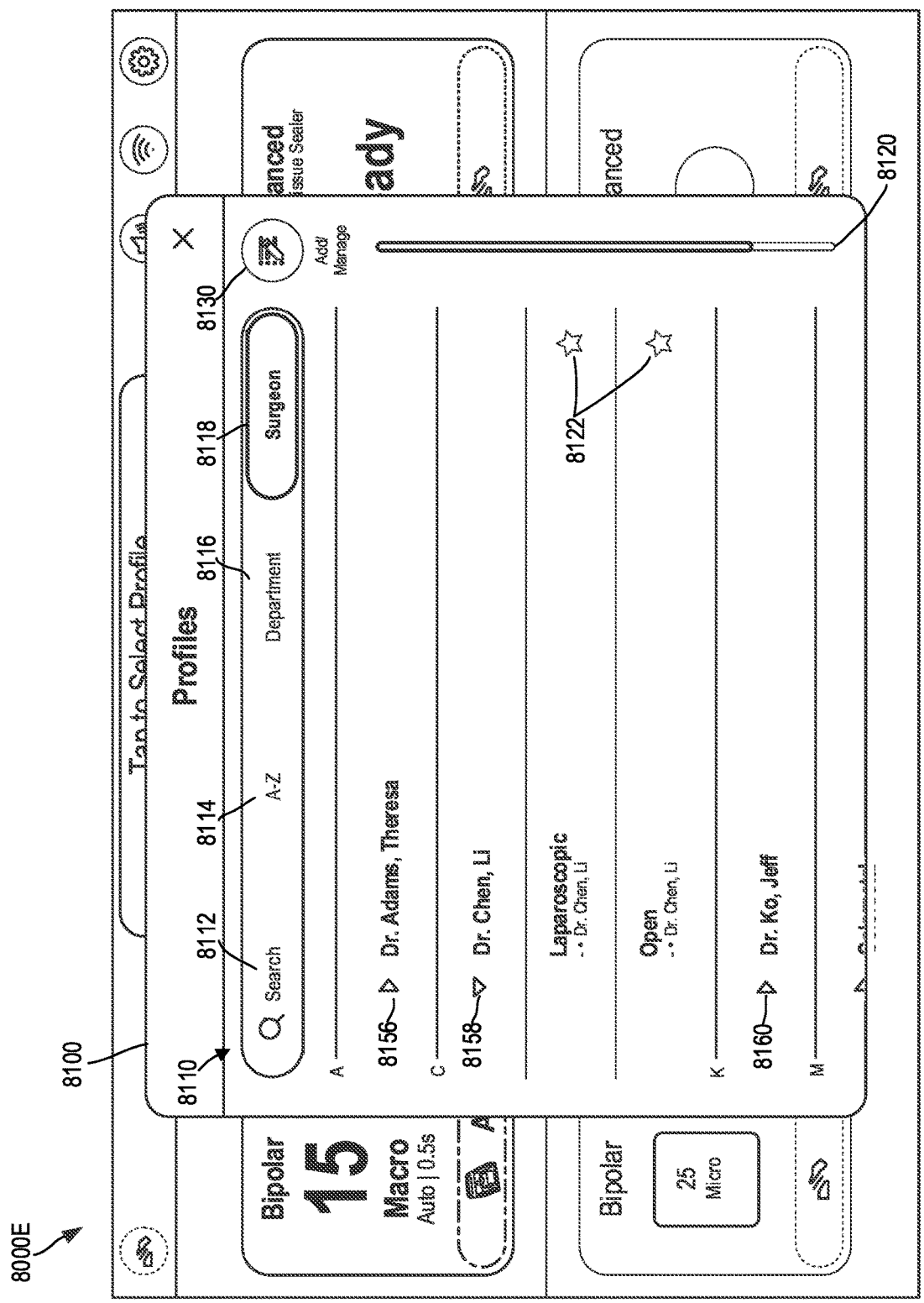

Transitioning from GUI screen 8000D to GUI screen 8000E of FIG. 17, tapping or otherwise selecting the surgeon tab 8116 can cause the names of the existing profiles to be sorted by surgeon name and arranged under the navigation bar 8110. A heading may be included for each surgeon name, wherein the existing profiles associated with that surgeon are displayed thereunder. In some aspects, the surgeon name headings can be expandable accordion elements 8156, 8158, 8160 (e.g., FIG. 17 shows element 8158 in an expanded state and elements 8156, 8160 in a non-expanded state). Selecting one of the displayed profile names can cause the modular energy system retrieve the profile and implement the operational settings associated with the selected profile. Further, selecting one of the displayed profile names can cause the GUI 8000 to display the settings associated with the selected profile.

In various aspects, the navigation bar 8110 can include additional and/or different tabs that can be selected to sort the profiles according to various categories. For example, profiles may be associated with and/or sorted according to groups of surgeons. These groups of surgeons can be a group practice that may be associated with a particular hospital, or a group practice that may be separate from a hospital. Accordingly, the navigation bar 8110 may include a "Group" tab that can be used to sort profiles according to these groups practices. Thus, a user interacting with GUI 8000 can sort and access profiles based on the procedures that a specific group of surgeons performs.

As explained above, selecting one of the profile names located using the navigation bar 8110 of the profile modal window 8100 can cause the modular energy system to retrieve and implement the settings associated with the profile and cause the GUI 8000 to display the settings associated with the profile. For example, referring again to GUI screen 8000E of FIG. 17, selecting the profile name "Laparoscopic" under the surgeon name heading "Dr. Chen, Li" can cause the settings associated with this profile to be implemented by the modular energy system. Further, GUI 8000 can populate and display the settings associated with this profile.

Figure 18:
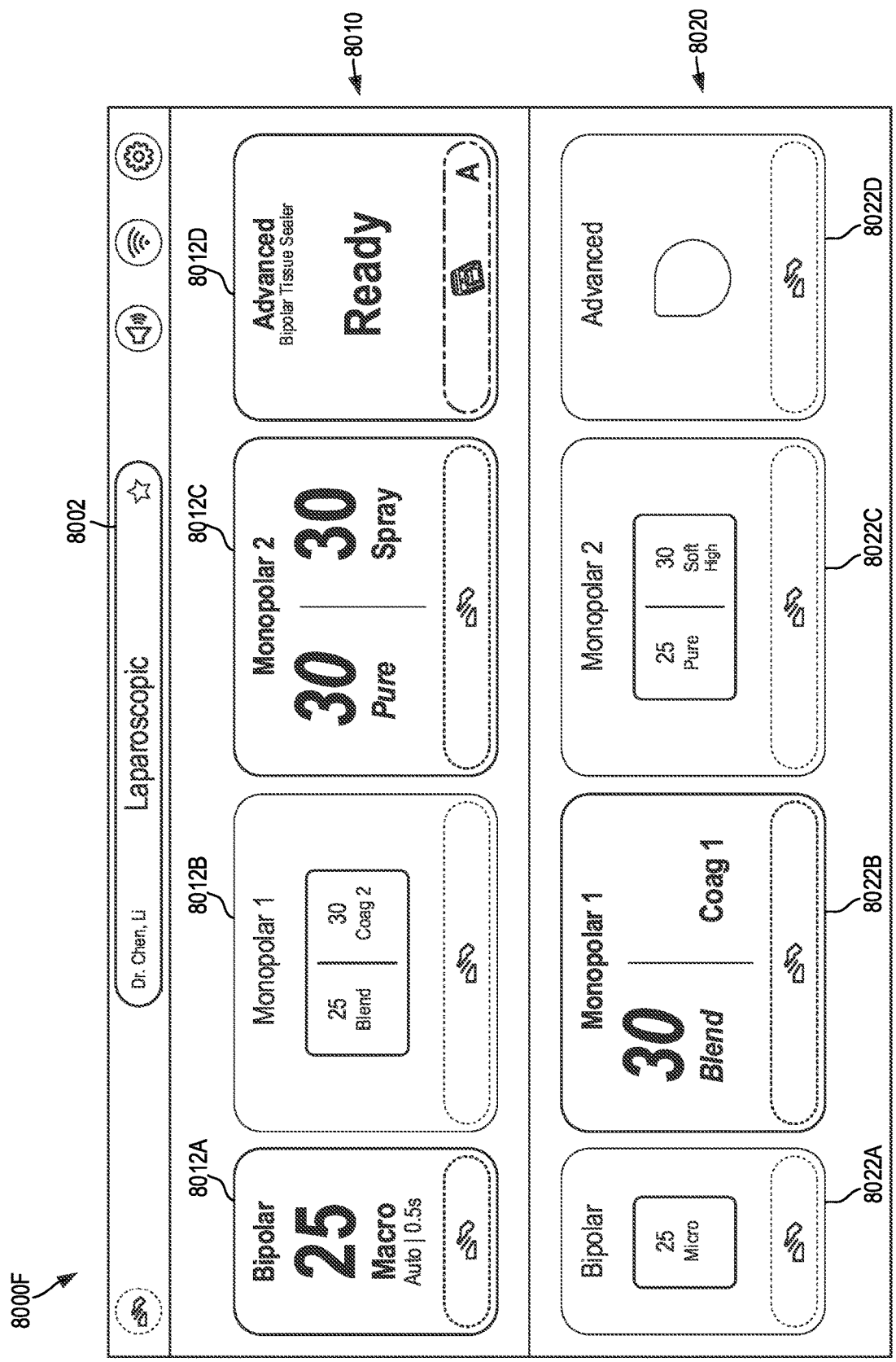

FIG. 18 illustrates an example GUI screen 8000F displaying settings associated with a selected profile (e.g. the "Laparoscopic" profile associated with Dr. Li Chen). In this example, the settings populated include the power level, modes, footswitch settings, and various other settings associated with the bipolar, monopolar 2, and combination ports of the first energy module and the monopolar 1 port of the second energy module, as shown in widgets 8012A, 8012C, 8012D, and 8022B, respectively. GUI screen 8000F is also displaying an updated profile bar 8002 that includes the name of the selected profile (e.g., "Laproscopic") and the name of the surgeon associated with the profile (e.g, "Dr. Chen, Li").

Figure 19:
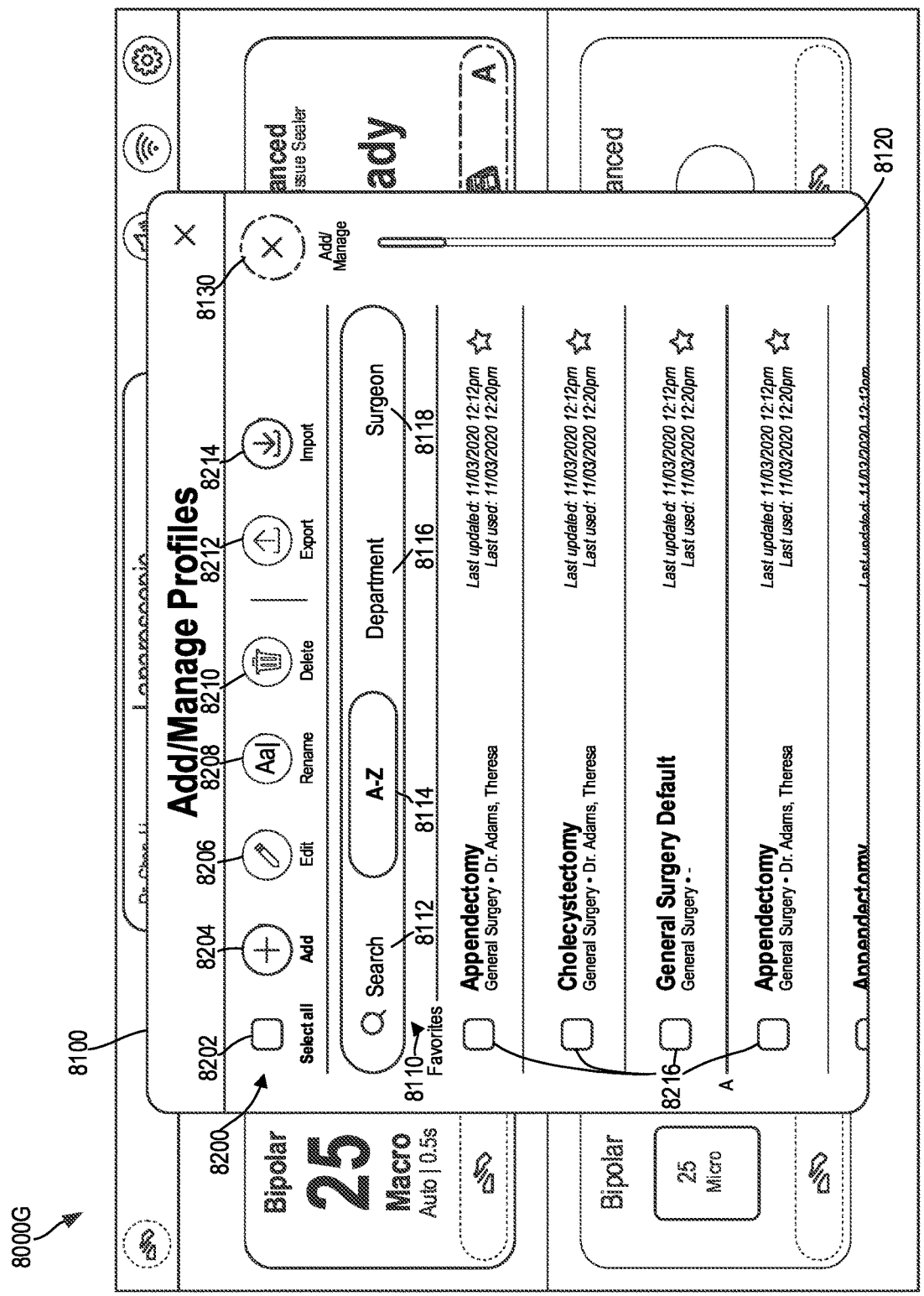
FIGS. 19-30 are illustrative graphical user interface screens for creating new profiles, in accordance with several aspects of the present disclosure.

FIGS. 19-30 are illustrative graphical user interface screens 8000G-T for creating new profiles, in accordance with several aspects of the present disclosure. Referring now to FIG. 19, GUI screen 8000G is shown displaying the profile modal window 8100 after a user has tapped on or otherwise selected the add/manage button 8130. Tapping on the add/mange button 8130 causes the profile modal window 8100 to display a profile management menu 8200 that can include buttons 8204, 8206, 8208, 8210, 8212, and 8214 that are used to implement actions related to creating and managing profiles. Any of the buttons 8204, 8206, 8208, 8210, 8212, and 8214 may be grayed out to indicate that the button is inactive. For example, the add button 8204 and the import button 8214 are active in GUI screen 8000G. Conversely, the edit button 8206, rename button 8208, delete button 8210, and export button 8212 are shown as grayed out and inactive in GUI screen 8000G. The profile management menu can also include a selection check box 8202.

Similar to the profile modal window 8100 displayed by GUI screens 8000B, 8000D, and 8000E described above, the profile modal window 8100 displayed by GUI screen 8000G includes a navigation bar 8110 that can be used to locate existing profiles that are displayed therebelow. Further, based on selecting the add/manage button 8130, selection check boxes 8216 are displayed along with each of the displayed profile names. Selecting the check box 8202 can cause all of the selection boxes 8216 associated with the profiles to become selected. Further, selecting one or more of the selection check boxes 8216 can cause the inactive edit button 8206, rename button 8208, delete button 8210, and/or export button 8212 to become active. As discussed below, selecting selection check box(es) 8216 associated with existing profile(s) (i.e., selecting existing profile(s)) and tapping one of the edit button 8206, rename button 8208, delete button 8210, and/or export button 8212 can cause the modular energy system to perform a profile management action related to the selected profile(s)).

Figure 20:
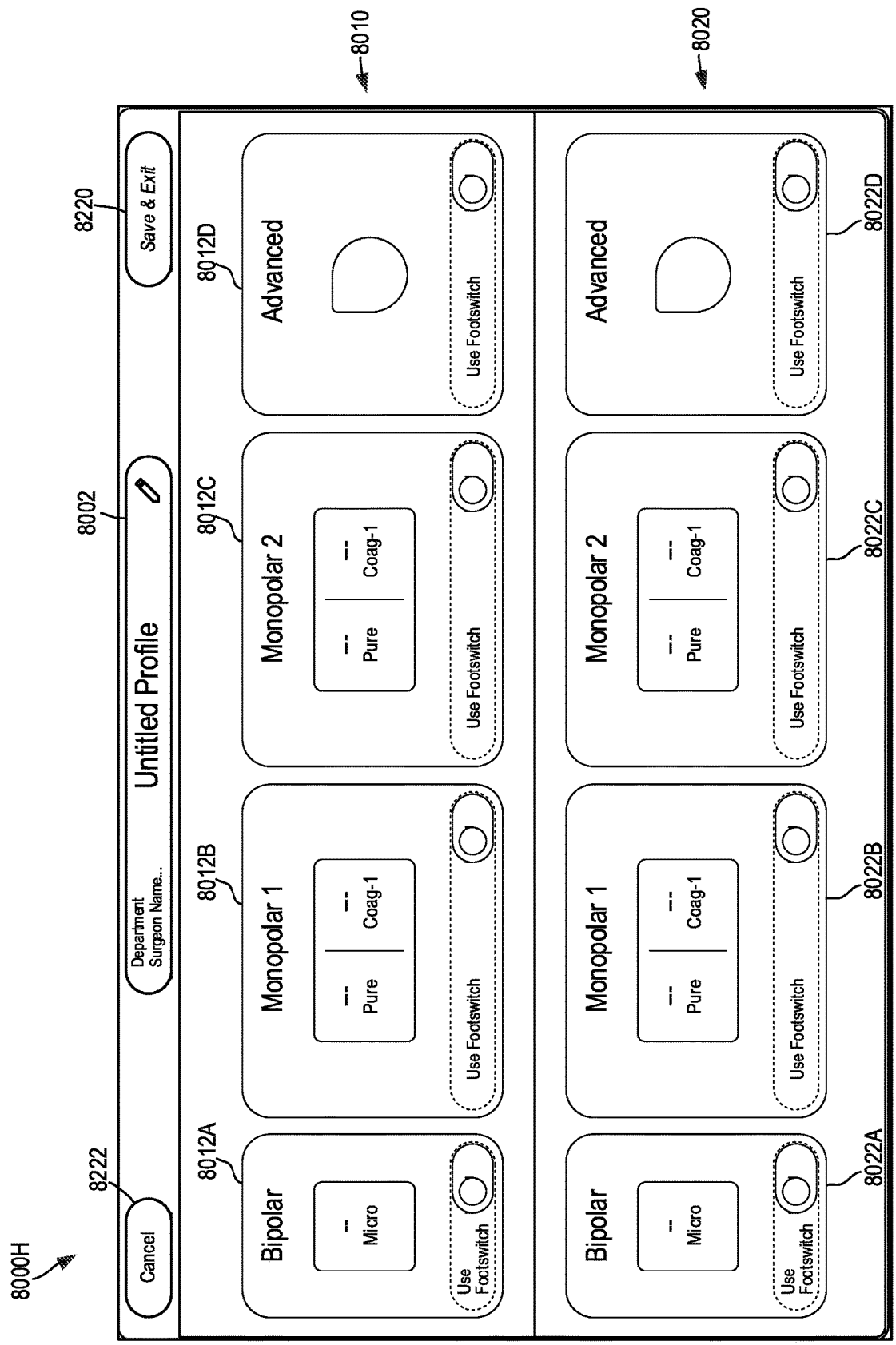

Transitioning from GUI screen 8000G to GUI screen 8000H of FIG. 20, tapping or otherwise selecting the add button 8204 can cause GUI screen 8000H to be displayed. In some aspects, GUI screen 8000H represents a profile creation and editing mode of GUI 8000. Similar to GUI screen 8000A of FIG. 13, GUI screen 8000G includes a first portion 8010 with widgets 8012A-D corresponding to ports of the first energy module of the modular energy system and a second portion 8020 with widgets 8022A-D corresponding to ports of the second energy module of a modular energy system. However, the settings related to widgets 8012A-D, 8022A-D of GUI screen 8000H have not yet been selected. Thus, in this profile creation and editing mode of GUI 8000, a user can interact with any of the widgets 8012A-D, 8022A-D to input desired settings for creating a new profile. In some aspects, tapping on one of the widgets 8012A-D, 8022A-D will cause an energy modality editing modal window to be displayed that the user can interact with to adjust and/or input various settings specific to the selected energy modality.

Figure 21:
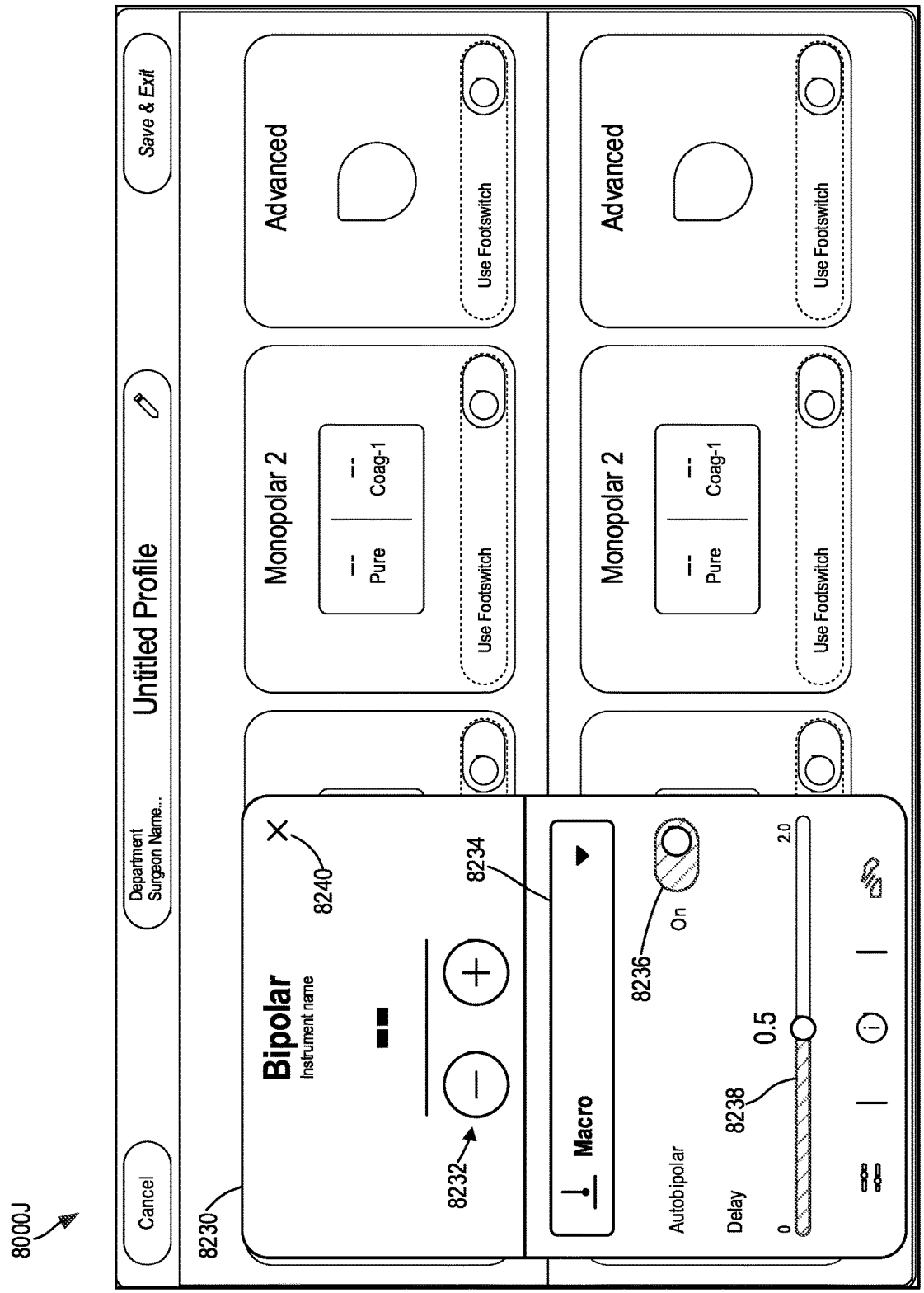

For example, transitioning from GUI screen 8000H to GUI screen 8000J of FIG. 21, tapping or otherwise selecting widget 8012A can cause an energy modality editing modal window 8230 to be displayed. The energy modality editing modal window 8230 can include a spinner element 8232 that can be used to input/adjust the energy level, a drop down menu 8234 that can be used to select an energy mode, a toggle switch 8236 to toggle between auto mode (e.g., autobipolar) on and off, a slider 3238 to adjust a delay setting, and/or other GUI elements used to control various other setting related to the energy modality.

Figure 22:
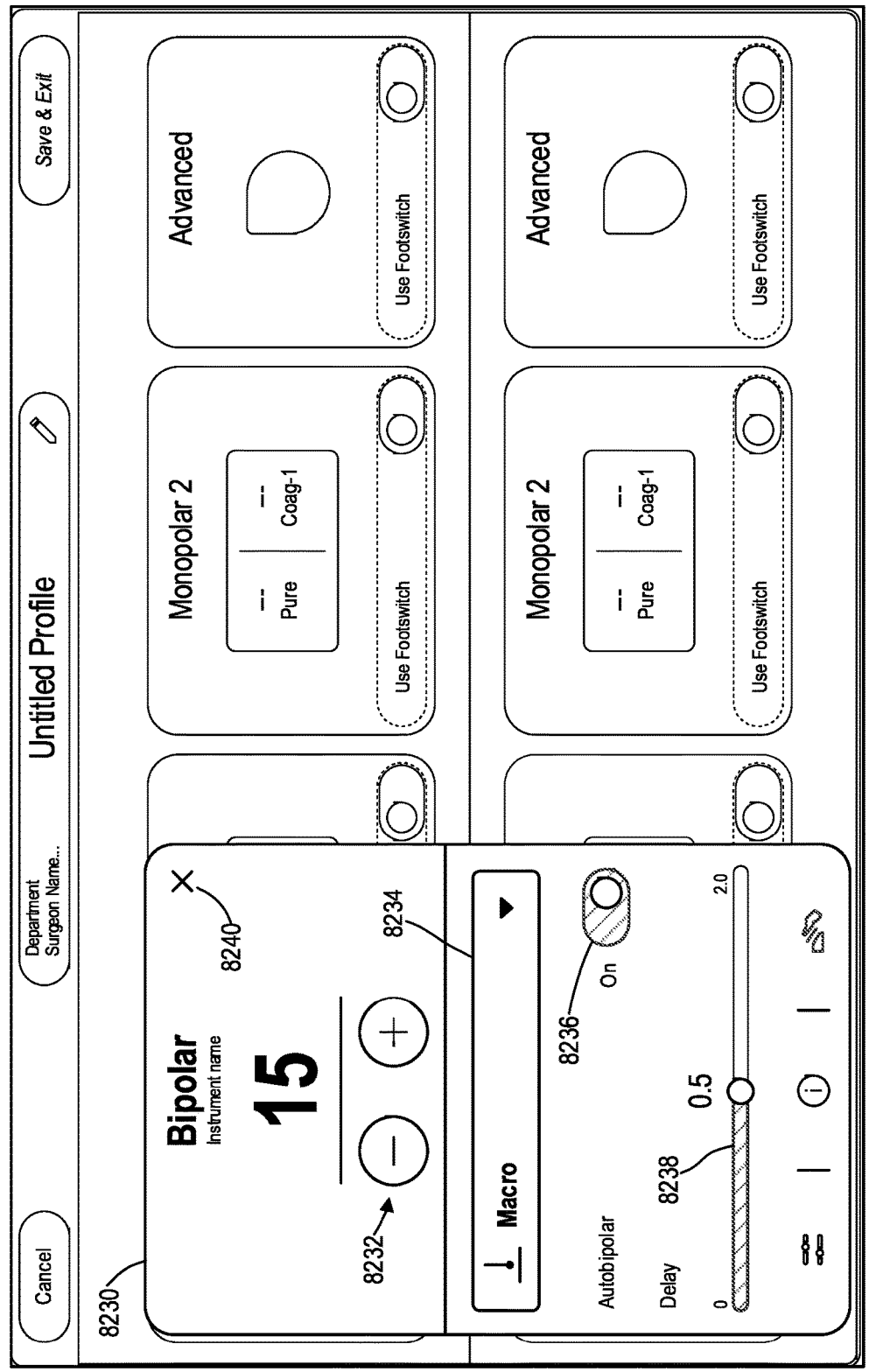

Transitioning from GUI screen 8000J to GUI screen 8000K of FIG. 22, the energy modality editing modal window 8230 is shown after a user has adjusted and/or input the desired settings for the energy modality. Transitioning from GUI screen 8000K to GUI screen 8000L of FIG. 23, after the desired settings have been achieved, close button 8240 of the energy modality editing modal window 8230 can be selected. This causes GUI screen 8000L to be displayed, which is similar to GUI screen 8000J except the newly selected settings have been populated into widget 8012A.

Figure 23:
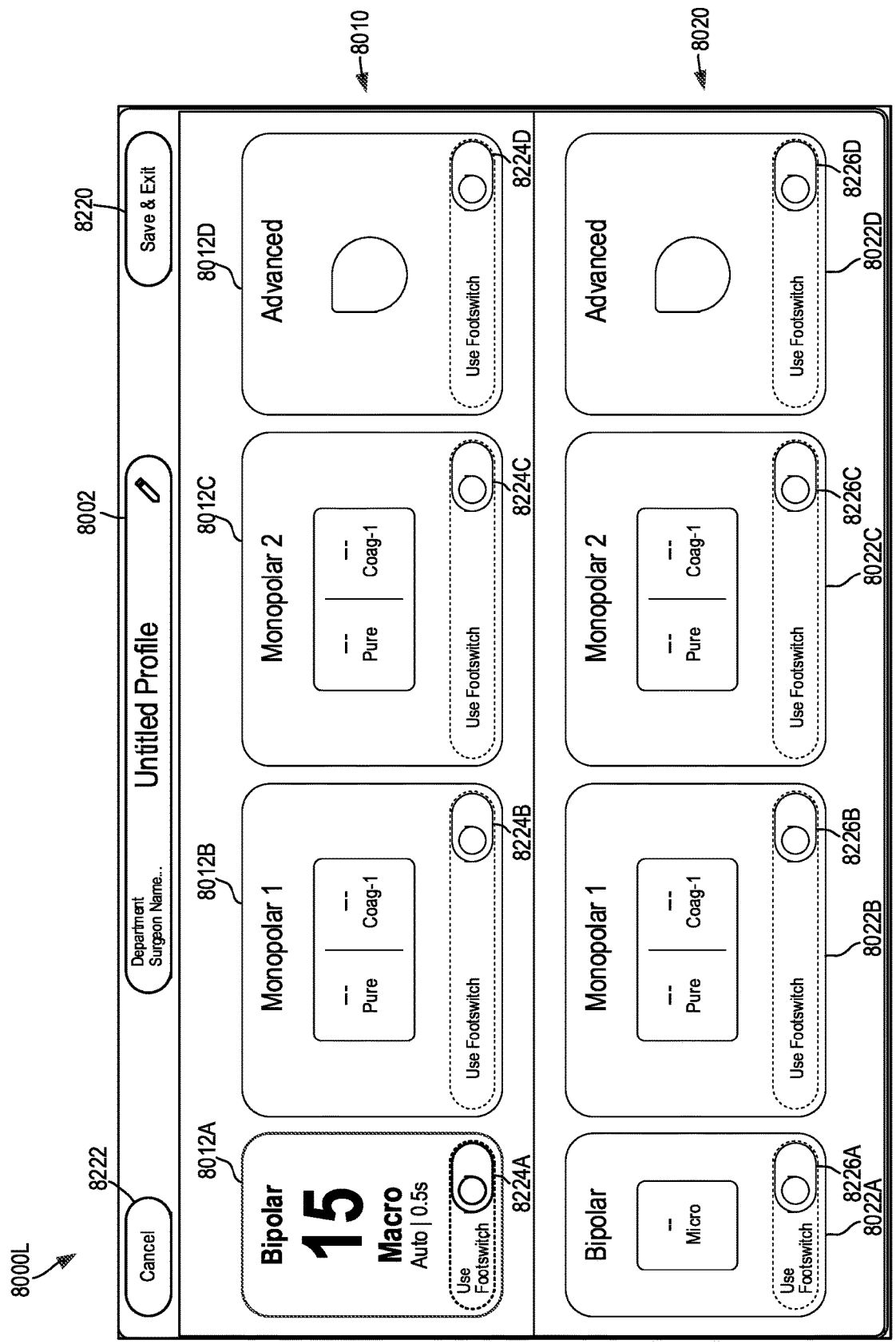
Figure 24:
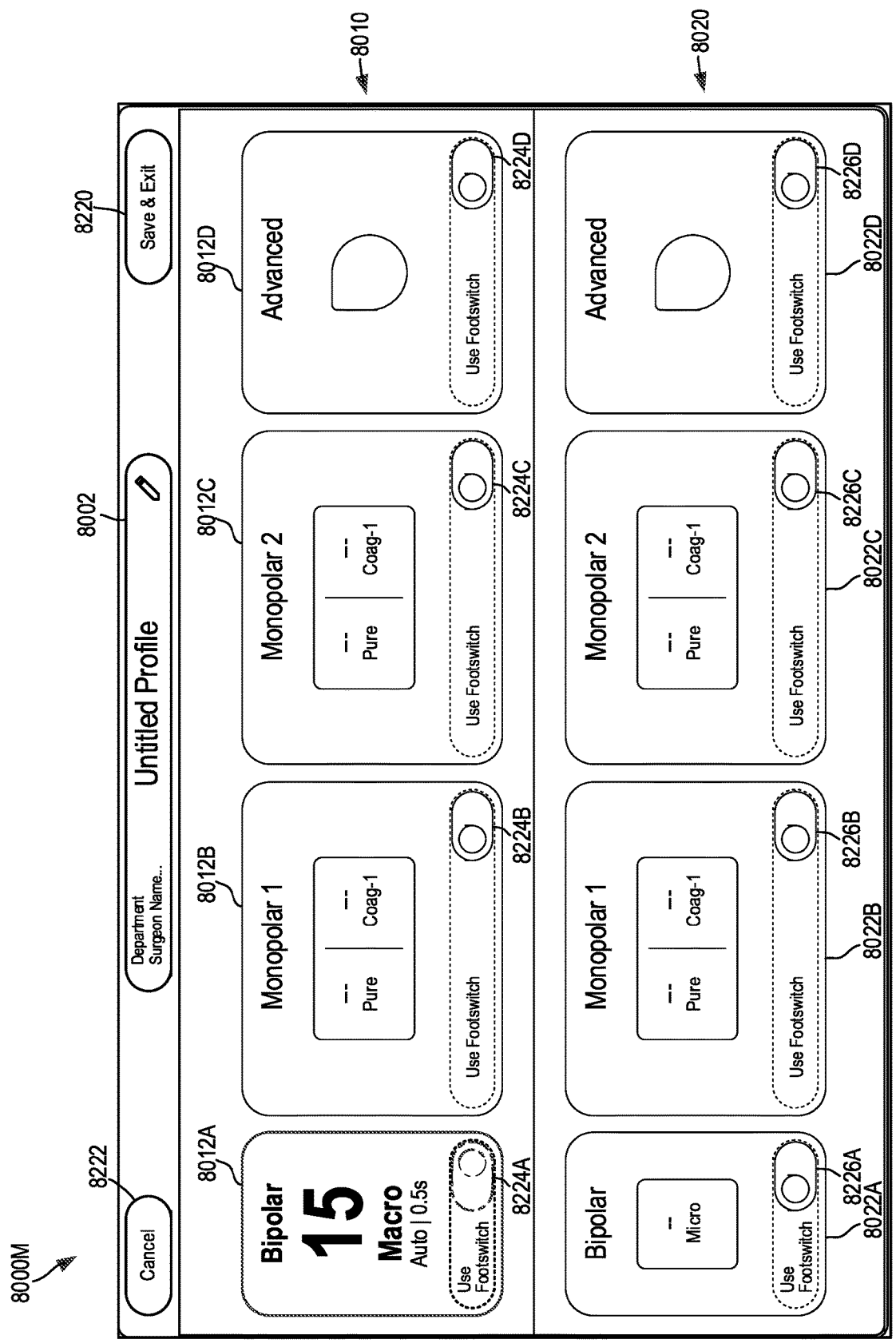

Still referring to GUI screen 8000L of FIG. 23, each of the widgets 8012A-D, 8022A-D can include a footswitch toggle 8224A-D, 8226A-D, respectively. The footswitch toggles 8224A-D, 8226A-D can be adjust by the user to indicate whether the port corresponding to each of the widgets 8012A-D, 8022A-D can be controlled by a footswitch. For example, transitioning from GUI screen 8000L to GUI screen 8000M of FIG. 24, the footswitch toggle 8224A for widget 8012A has been adjusted indicating that the bipolar port associated with widget 8012A is set to be controlled by a footswitch. The user can continue to interact with the profile creation and editing mode of GUI 8000 by selecting widgets 8012A-D, 8022A-D, adjusting energy modality settings of the widgets using the editing modal windows that appear upon selecting the widgets 8012A-D, 8022A-D, and adjusting footswitch toggles 8224A-D, 8226A-D until the desired operational settings for the profile are achieved. For example, FIG. 25 illustrates a GUI screen 8000N after a user has input and/or adjusted widgets 8012A, 8012B, 8012D, 8022A, and 8022C to achieve the user's desired operational settings for the new profile.

Figure 25:
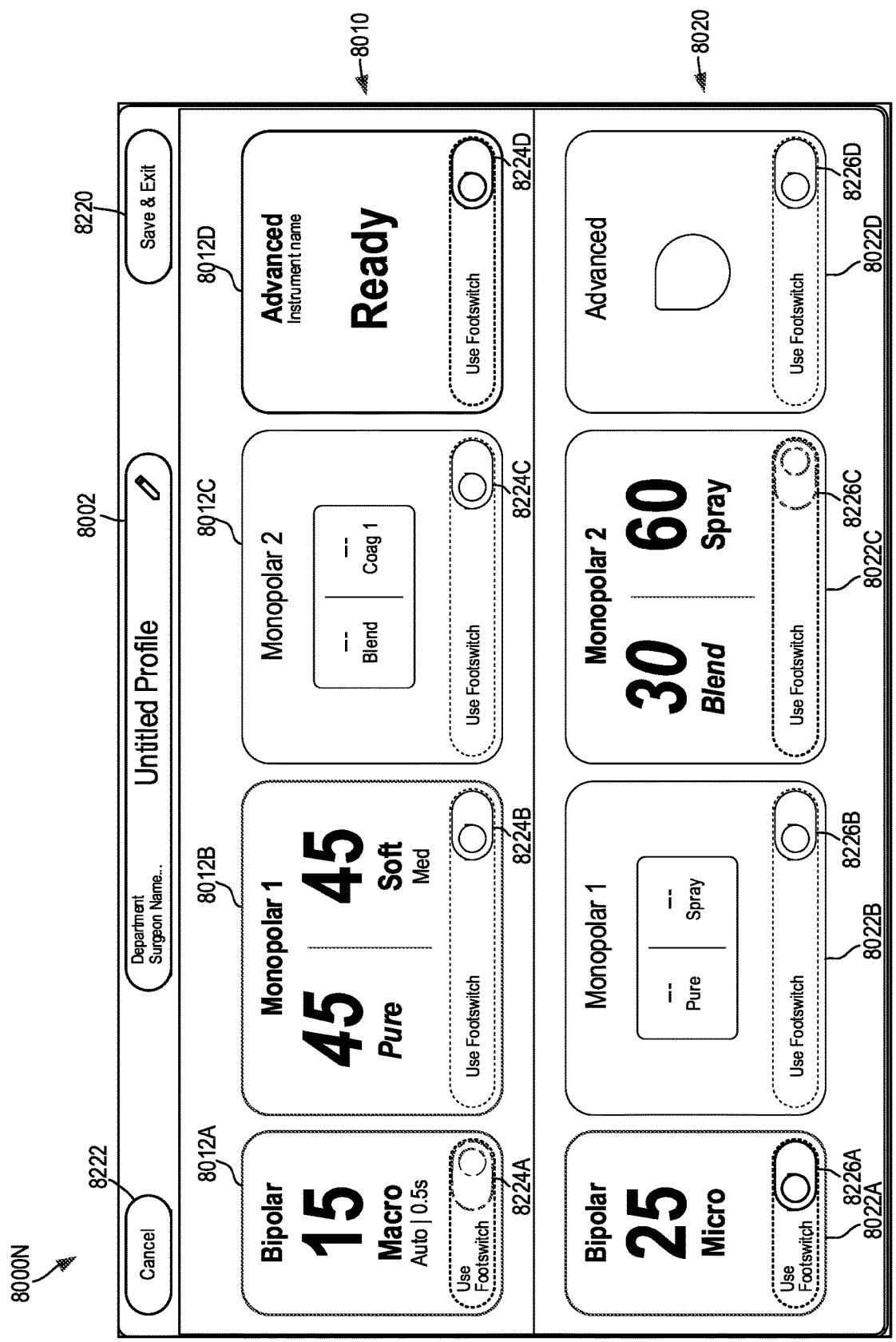

Still referring to GUI screen 8000N of FIG. 25, the profile bar 8002 at the top of the GUI 8000 can be selected to input and/or edit the name of the profile that is being created and/or edited. Transitioning from GUI screen 8000N to GUI screen 8000P of FIG. 26, tapping or otherwise selecting the profile bar 8002 when GUI 8000 is in profile creation and editing mode causes profile naming modal window 8240 to be displayed. The profile naming modal window 8240 includes a profile name bar 8242, a department drop down menu 8244, a surgeon drop down menu 8246, and a close button 8248.

Figure 27:
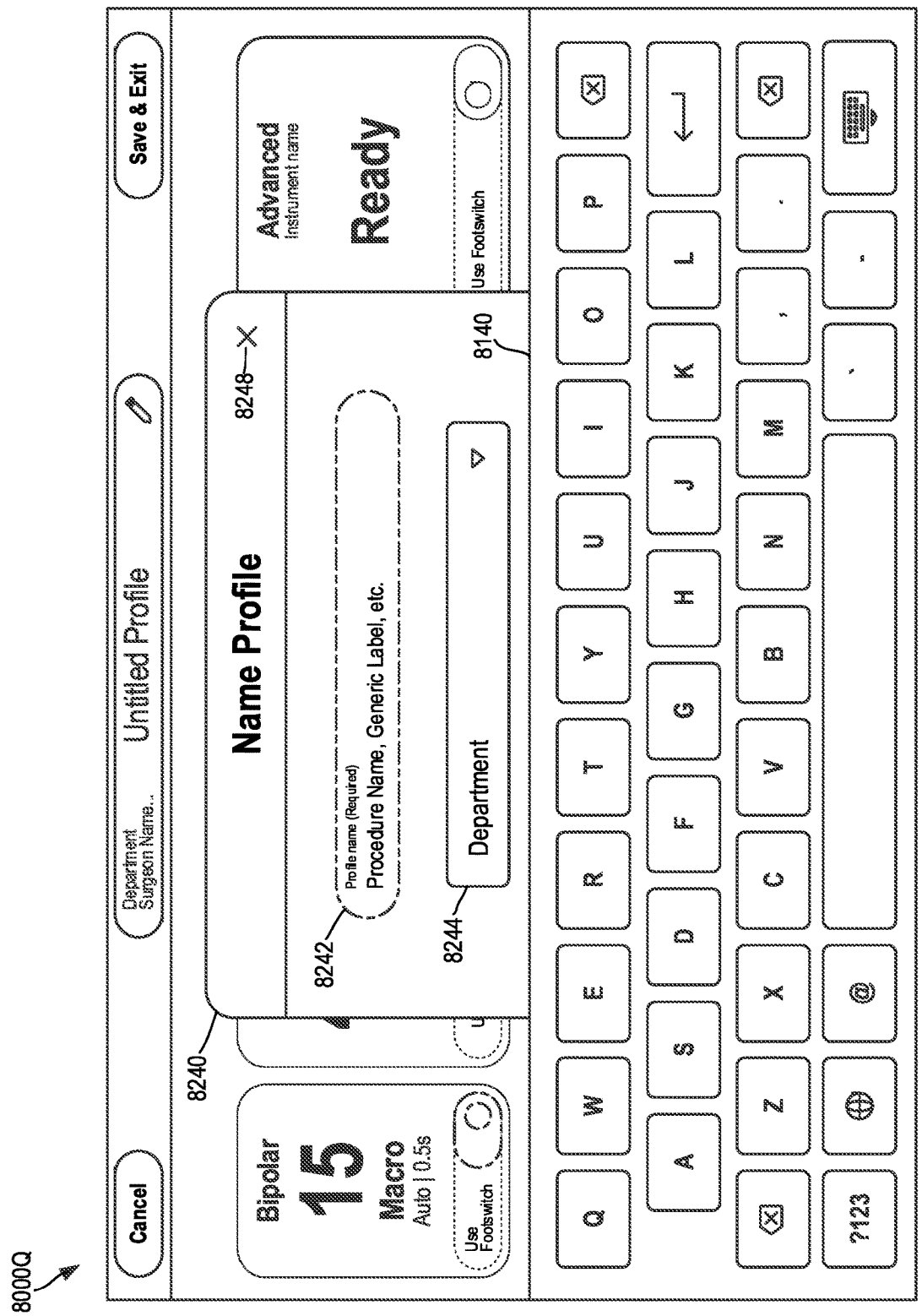

Transitioning from GUI screen 8000P to GUI screen 8000Q of FIG. 27, tapping or otherwise selecting the profile naming bar 8242 causes keyboard 8140 to be displayed. A user can use the keyboard 8140 to type the name that he or she wishes to assign to the profile being created and/or edited. For example, transitioning to GUI screen 8000R of FIG. 28, the name "General Lap" has been typed into the profile naming bar 8242.

Figure 26:
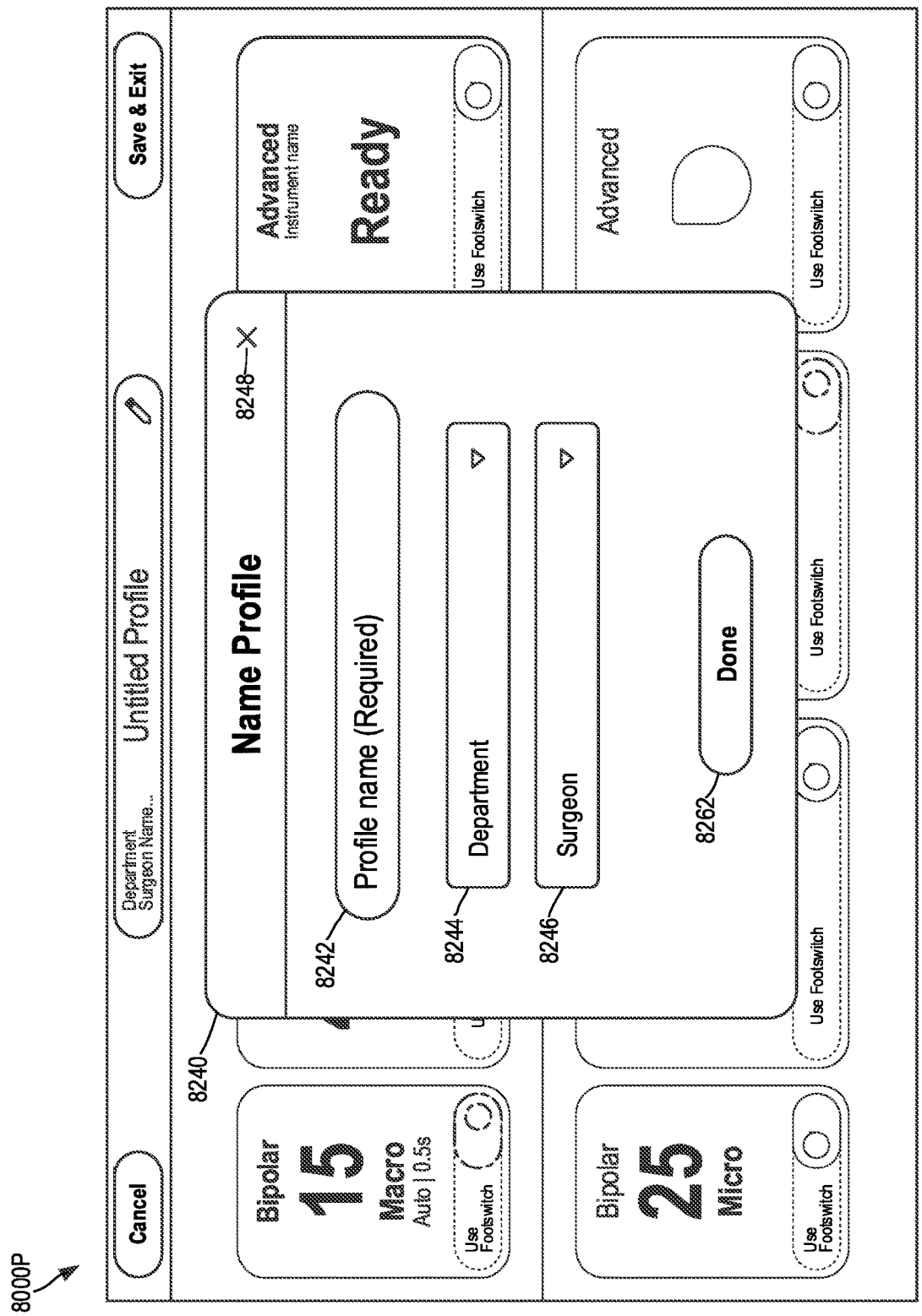

Referring again to GUI 8000P of FIG. 26, selecting the department drop down menu 8244 will cause the GUI 8000 to display a list of the departments associated with the existing profiles. A user can select one of these existing departments to assign it to the profile being created and/or edited. Similarly, selecting the surgeon drop down menu 8246 will cause the GUI 8000 to display a list of the surgeons associated with the existing profiles. A user can select one of these existing surgeons to assign it to the profile being created and/or edited. However, a user may wish to assign a new department and/or a new surgeon to the profile. Thus, the department drop down menu 8244 and/or the surgeon drop down menu 8246 can include an GUI element allowing the user to create a new department and/or surgeon name.

Figure 28:
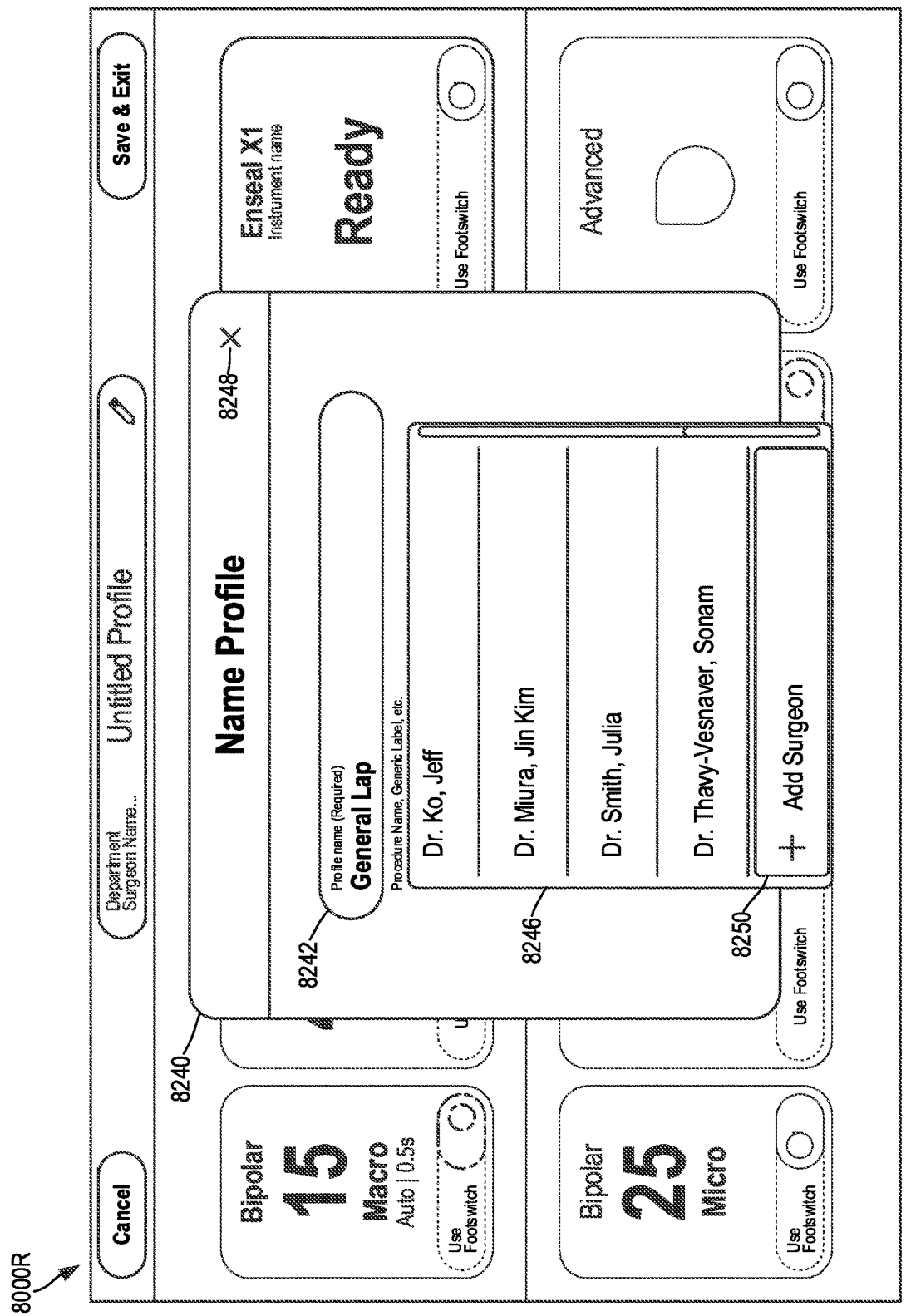
Figure 29:
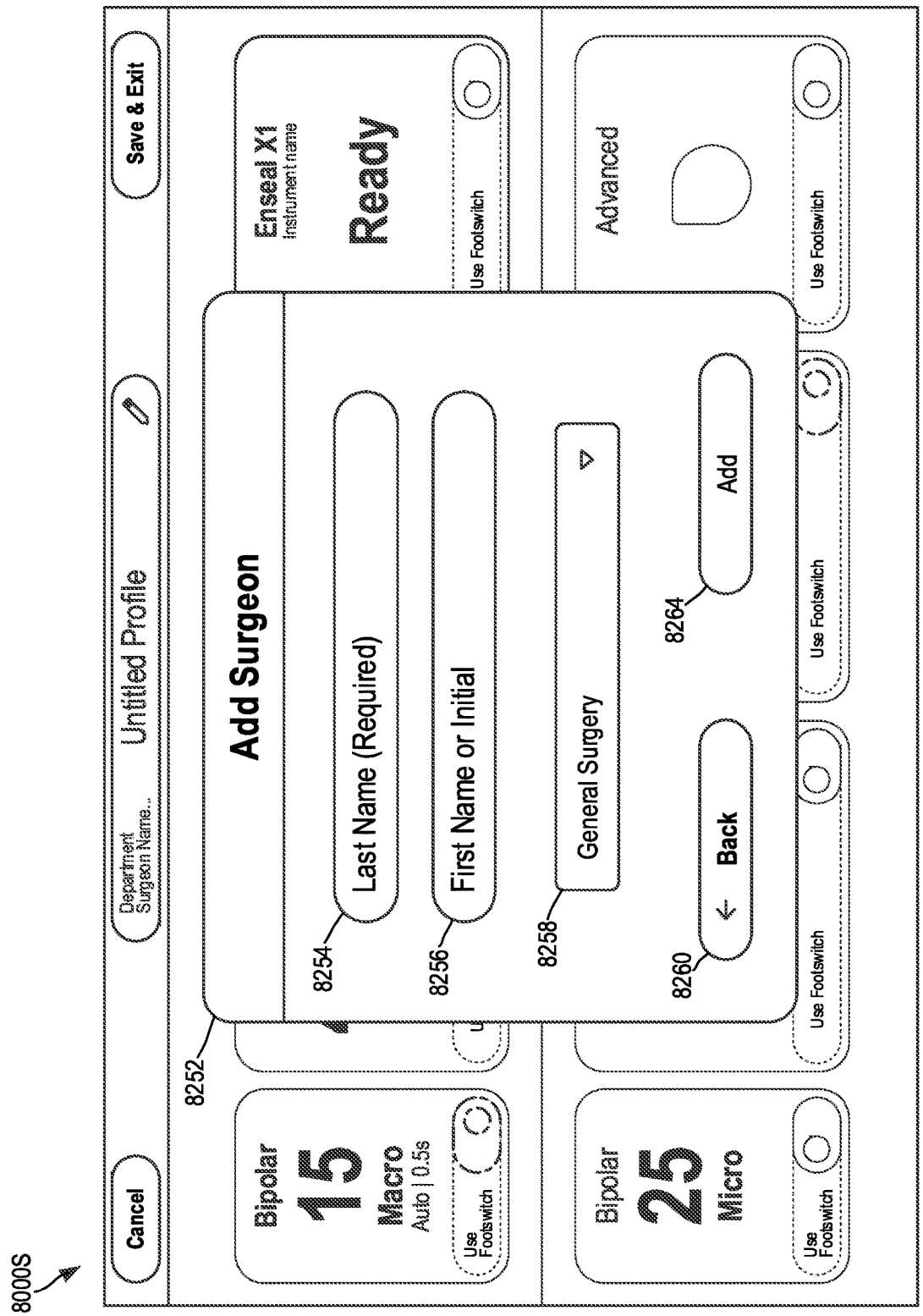

For example, referring now to GUI 8000R of FIG. 28, the surgeon drop down menu 8246 is expanded. At the bottom of the list of existing surgeons, a button 8250 is included that can be selected to add a new surgeon name. Transitioning to GUI 8000S of FIG. 29, tapping on the button 8250 will cause a new surgeon modal window 8252 to be displayed. The new surgeon modal window 8252 can include boxes 8254 and 8256 that can be selected to add the last and first name of the surgeon using keyboard 8140 (not shown in FIG. 28). In some aspects, the new surgeon modal window 8252 can include a department drop down menu 8258 allowing the user to associate the surgeon with an existing department and/or a new department. The back button 8260 can be used to return to the profile naming modal window 8240.

Figure 30:
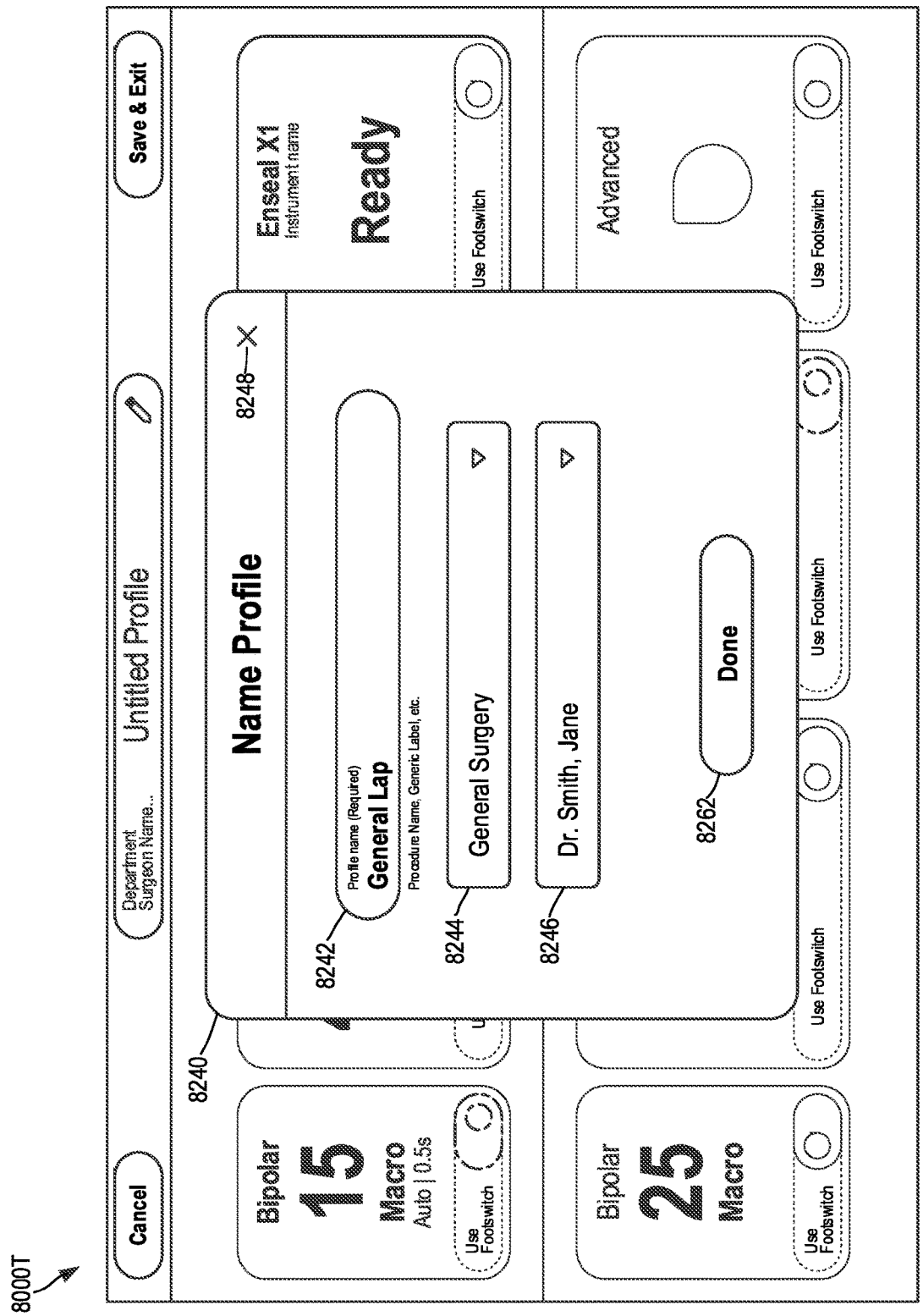

Transitioning to GUI screen 8000T of FIG. 30, upon entering and/or selecting the desired profile name, department, and surgeon, a done button 8262 can become active in the new profile naming modal window 8240. Tapping or otherwise selecting the done button 8262 causes the profile name, surgeon, and/or department information to be populated into the profile bar 8002. Referring again to GUI screen 8000N of FIG. 25, upon entering the desired operational setting information and/or profile name information, the save and exit button 8220 can be tapped or otherwise selected to save the newly created/edited profile and exit the profile creation and editing mode of GUI 8000. The profile creation and editing mode of GUI 8000 also includes a cancel button 8222. Tapping or otherwise selecting the cancel button 8222 can cause the GUI 8000 to exit the profile creation and editing mode. Tapping on cancel button 8222 may also discard any unsaved settings and/or names that may have been entered.

Figure 31:
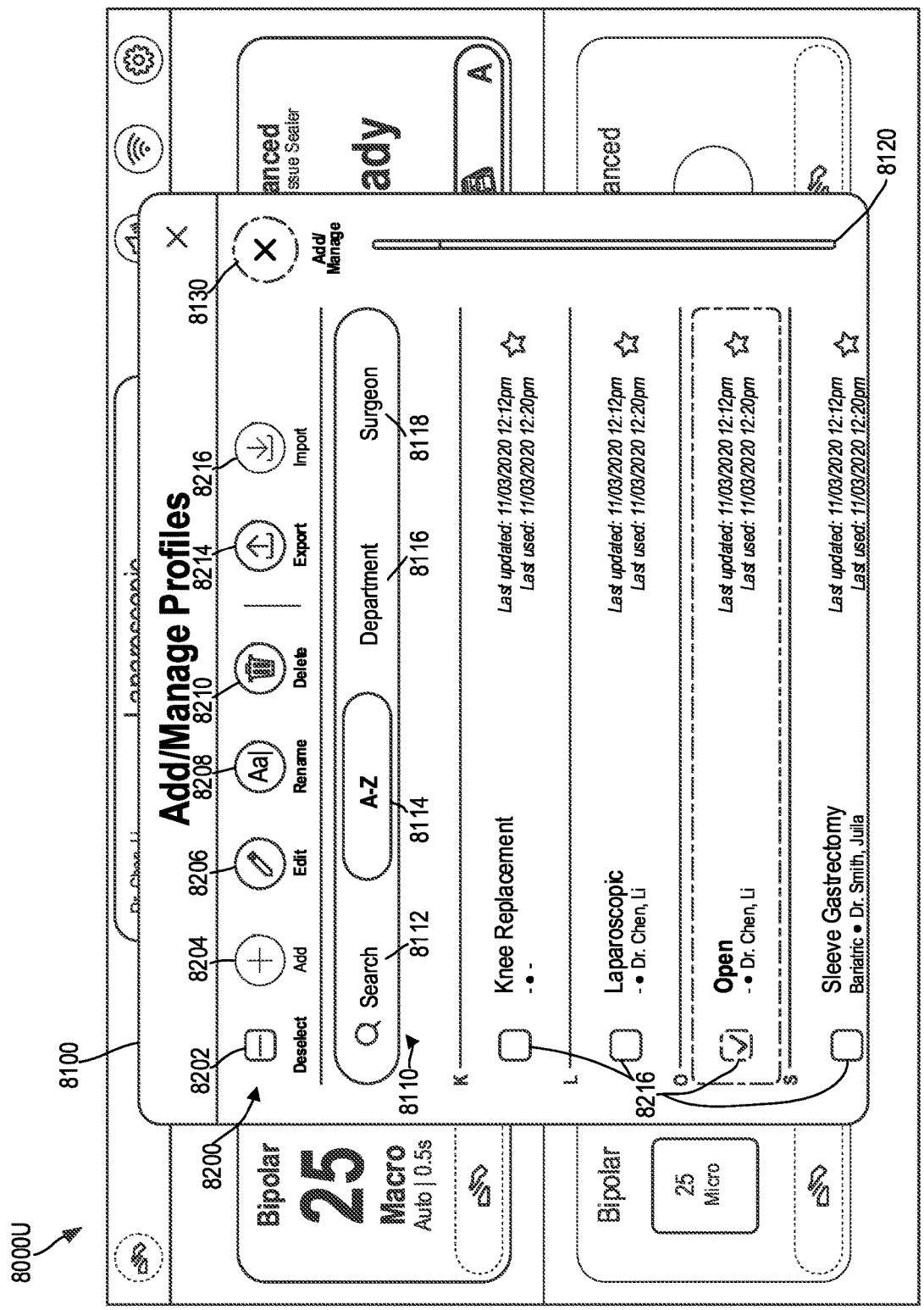
FIGS. 31-39 are illustrative graphical user interface screens for managing existing profiles, in accordance with several aspects of the present disclosure.
Figure 32:
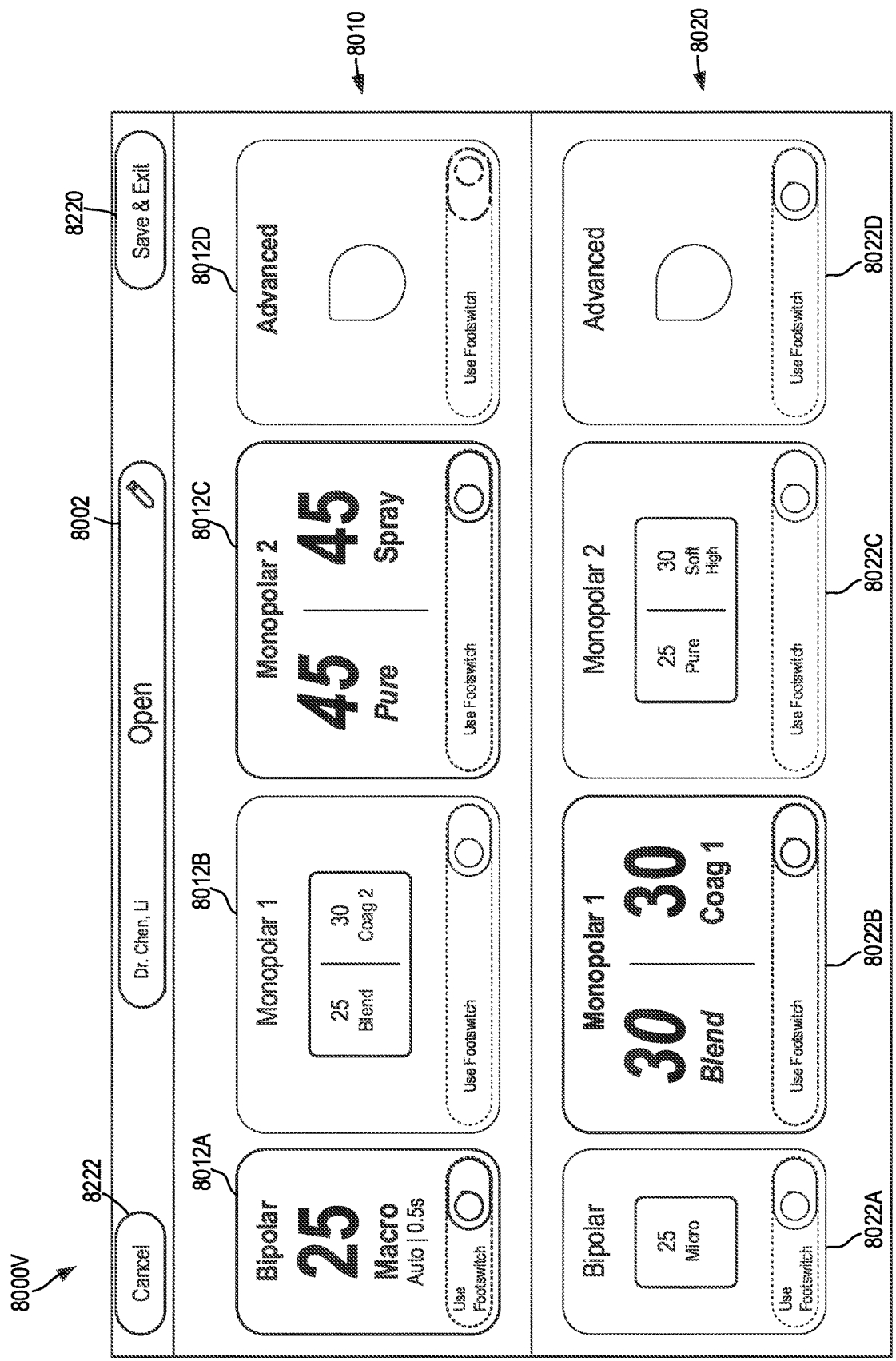

FIGS. 31-39 are illustrative graphical user interface screens 8000U-CC for managing existing profiles, in accordance with several aspects of the present disclosure. Referring now to FIG. 31, GUI screen 8000U is shown displaying the profile modal window 8100 after a user has selected the one of the selection check boxes 8216 associated with one of the displayed profiles (i.e., the "Open" profile associated with "Dr. Chen, Li"). Selecting one of the selection check boxes 8216 can cause the edit button 8206, rename button 8208, delete button 8210, and export button 8212 to become active. Further, the selection check box 8202 (e.g., a tri-state check box) in the profile management menu 8200 is now shown in an intermediate state indicating that some but not all of the existing profiles are selected.

Still referring to GUI 8000U of FIG. 31, in one aspect, tapping otherwise selecting the rename button 8208 while one of the selection check boxes 8216 is selected can cause the GUI 8000 to display the profile naming modal window 8240 (e.g., shown in FIG. 26). A user can then interact with the profile naming modal window 8240 to edit the name of the existing profile.

Still referring to GUI 8000U of FIG. 31, in one aspect, tapping or otherwise selecting the edit button 8206 while one of the selection check boxes 8216 is selected can cause GUI 8000 to display the selected profile in profile creation and editing mode. For example, transitioning from GUI screen 8000U to GUI screen 8000V FIG. 32, as a result of tapping the edit button 8206, the "Open" profile associated with "Dr. Chen, Li" is being displayed. Specifically, GUI screen 8000V is showing the widgets 8012A-D, 8022A-D populated with the settings of the "Open" profile. Further, the profile bar 8002 is displaying the name of the profile and the name of the surgeon associated with the profile. Similar to the aspects discussed above with respect to GUI screens 8000H-T of FIGS. 20-30, a user can interact with GUI screen 8000V to adjust the various settings of the profile.

Figure 33:
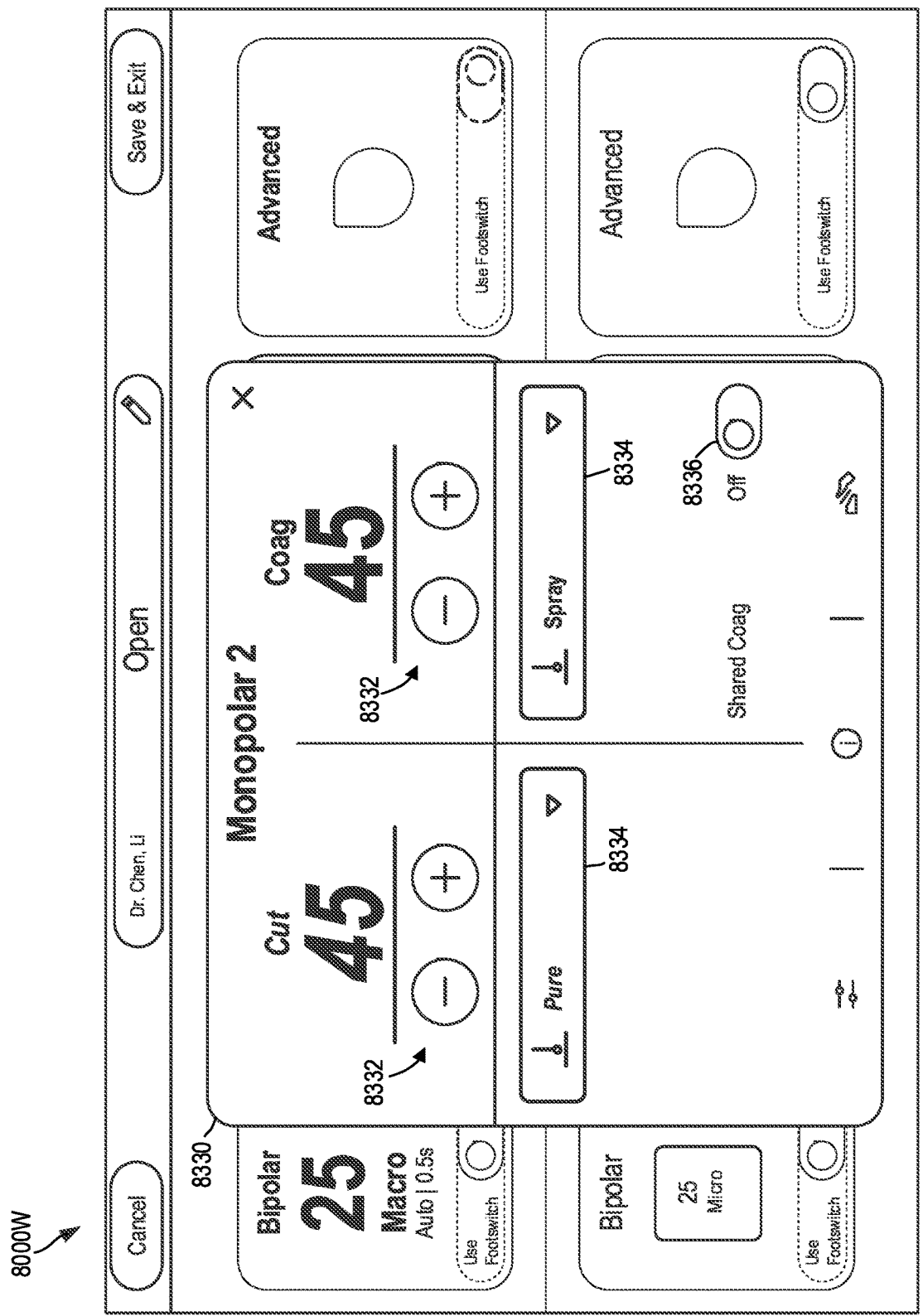
Figure 34:
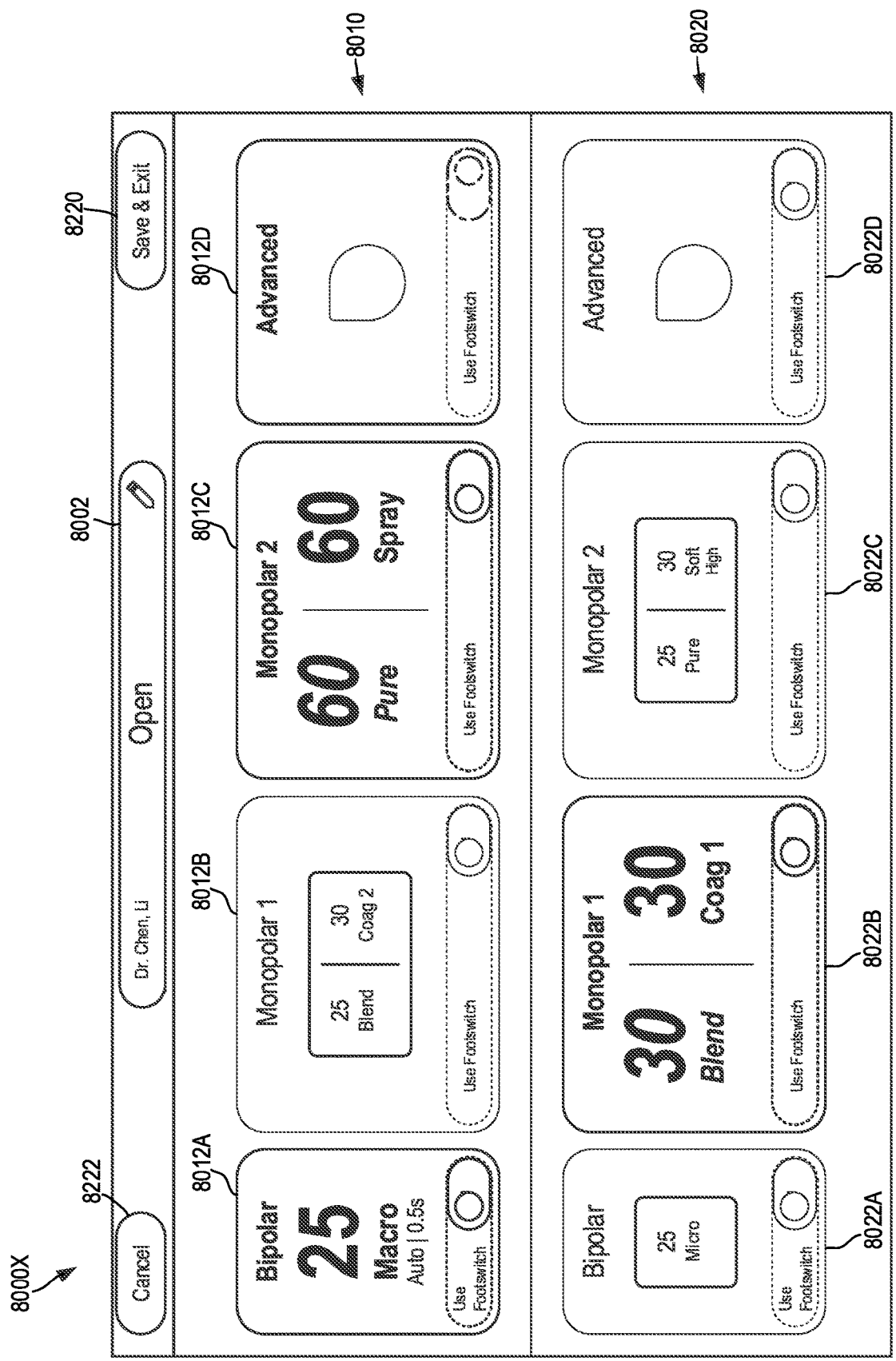

For example, transitioning from GUI screen 8000V to GUI screen 8000W of FIG. 33, tapping on or otherwise selecting widget 8012C can cause GUI 8000 to display an energy modality editing modal window 8330. The energy modality editing modal window 8330 is similar to the energy modality editing window 8230 of FIG. 22 in many respects, except that energy modality editing modal window 8330 is displaying adjustable settings related to a monopolar energy modality/port. Thus, in various aspects, energy modality editing modal window 8330 can include a spinner elements 8332 that can be used to adjust the energy levels, drop down menus 8334 that can be used to select the energy modes, and a toggle switch 8336 to toggle between shared coag mode on and off, and/or other GUI elements used to control various other settings related to the energy modality. For example, a user may wish to update both the cut and coag energy levels from 45 to 60 for this energy modality. The user can tap the plus button of spinner elements 8332 until the desired energy level is achieved. Upon achieving the desired settings, the user can tap the close button 8340. Transitioning from GUI screen 8000W to GUI screen 8000X of FIG. 34, tapping the close button 8340 will close the energy modality editing modal window 8330 and populate the updated setting in widget 8012C.

In various aspects, existing profiles can be edited using GUI 8000 without entering the profile creation and editing mode. For example, GUI 8000 can be configured to allow users to open a profile as if a procedure was being performed, update various settings of the profile, and save the profile to include the updated settings. Thus, GUI 8000 can be configured to allow a surgeon to adjust settings of the profile while performing a procedure and, if desired, allow the surgeon to save the adjusted settings so that those adjusted settings can be easily implemented the next time the profile is opened.

Figure 35:
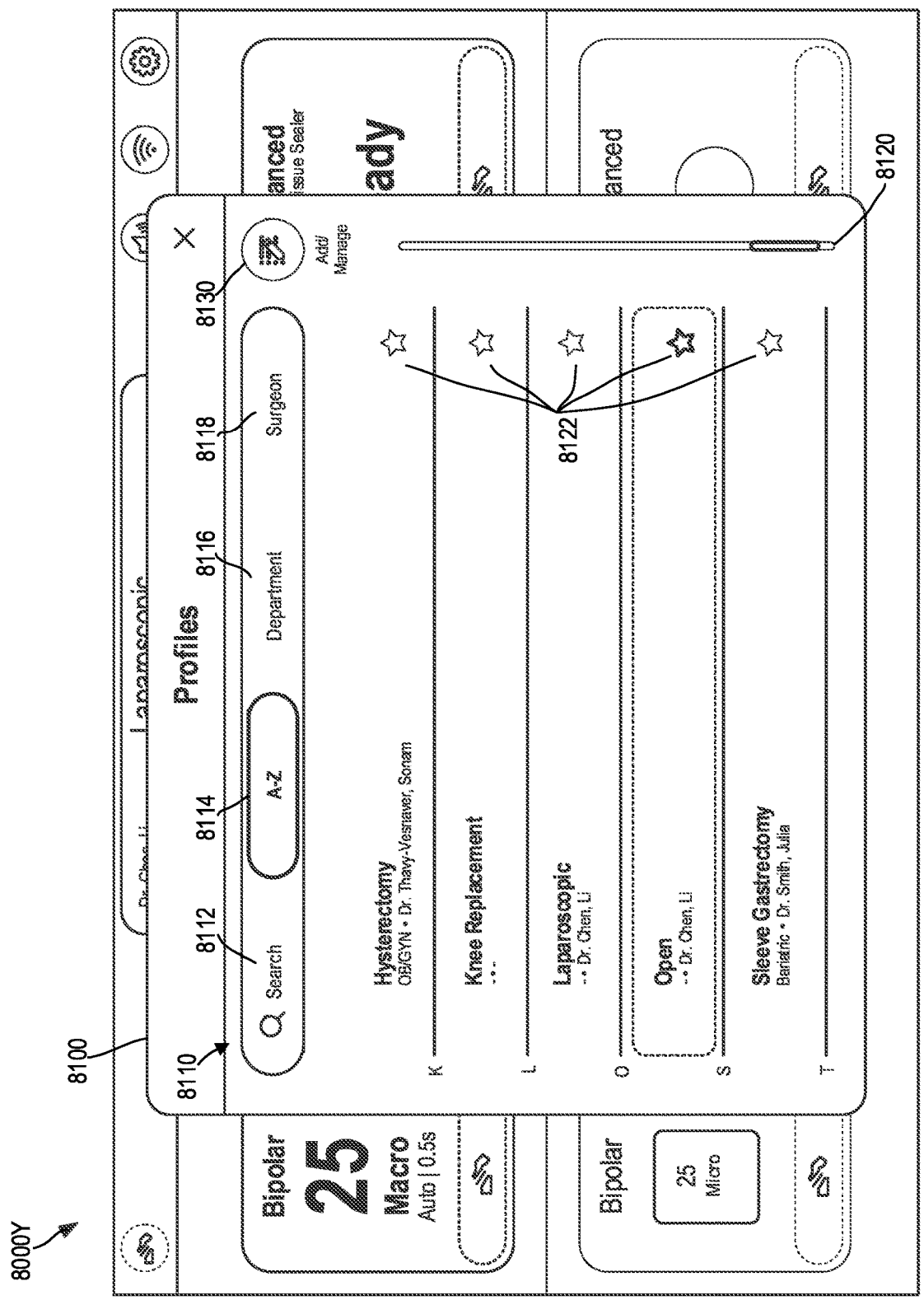

For example, referring now to GUI screen 8000Y of FIG. 35, a user can interact with the profile modal window 8100 and/or the navigation bar 8110 to locate the "Open" profile associated with "Dr. Chen, Li." Note that, in this example, the add/manage button 8130 has not been selected. Thus, tapping on the profile named "Open" will cause the modular energy system to implement the settings associated with this profile and cause GUI 8000 to populate the widgets 2012A-D, 2022A-D and profile bar 8002 thereby displaying the settings associated with the selected profile.

Figure 36:
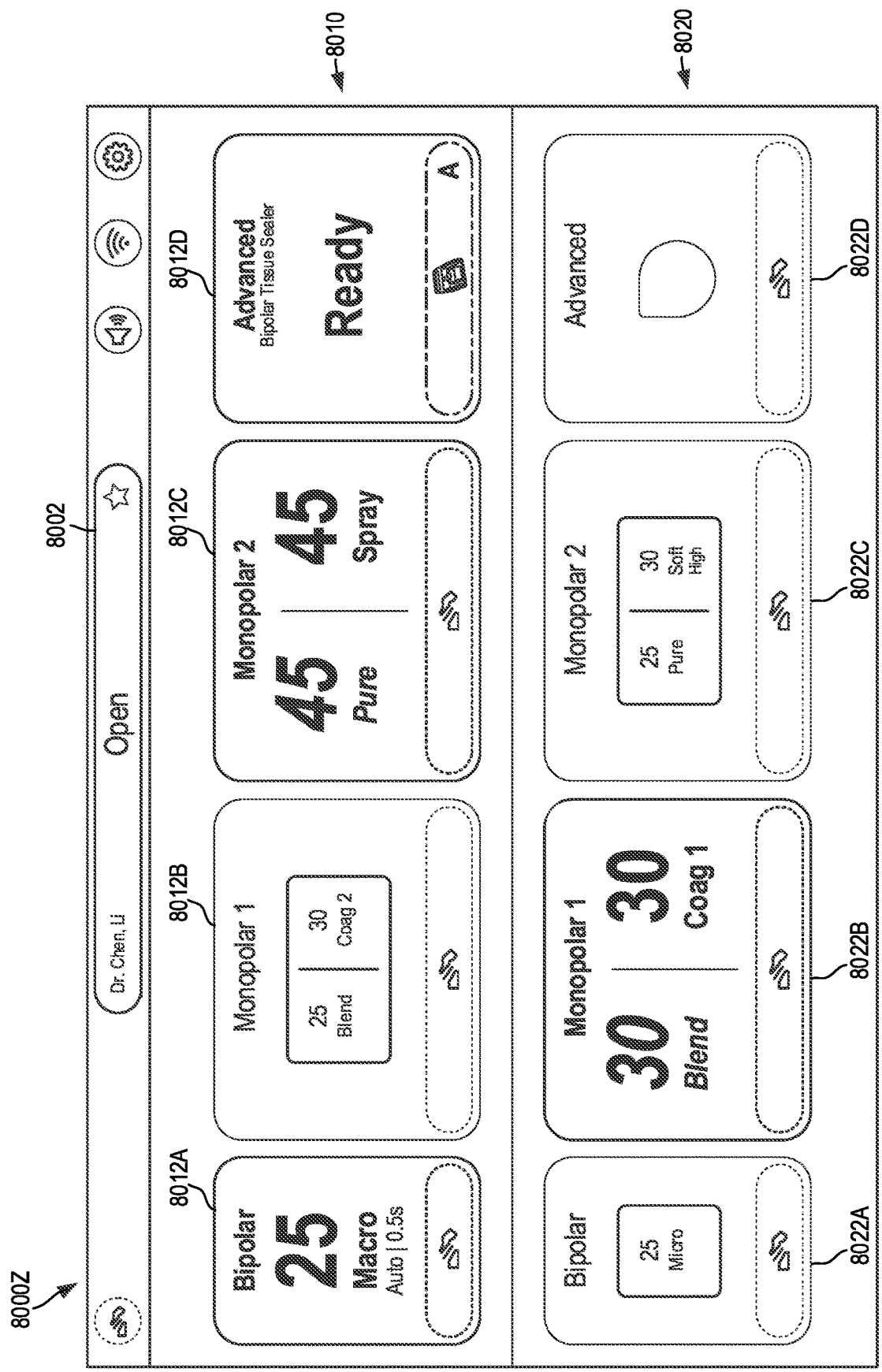

Transitioning from GUI screen 8000Y to GUI screen 8000Z of FIG. 36, GUI 8000 is illustrated displaying the settings associated with the selected "Open" profile. In some aspects, at this point, the user can begin performing a procedure using the modular energy system, wherein the modular energy system is configured based on the settings of the "Open" profile. However, the user may wish to adjust various settings of the "Open" profile before, during, and/or after performing the procedure. Accordingly, tapping or otherwise selecting one of the widgets 8012A-D, 8022A-D can cause an energy modality editing window (e.g., similar to the energy modality editing windows 8230, 8330 discussed above) to open, thereby allowing the user to adjust various settings related to the corresponding energy modality/port. For example, the user may wish to adjust the energy levels associated with the second monopolar port of the first energy module (corresponding with widget 8012C) form 45 to 60. The user can tap on the widget 8012C to open the energy modality editing window and implement the desired setting adjustments.

Figure 37:
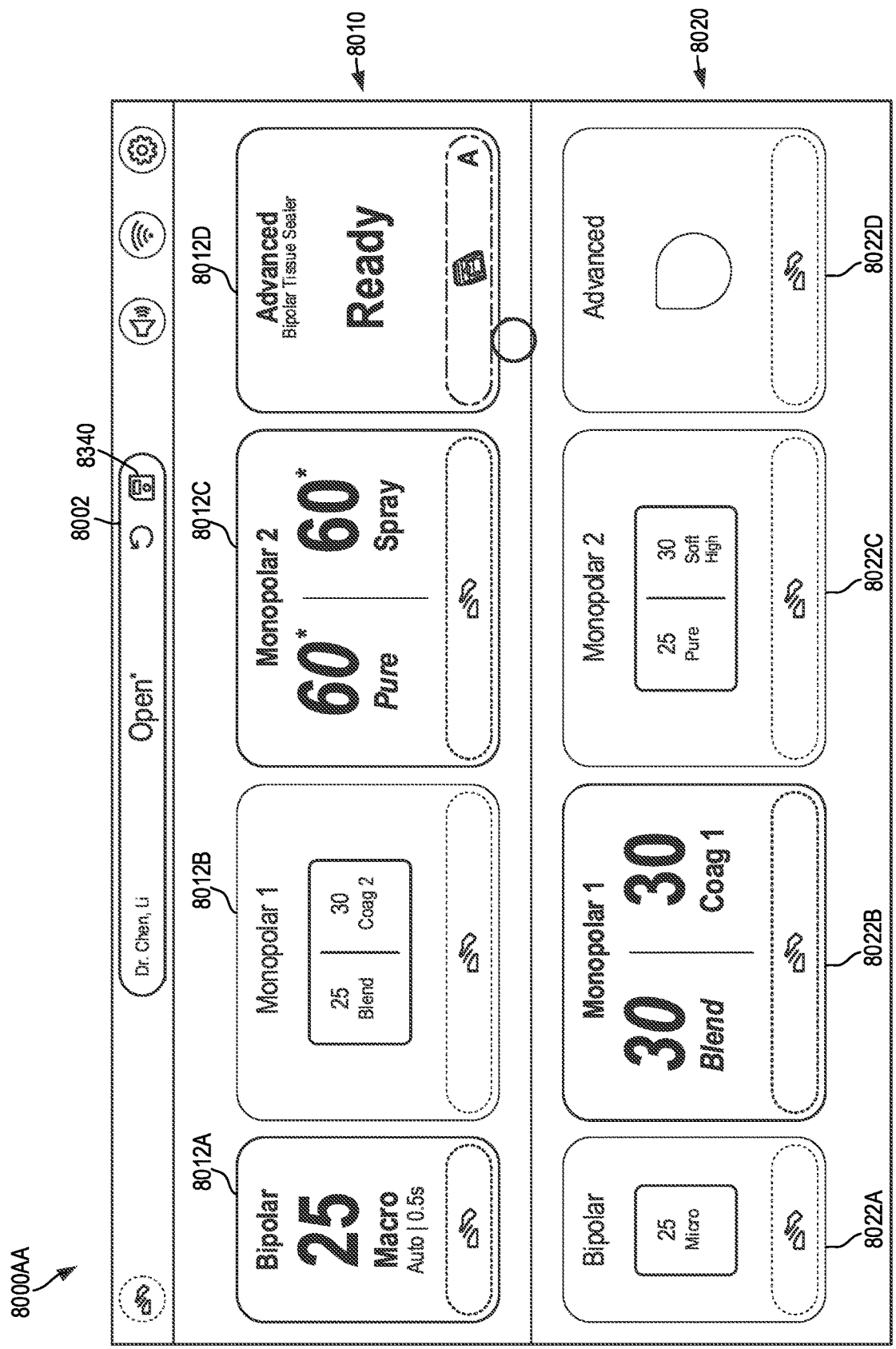

Transitioning from GUI screen 8000Z to GUI screen 8000AA of FIG. 37, based on adjusting settings related to one or more of the energy modalities, GUI 8000 can display one or more elements indicating that the settings of the existing profile have been adjusted. In one aspect, an asterisk may be displayed next to the profile name (e.g., "Open*") in the profile bar 8002 indicating that one or more of the previously saved profile settings have been adjusted. In another aspect, an asterisk may be displayed next to the adjusted settings (e.g., upon adjusting the monopolar 2 energy levels from 45 to 60, "60*" is displayed). In yet another aspect, a save button 8340 may be displayed in the profile bar 8002 that can be selected to save the profile with the adjusted settings.

Figure 38:
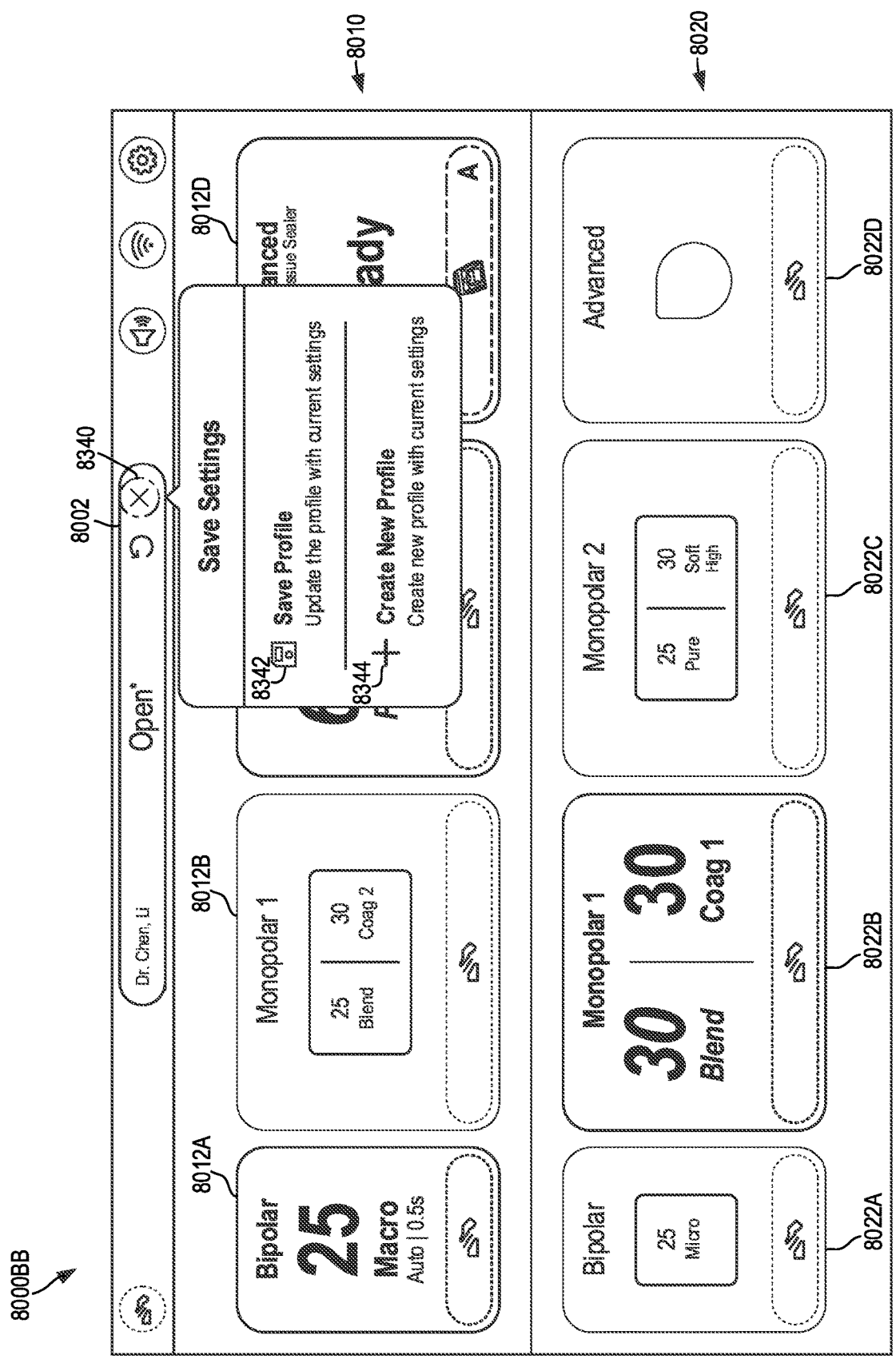
Figure 39:
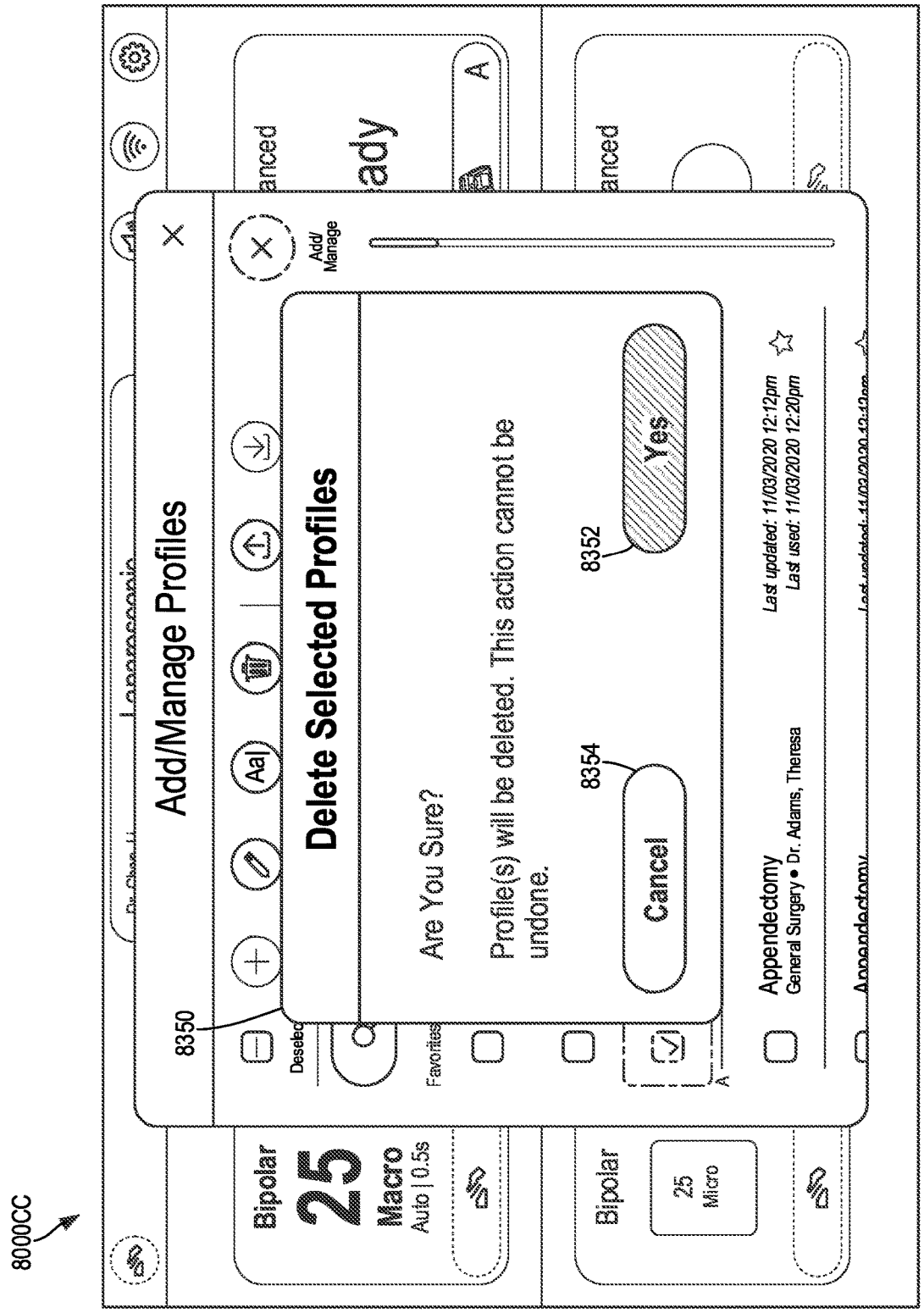

Transitioning from GUI screen 8000AA to GUI screen 8000BB of FIG. 38, based on tapping on the save button 8340, GUI 8000 can be configured to display a menu of options for saving a profile with the adjusted settings. In one aspect, save profile 8342 can be selected to update (i.e., overwrite) the existing profile to include the adjusted settings. In another aspect, create new profile 8344 can be selected to create a new profile that includes the adjusted settings. Thus, by selecting the create new profile 8344 option, the existing profile remains unchanged and an additional profile is created with the adjusted settings. Selecting the create new profile 8344 option can cause the GUI to display the profile naming modal window 8240 thereby allowing the user to input a name for the newly created profile.

Referring again to GUI screen 8000U of FIG. 31, as discuss above, while GUI 8000 is displaying the profile modal window 8100 with the add/manage button 8130 selected, selecting one of the selection check boxes 8216 can cause the edit button 8206, rename button 8208, delete button 8210, and export button 8212 to become active. Tapping or otherwise selecting the delete button 8210 while one or more of the selection check boxes can cause the modular energy system to delete the selected profile(s). In one aspect, prior to the modular energy system deleting the selected profile(s), GUI will display a dialogue box to confirm that the user wishes to delete the selected profile. For example, transitioning from GUI screen 8000U to GUI screen 8000CC of FIG. 39, based on tapping or otherwise selecting the delete button 8210, a dialogue box 8350 may be displayed. The dialogue box 8350 can include a yes button 8352 which can be selected to cause the modular energy system to delete the selected profile(s) and a cancel button 8354 which can be selected to return to the profile modal window 8100 without causing the modular energy system to delete the selected profiles.

Figure 40:
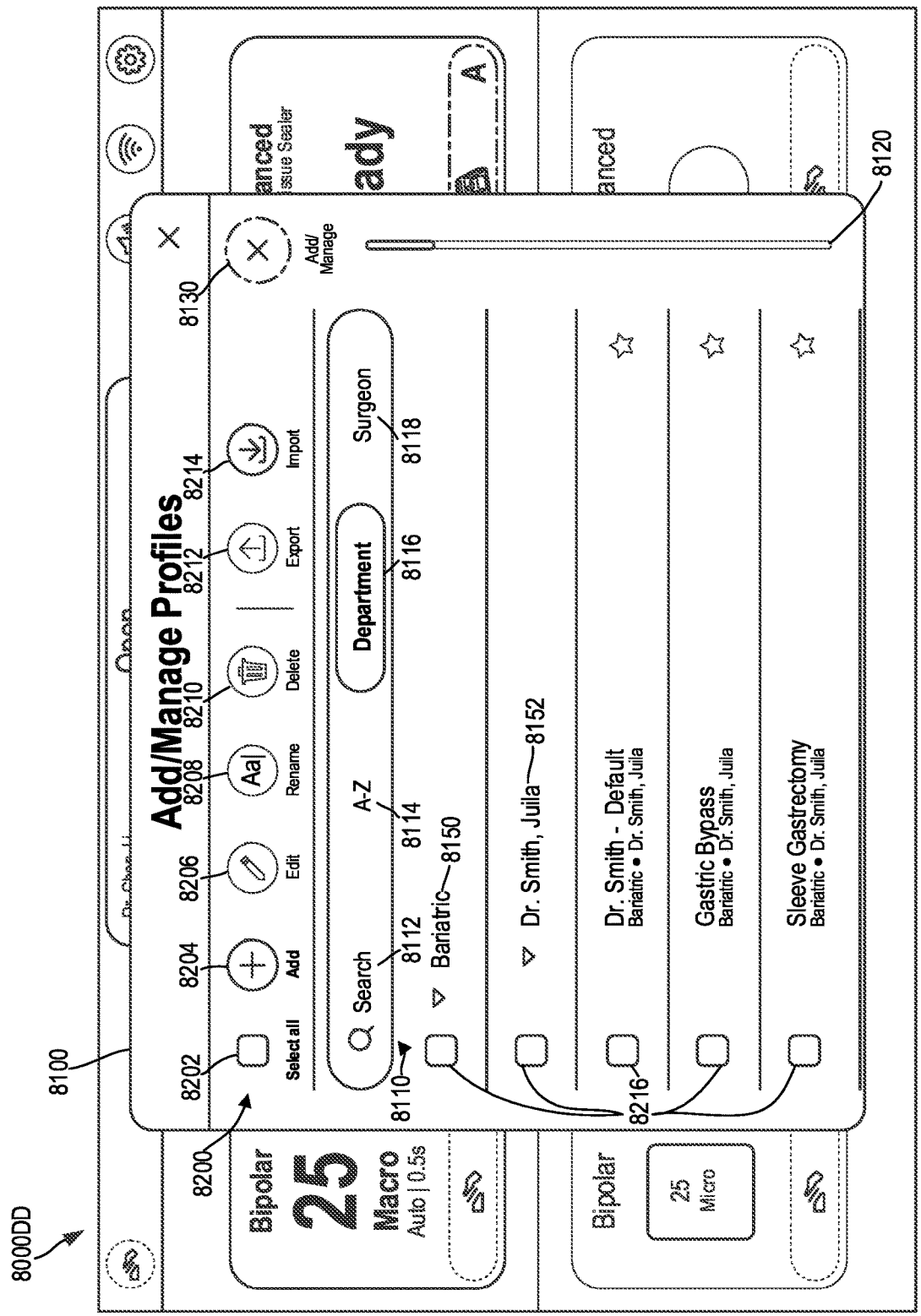
FIGS. 40-45 are illustrative graphical user interface screens for exporting profiles, in accordance with several aspects of the present disclosure.

FIGS. 40-45 are illustrative graphical user interface screens 8000DD-JJ for exporting profiles, in accordance with several aspects of the present disclosure. Referring now to FIG. 40, GUI screen 8000DD is shown displaying the profile modal window 8100 after a user has tapped on or otherwise selected the add/manage button 8130. Further, the department tab 8116 on the navigation bar 8110 has been selected. Accordingly, the profile modal window 8100 is displaying profiles sorted by department, and then by surgeon, with each department heading, surgeon heading, and profile having a selection check box 8216. In one aspect, tapping or otherwise selecting the selection check box 8216 next to any of the headings (e.g., the Bariatric department heading 8150, the Dr. Smith, Julia surgeon heading 8152) can cause all of the headings and/or profiles falling within that heading category to become selected. For example, transitioning to GUI screen 8000EE of FIG. 41, the Bariatric department heading 8150 has been selected, thereby causing the selection check box 8216 next to the Dr. Smith, Julia surgeon heading 8152 and all of the selection profile check boxes 8216 of the profiles within the Bariatric department heading 8150 (and within the Dr. Smith, Julia 8152 heading) to be selected.

Figure 41:
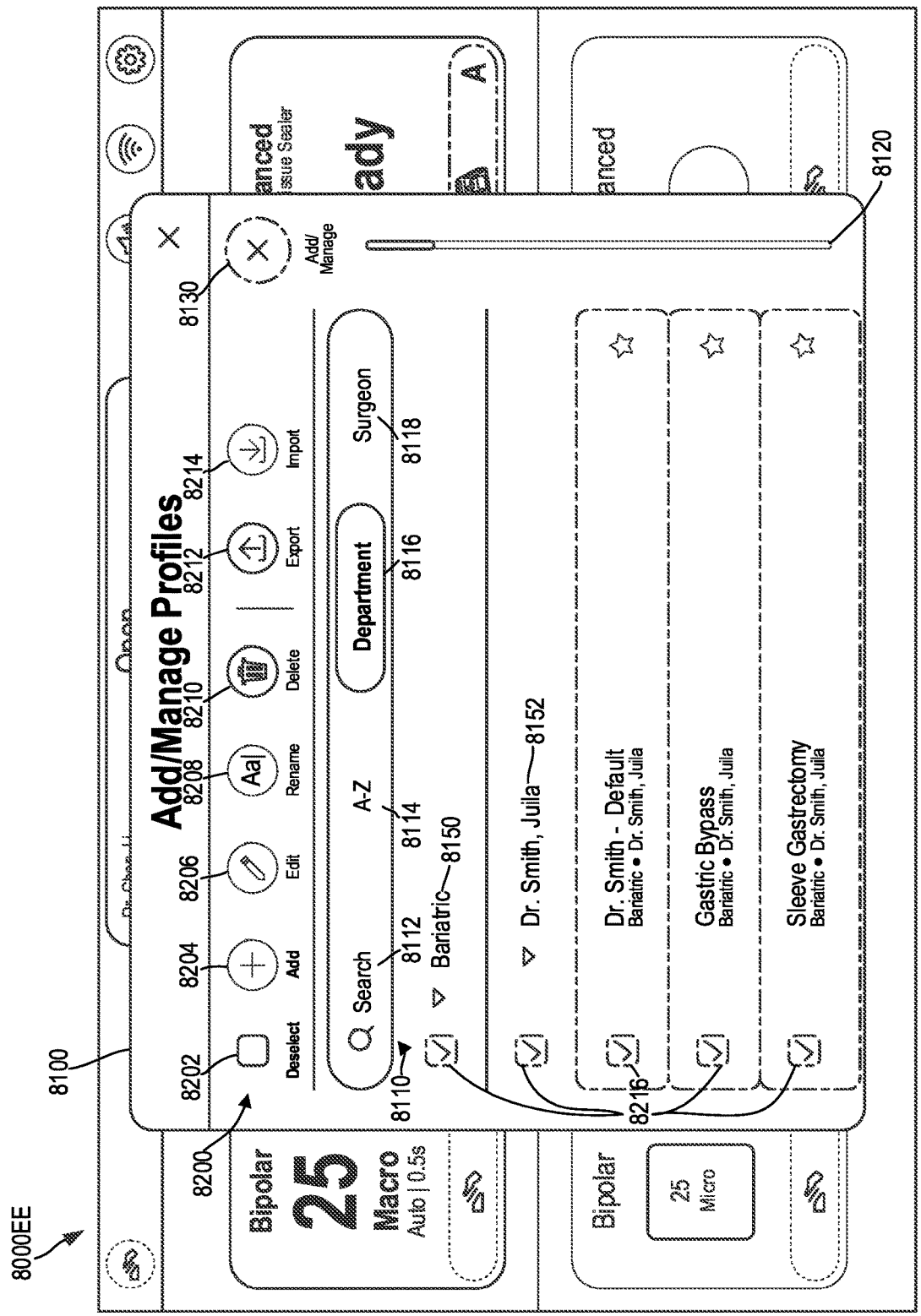
Figure 42:
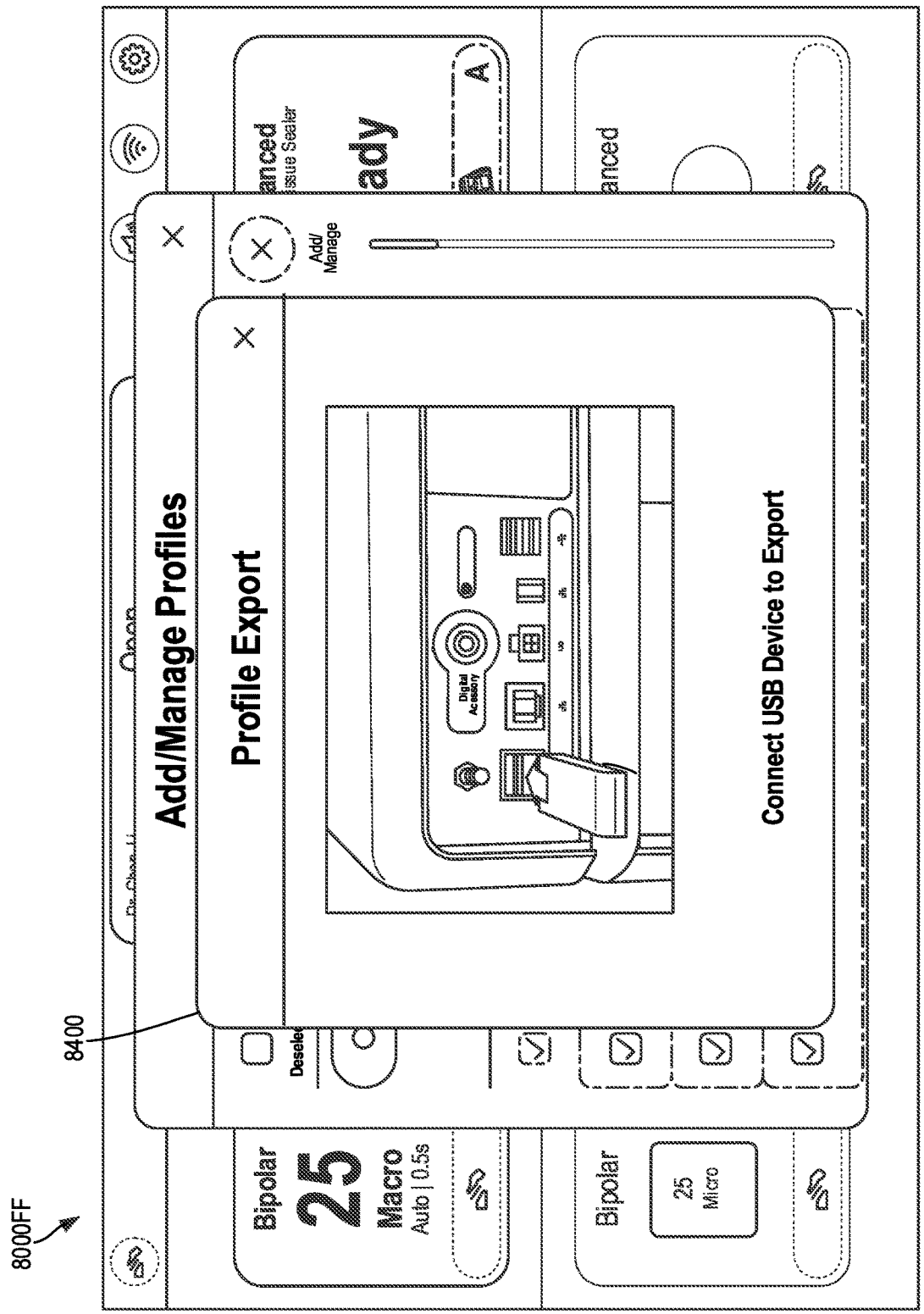

Referring still to GUI screen 8000EE of FIG. 41, selecting the selection check box(es) 8126 next to one or more profiles can cause the export 8212 button to become active. Tapping or otherwise selecting the export button 8212 while one or more profiles are selected can cause the modular energy system to initiate a process for exporting the selected profile(s) to an external device. For example, Transitioning from GUI screen 8000EE to GUI screen 8000FF of FIG. 42, tapping or otherwise selecting the export button 8212 can cause a profile export modal window 8400 to be displayed. The profile export modal window can include instructions for exporting the selected profile(s). For example, the instructions for exporting the selected profile(s) can include an image instructing the user to connect an external device, such as a USB device, to the modular energy system. As shown in the non-limiting aspect of FIG. 42, the instructions for exporting the selected profiles includes an image of the back of a header module of the modular energy system and a USB drive being inserted into a USB port of the header module.

Figure 43:
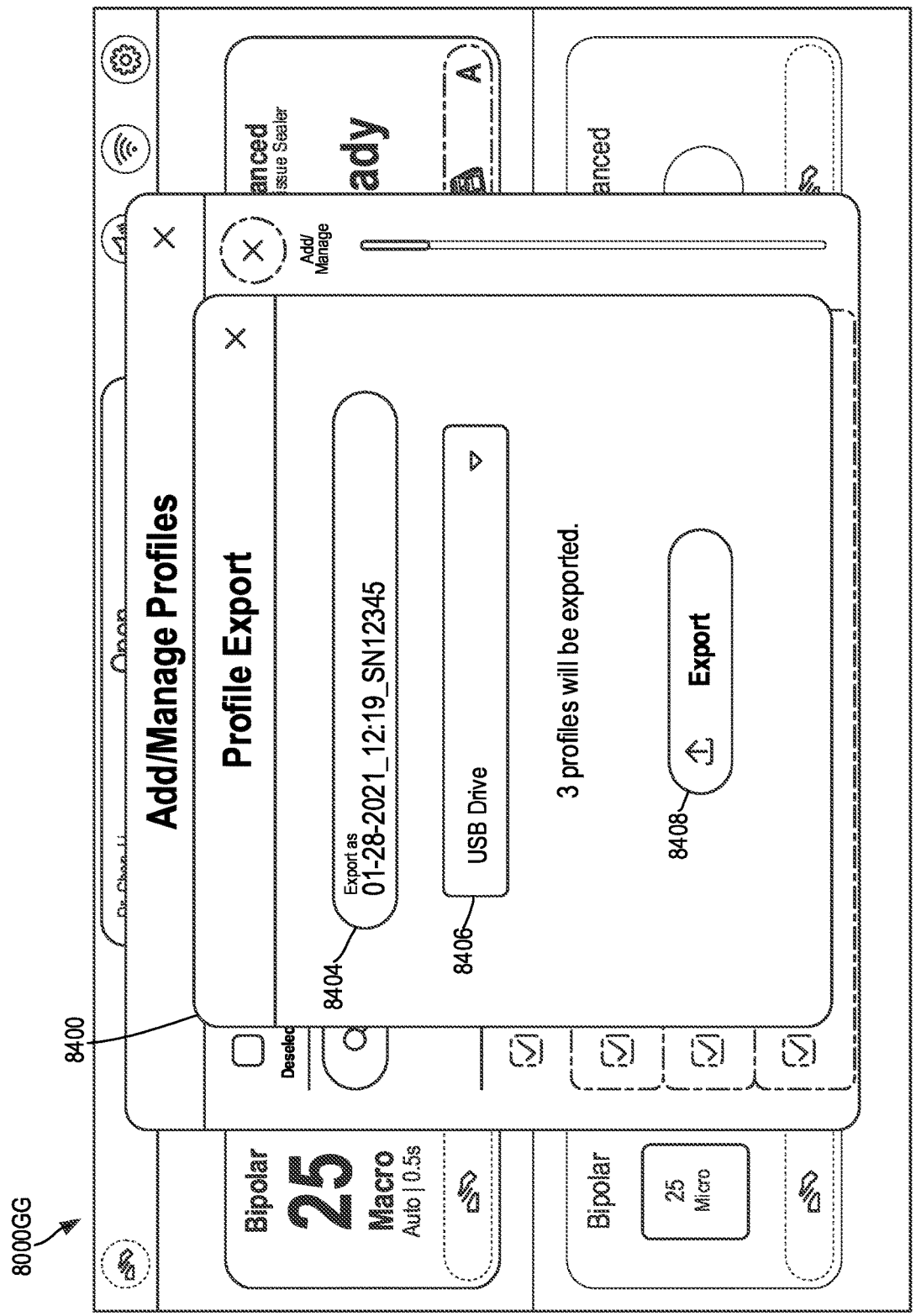

Referring now to GUI screen 8000GG of FIG. 43, the profile export modal window 8400 can include a file export naming bar 8404 and an export location drop down menu 8406. In one aspect, the GUI screen 8000GG can be displayed upon tapping the export button 8212 of the profile modal window 8100 discussed above. In another aspect, the GUI screen 8000GG can be displayed after the user completes the instruction displayed by GUI screen 8000FF of FIG. 42 (e.g., after connecting an external device to the modular energy system). Tapping the file export naming bar 8404 can cause keyboard 8140 to be displayed, thereby allowing the user to input a file name to be assigned to the selected profiles that will be exported. Tapping the export location drop down menu 8406 can case a menu of available export locations to be displayed. The available export locations can be detected based on the devices connected to the modular energy system. For example, the modular energy system can detect USB devices connected to the header modular, storage devices connected to the modular energy system via a wireless connected (e.g., via Bluetooth), and/or other connected storage devices that the selected profile(s) may be exported to. Upon inputting a file name in the file export naming bar 8404 and selecting an export location via the export location drop down menu 8406, the export button 8408 can be selected to cause the modular energy system to initiate the export of the selected profile(s).

Figure 44:
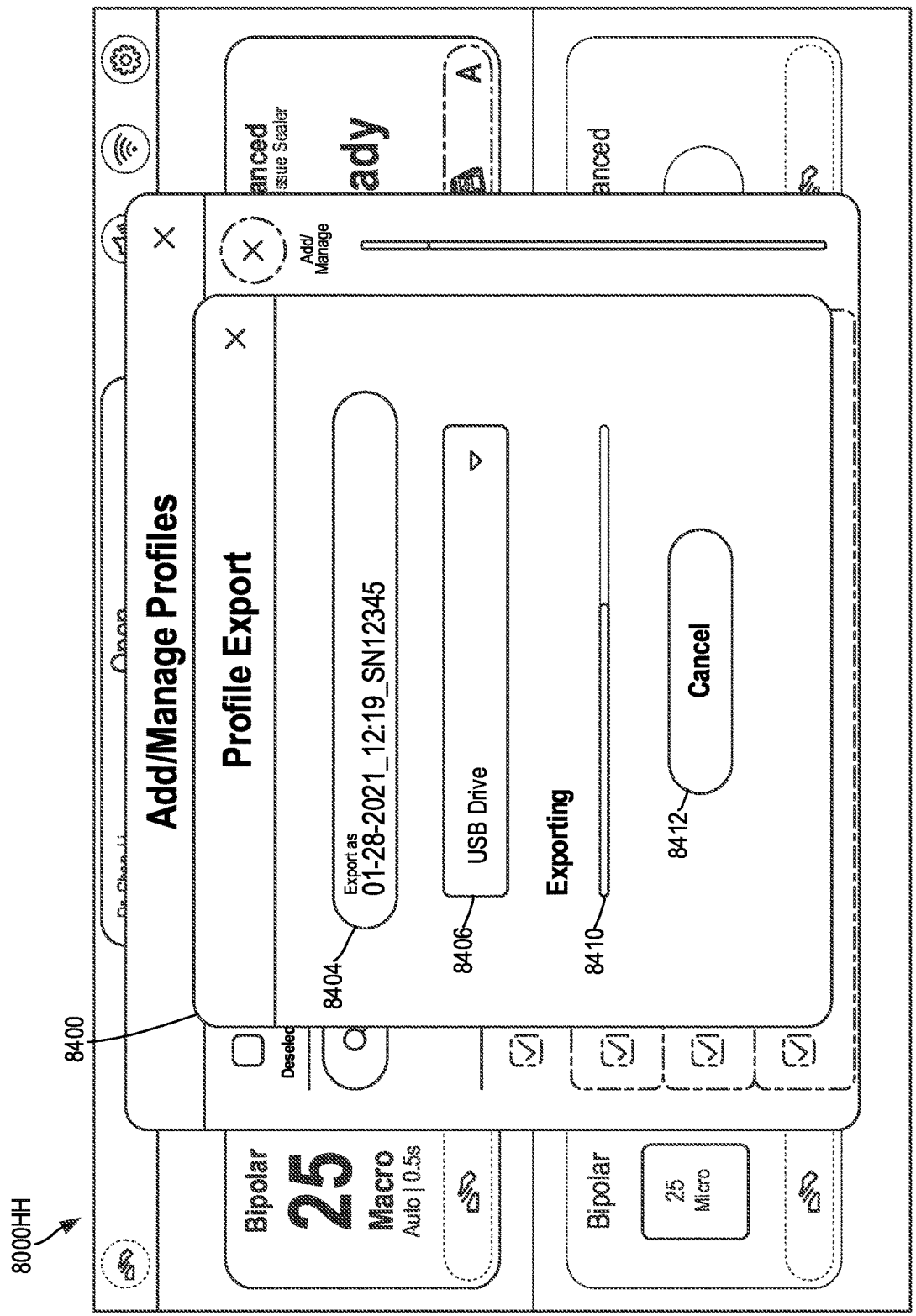

Transitioning from GUI screen 8000GG to GUI screen 8000HH of FIG. 44, tapping on the export button 8408 can cause an export progress bar 8410 to be displayed. The export progress bar 8410 provides information related to the status of the transfer of the file(s) associated with the selected profile(s) to the export location. Prior to the completion of the transfer, the cancel button 8412 can be selected to terminate the export of the selected profile(s) and return to the profile export modal window 8400 shown in GUI screen 8000GG.

Figure 45:
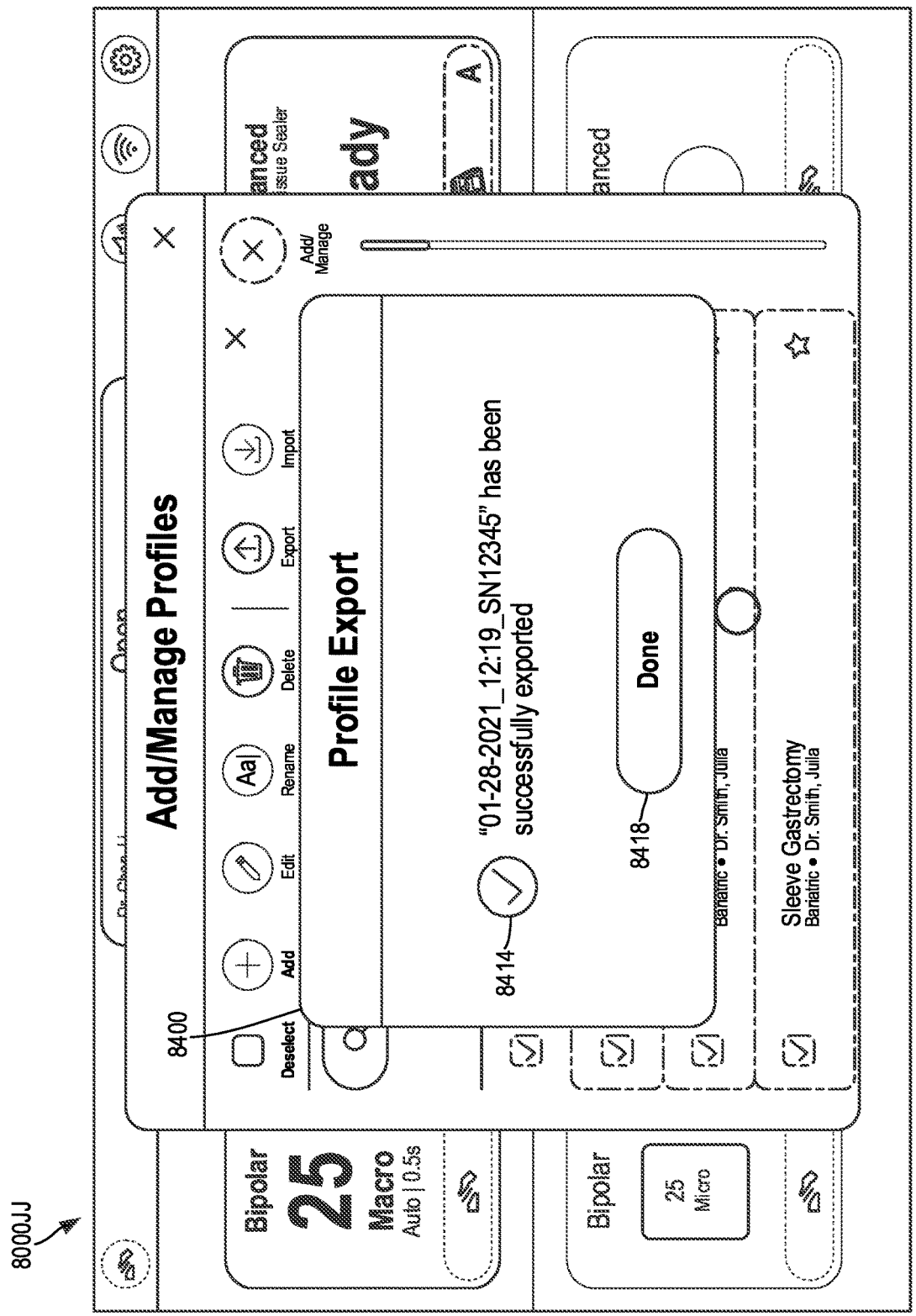

Transitioning from GUI screen 8000HH to GUI screen 8000JJ of FIG. 45, upon completion of the transfer of the file(s) associated with the selected profile(s) to the export location, the profile export modal window 8400 can display a message 8414 indicating that the selected profile(s) have been successfully exported. Further, the profile export modal window 8400 can include a done button 8418 that can be selected to return to the profile modal window 8100.

Returning to GUI screen 8000DD of FIG. 40, upon selecting the add/manage button 8130, the profile modal window can display an import button 8214. Upon tapping or otherwise selecting the import button 8214, GUI 8000 can be configured to display a modal window including options for importing profiles from external devices connected to the modular energy system (not shown in FIG. 40). In one aspect, the modular energy system can be configured to automatically search the storage of connected external devices for profile files. Based on user input via GUI 8000, the modular energy system can be configured to download profile files from connected external devices. The downloaded profiles can be stored on memory associated with the modular energy system, such as memory of a header module of the modular energy system, memory of a surgical system comprising the modular energy system (e.g., storage array 134 of the surgical system 102 of FIG. 3), and/or memory of a cloud-based storage device communicably coupled to the modular energy system (e.g., storage device 105 of the cloud 104 of FIG. 1). The downloaded profiles can be accessed, implemented, and/or edited using GUI 8000 as discussed in detail above.

Figure 46:
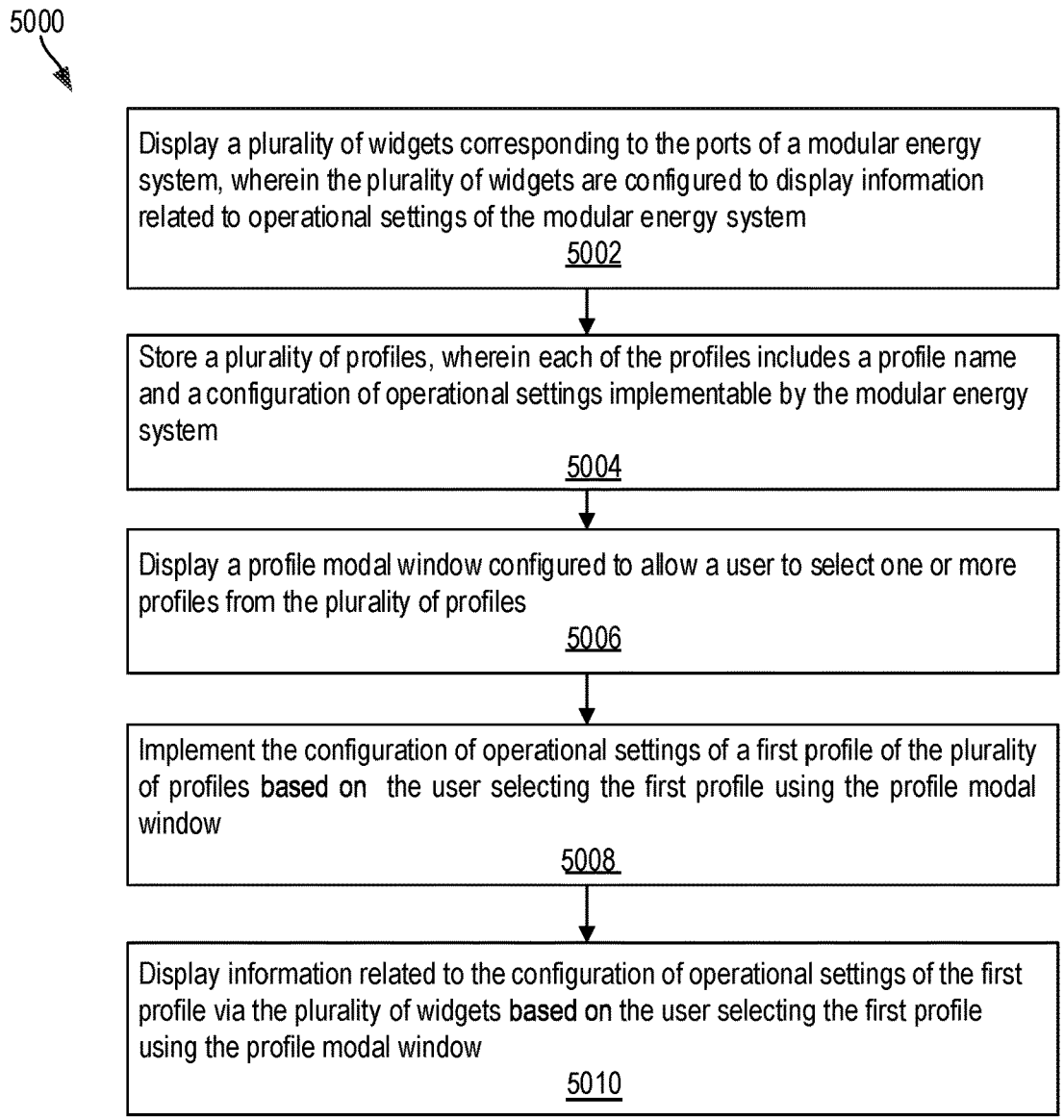
FIG. 46 is a flow chart of a method of implementing operational setting profiles for a modular energy system, in accordance with several aspects of the present disclosure.

FIG. 46 illustrates a method 5000 for implementing operational setting profiles for a modular energy system, according to several non-limiting aspects of this disclosure. The method 5000 may be practiced by any combination of the surgical systems, modular energy systems, energy modules, header modules, ports, surgical instruments, any of the components thereof, and any other devices and systems disclosed herein. For example, the method 5000 may be practiced by a modular energy system including an energy module and a display screen configured to render a graphical user interface (GUI). The energy module can include ports configured to deliver energy modalities to surgical instruments coupled thereto.

In accordance with the method 5000, the GUI can display 5002 a plurality of widgets corresponding to the ports of a modular energy system. The plurality of widgets can be configured to display information related to operational settings of the modular energy system. Further, a memory accessible by the modular energy system can store 5004 a plurality of profiles. In some aspects, each of the profiles can include a profile name and a configuration of operational settings implementable by the modular energy system. The GUI can display 5006 a profile modal window configured to allow a user to select one or more profiles from the plurality of profiles. Further, the modular energy system can implement 5008 the configuration of operational settings of a first profile of the plurality of profiles based on the user selecting the first profile using the profile modal window. Based on the user selecting the first profile using the profile modal window, the plurality of widgets can display 5010 information related to the configuration of operational settings of the first profile.

In one aspect of the method 5000, displaying 5006 the profile modal window can include displaying a search bar configured to allow the user to enter one or more search terms to locate one or more profiles of the plurality of profiles. In another aspect of the method 5000, displaying 5006 the profile modal window can include: displaying an alphabetical GUI object, and displaying the names of the plurality of profiles in alphabetical order based on the user selecting the alphabetical GUI object. In yet another aspect of the method 5000, displaying 5006 the profile modal window can include: displaying a department GUI object, wherein each of the plurality of profiles is associated with a department name; and displaying the names of the plurality of profiles based on the department name associated therewith. In yet another aspect of the method 5000, displaying 5006 the profile modal window can include: displaying a surgeon GUI object, wherein each of the plurality of profiles is associated with a surgeon name; and displaying the names of the plurality of profiles based on the surgeon name associated therewith.

In one aspect of the method 5000, the GUI can display a profile creation and editing mode. The profile creation and editing mode can be configured to allow a user to create a new profile by inputting information related to a configuration of operational settings and saving the new profile to the memory, thereby adding the new profile to the plurality of profiles. In addition to or in lieu of the above, the profile creation and edit mode can be configured to allow a user to edit a second profile of the plurality of profiles by adjusting the configuration of operational settings of the second profile and saving the second profile with the adjusted configuration of operational settings to the memory.

In various aspects of the method 5000, the GUI can display an energy modality editing modal window based on a user selecting a first widget of the plurality of widgets. Further, based on the user interacting with the energy modality editing modal window, the modular energy system can adjust the configuration of operational settings of the first profile based on the user interacting with the energy modality editing modal window. In one aspect, the modular energy system can save the adjusted configuration of operational settings of the first profile to the memory, thereby overwriting the first profile to create an updated first profile. In another aspect, the modular energy system can save the adjusted configuration of operational settings of the first profile to the memory, thereby creating new profile and leaving the first profile unchanged in the memory.

In various aspects of the method 5000, displaying 5006 the profile modal window can include displaying the profile names, wherein each profile name is associated with a check box, and displaying at least one of an edit button, a rename button, a delete button, and/or an export button. In one aspect, based on a user selecting the check box associated with the name of a second profile of the plurality of profiles and selecting the edit button, the GUI can display a profile creating and editing mode. In another aspect, based on a user selecting the check box associated with the name of a second profile of the plurality of profiles and selecting the delete button, the modular energy system can delete the second profile. In yet another aspect, based on a user selecting the check box associated with the name of a second profile of the plurality of profiles and selecting the export button, the modular energy system can export the second profile to an external device.

EXAMPLES

Various aspects of the devices, systems, and methods for assigning a footswitch to a port of a modular energy system described herein are set out in the following examples.

Example 1: A method of implementing operational setting profiles for a modular energy system, wherein the modular energy system comprises an energy module and a display screen configured to render a graphical user interface (GUI), and wherein the energy module comprises ports configured to deliver energy modalities to surgical instruments coupled thereto, the method comprising: displaying, by the GUI, a plurality of widgets corresponding to the ports, wherein the plurality of widgets are configured to display information related to operational settings of the modular energy system; storing, by a memory accessible by the modular energy system, a plurality of profiles, wherein each of the profiles comprises a profile name and a configuration of operational settings implementable by the modular energy system; displaying, by the GUI, a profile modal window configured to allow a user to select one or more profiles from the plurality of profiles; implementing, by the modular energy system, the configuration of operational settings of a first profile of the plurality of profiles based on the user selecting the first profile using the profile modal window; and displaying, by the plurality of widgets, information related to the configuration of operational settings of the first profile based on the user selecting the first profile using profile modal window.

Example 2: The method of Example 1, wherein displaying the profile modal window comprises: displaying a search bar configured to allow the user to enter one or more search terms to locate one or more profiles of the plurality of profiles.

Example 3: The method of any of Examples 1-2, wherein displaying the profile modal window comprises: displaying an alphabetical GUI object; and displaying the names of the plurality of profiles in alphabetical order based on the user selecting the alphabetical GUI object.

Example 4: The method of any of Examples 1-3, wherein displaying the profile modal window comprises: displaying a department GUI object, wherein each of the plurality of profiles is associated with a department name; and displaying the names of the plurality of profiles based on the department name associated therewith.

Example 5: The method of any of Examples 1-4, wherein displaying the profile modal window comprises: displaying a surgeon GUI object, wherein each of the plurality of profiles is associated with a surgeon name; and displaying the names of the plurality of profiles based on the surgeon name associated therewith.

Example 6: The method of any of Examples 1-5, further comprising: displaying, by the GUI, a profile creation and editing mode, wherein the profile creation and editing mode is configured to allow a user to: create a new profile by inputting information related to a configuration of operational settings and saving the new profile to the memory, thereby adding the new profile to the plurality of profiles; and edit a second profile of the plurality of profiles by adjusting the configuration of operational settings of the second profile and saving the second profile with the adjusted configuration of operational settings to the memory.

Example 7: The method of any of Examples 1-6, further comprising: displaying, by the GUI, an energy modality editing modal window based on the user selecting a first widget of the plurality of widgets; adjusting, by the modular energy system, the configuration of operational settings of the first profile based on the user interacting with the energy modality editing modal window.

Example 8: The method of any of Examples 1-7, further comprising: saving, by the modular energy system, the adjusted configuration of operational settings of the first profile to the memory, thereby overwriting the first profile to create an updated first profile.

Example 9: The method of any of Examples 1-8, further comprising: saving, by the modular energy system, the adjusted configuration of operational settings of the first profile to the memory, thereby creating new profile and leaving the first profile unchanged in the memory.

Example 10: The method of any of Examples 1-9, wherein displaying the profile modal window comprises:

displaying, by the GUI, the profile names, wherein each profile name is associated with a check box; and displaying, by the GUI, at least one of an edit button, a rename button, a delete button, and an export button.

Example 11: The method of any of Examples 1-10, wherein displaying the profile modal window comprises displaying the edit button, the method further comprising: displaying, by the GUI, a profile creating and editing mode based on the user selecting the check box associated with one of the profile names and selecting the edit button.

Example 12: The method of any of Examples 1-11, wherein displaying the profile modal window comprises displaying the delete button, the method further comprising: deleting, by the modular energy system, a second profile of the plurality of profiles based on the user selecting the check box associated with the name of the second profile and selecting the delete button.

Example 13: The method of any of Examples 1-12, wherein displaying the profile modal window comprises displaying the export button, the method further comprising: exporting, by the modular energy system, a second profile of the plurality of profiles to an external device coupled to the modular energy system based on the user selecting the check box associated with the name of the second profile and selecting the export button.

Example 14: A modular energy system for use in a surgical environment, the modular energy system comprising: one or more energy modules, wherein each of the one or more energy modules comprises ports, and wherein each of the ports is configured to deliver an energy modality to a surgical instrument connected thereto; a memory comprising a plurality of profiles, wherein each profile comprises a name and a configuration of operational settings implementable by the modular energy system; and a header module comprising a display screen, wherein the display screen is configured to render a graphical user interface (GUI), and wherein GUI is configured to: display a plurality of widgets corresponding to the ports, wherein the plurality of widgets are configured to display information related to operational settings of the modular energy system; display a window configured to allow a user to select from the plurality of profiles comprised in the memory; and populate the widgets with information related to the configuration of operational settings of one of the profiles based on the user selecting the profile.

Example 15: The system of Example 13, wherein the window comprises at least one of: a search bar configured to allow the user to enter one or more search terms to locate one or more profiles of the plurality of profiles; an alphabetical GUI object, wherein the window is configured to display the names of the plurality of profiles in alphabetical order based on the user selecting the alphabetical GUI object; a department GUI object, wherein each of the plurality of profiles is associated with a department name, and wherein the window is configured to display the names of the plurality of profiles based on the department name associated therewith based on the user selecting the department GUI object; and a surgeon GUI object, wherein each of the plurality of profiles is associated with a surgeon name, and wherein the window is configured to display the names of the plurality of profiles based on the surgeon name associated therewith based on the user selecting the surgeon GUI object.

Example 16: The system of any of Examples 13-15, wherein the GUI is further configured to: display a profile creation and editing mode configured to allow a user to create a new profile and save the profile to the memory, thereby adding the new profile to the plurality of profiles.

Example 17: The system of any of Examples 13-16, wherein the GUI is further configured to: display an energy modality editing modal window based on the user selecting a first widget of the plurality of widgets, wherein the energy modality editing modal window is configured to allow the user to edit operational settings of the port of the plurality of ports corresponding to the first widget.

Example 18: The system of any of Examples 13-17, wherein the GUI is further configured to: display a profile creation and editing mode configured to allow a user to edit the configuration of operational settings of one of the plurality of profiles.

Example 19: The system of any of Examples 13-18, wherein the GUI is further configured to display: an edit button in the window, wherein the user can select the edit button to cause the GUI to display profile creation and editing mode.

Example 20: The system of any of Examples 13-19, wherein the GUI is further configured to display: a delete button in the window, wherein the user can select the delete button to cause the modular energy system to delete one or more of the plurality of profiles from the memory.

Example 21: The system of any of Examples 13-20, wherein the header module further comprises a USB port, and wherein the GUI is further configured to display: an export button in the window, wherein the user can select the export button to cause the modular energy system to export one or more profiles of the plurality of profiles to a USB drive connected to the USB port.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method of implementing operational setting profiles for a modular energy system, wherein the modular energy system comprises an energy module and a display screen configured to render a graphical user interface (GUI), and wherein the energy module comprises ports configured to deliver energy modalities to surgical instruments coupled thereto, the method comprising:

displaying, by the GUI, a plurality of widgets corresponding to the ports, wherein the plurality of widgets are configured to display information related to operational settings of the modular energy system;

storing, by a memory accessible by the modular energy system, a plurality of profiles, wherein each of the profiles comprises a profile name and a configuration of operational settings implementable by the modular energy system, wherein the operational settings comprise a first set of settings selected by a user and associated with the profile name that indicate one or more energy settings for each port and a second set of settings selected by the user and associated with the profile name that indicate whether each port is configured to be controlled by a foot switch;

displaying, by the GUI, a profile modal window configured to allow a user to select one or more profiles from the plurality of profiles;

implementing, by the modular energy system, the configuration of operational settings of a first profile of the plurality of profiles based on the user selecting the first profile using the profile modal window;

displaying, by the plurality of widgets, information related to the configuration of operational settings of the first profile based on the user selecting the first profile using profile modal window;

during a surgical procedure, displaying an energy modality editing window for the configuration of operational settings of the first profile, the surgical procedure being performed based upon the configuration of operational settings of the first profile;

during the surgical procedure, receiving, from a user via the energy modality editing window, an adjustment to the configuration of operational settings; and upon completion of the surgical procedure, updating the configuration of operational settings of the first profile with the adjusted configuration of operational settings.

2. The method of claim 1, wherein displaying the profile modal window comprises:
displaying a search bar configured to allow the user to enter one or more search terms to locate one or more profiles of the plurality of profiles.

3. The method of claim 1, wherein displaying the profile modal window comprises:
displaying an alphabetical GUI object; and
displaying the names of the plurality of profiles in alphabetical order based on the user selecting the alphabetical GUI object.

4. The method of claim 1, wherein displaying the profile modal window comprises:
displaying a department GUI object, wherein each of the plurality of profiles is associated with a department name; and
displaying the names of the plurality of profiles based on the department name associated therewith.

5. The method of claim 1, wherein displaying the profile modal window comprises:
displaying a surgeon GUI object, wherein each of the plurality of profiles is associated with a surgeon name; and
displaying the names of the plurality of profiles based on the surgeon name associated therewith.

6. The method of claim 1, further comprising:
displaying, by the GUI, a profile creation and editing mode, wherein the profile creation and editing mode is configured to allow a user to:
create a new profile by inputting information related to a configuration of operational settings and saving the new profile to the memory, thereby adding the new profile to the plurality of profiles; and
edit a second profile of the plurality of profiles by adjusting the configuration of operational settings of the second profile and saving the second profile with the adjusted configuration of operational settings to the memory.

7. The method of claim 1, further comprising:
displaying, by the GUI, an energy modality editing modal window based on the user selecting a first widget of the plurality of widgets;
adjusting, by the modular energy system, the configuration of operational settings of the first profile based on the user interacting with the energy modality editing modal window.

8. The method of claim 7, further comprising:
saving, by the modular energy system, the adjusted configuration of operational settings of the first profile to the memory, thereby overwriting the first profile to create an updated first profile.

9. The method of claim 7, further comprising:
saving, by the modular energy system, the adjusted configuration of operational settings of the first profile to the memory, thereby creating new profile and leaving the first profile unchanged in the memory.

10. The method of claim 1, wherein displaying the profile modal window comprises:
displaying, by the GUI, the profile names, wherein each profile name is associated with a check box; and
displaying, by the GUI, at least one of an edit button, a rename button, a delete button, and an export button.

11. The method of claim 10, wherein displaying the profile modal window comprises displaying the edit button, the method further comprising:
displaying, by the GUI, a profile creating and editing mode based on the user selecting the check box associated with one of the profile names and selecting the edit button.

12. The method of claim 10, wherein displaying the profile modal window comprises displaying the delete button, the method further comprising:
deleting, by the modular energy system, a second profile of the plurality of profiles based on the user selecting the check box associated with the name of the second profile and selecting the delete button.

13. The method of claim 10, wherein displaying the profile modal window comprises displaying the export button, the method further comprising:
exporting, by the modular energy system, a second profile of the plurality of profiles to an external device coupled to the modular energy system based on the user selecting the check box associated with the name of the second profile and selecting the export button.

14. A modular energy system for use in a surgical environment, the modular energy system comprising:
one or more energy modules, wherein each of the one or more energy modules comprises ports, and wherein each of the ports is configured to deliver an energy modality to a surgical instrument connected thereto;
a memory comprising a plurality of profiles, wherein each profile comprises a name and a configuration of operational settings implementable by the modular energy system, wherein the operational settings comprise a first set of settings selected by a user and associated with the profile name that indicate one or more energy settings for each port and a second set of settings selected by the user and associated with the profile name that indicate whether each port is configured to be controlled by a foot switch; and a header module comprising a display screen, wherein the display screen is configured to render a graphical user interface (GUI), and wherein GUI is configured to:
- display a plurality of widgets corresponding to the ports, wherein the plurality of widgets are configured to display information related to operational settings of the modular energy system;
- display a window configured to allow a user to select from the plurality of profiles comprised in the memory;
- populate the widgets with information related to the configuration of operational settings of a first profile of the plurality of profiles based on the user selecting the first profile;
- during the surgical procedure, display an energy modality editing window for the configuration of operational settings of the first profile;
- during the surgical procedure, receive, from a user via the energy modality editing window, an adjustment to the configuration of operational settings; and
- upon completion of the surgical procedure, update the configuration of operational settings of the first profile with the adjusted configuration of operational settings.

15. The system of claim 14, wherein the window comprises at least one of:
- a search bar configured to allow the user to enter one or more search terms to locate one or more profiles of the plurality of profiles;
- an alphabetical GUI object, wherein the window is configured to display the names of the plurality of profiles in alphabetical order based on the user selecting the alphabetical GUI object;
- a department GUI object, wherein each of the plurality of profiles is associated with a department name, and wherein the window is configured to display the names of the plurality of profiles based on the department name associated therewith based on the user selecting the department GUI object; and
- a surgeon GUI object, wherein each of the plurality of profiles is associated with a surgeon name, and wherein the window is configured to display the names of the plurality of profiles based on the surgeon name associated therewith based on the user selecting the surgeon GUI object.

16. The system of claim 14, wherein the GUI is further configured to:
- display a profile creation and editing mode configured to allow a user to create a new profile and save the profile to the memory, thereby adding the new profile to the plurality of profiles.

17. The system of claim 14, wherein the GUI is further configured to:
- display an energy modality editing modal window based on the user selecting a first widget of the plurality of widgets, wherein the energy modality editing modal window is configured to allow the user to edit operational settings of the port of the plurality of ports corresponding to the first widget.

18. The system of claim 14, wherein the GUI is further configured to:
- display a profile creation and editing mode configured to allow a user to edit the configuration of operational settings of one of the plurality of profiles.

19. The system of claim 14, wherein the GUI is further configured to display:
- an edit button in the window, wherein the user can select the edit button to cause the GUI to display a profile creation and editing mode.

20. The system of claim 14, wherein the header module further comprises a USB port, and wherein the GUI is further configured to display:
- an export button in the window, wherein the user can select the export button to cause the modular energy system to export one or more profiles of the plurality of profiles to a USB drive connected to the USB port.

21. A method of implementing operational setting profiles for a modular energy system, wherein the modular energy system comprises an energy module and a display screen configured to render a graphical user interface (GUI), and wherein the energy module comprises ports configured to deliver energy modalities to surgical instruments coupled thereto, the method comprising:
- displaying, by the GUI, a plurality of widgets corresponding to the ports, wherein the plurality of widgets are configured to display information related to operational settings of the modular energy system;
- storing, by a memory accessible by the modular energy system, a plurality of profiles, wherein each of the profiles comprises a profile name and a configuration of operational settings implementable by the modular energy system;
- displaying, by the GUI, a profile modal window configured to allow a user to select one or more profiles from the plurality of profiles;
- implementing, by the modular energy system, the configuration of operational settings of a first profile of the plurality of profiles based on the user selecting the first profile using the profile modal window;
- displaying, by the plurality of widgets, information related to the configuration of operational settings of the first profile based on the user selecting the first profile using profile modal window;
- commencing a surgical procedure based upon the configuration of operational settings of the first profile;
- during the surgical procedure, displaying an energy modality editing window for the configuration of operational settings of the first profile;
- during the surgical procedure, receiving, from a user via the energy modality editing window, an adjustment to the configuration of operational settings; and
- upon completion of the surgical procedure, updating the configuration of operational settings of the first profile with the adjusted configuration of operational settings.

\* \* \* \* \*